(12) United States Patent
Lekivetz et al.

(10) Patent No.: US 10,535,422 B2
(45) Date of Patent: Jan. 14, 2020

(54) OPTIMAL SCREENING DESIGNS

(71) Applicant: SAS Institute Inc., Cary, NC (US)

(72) Inventors: Ryan Adam Lekivetz, Cary, NC (US); Caleb Bridges King, Cary, NC (US); Joseph Albert Morgan, Raleigh, NC (US); Bradley Allen Jones, Cary, NC (US)

(73) Assignee: SAS Institute Inc., Cary, NC (US)

( * ) Notice: Subject to any disclaimer, the term of this patent is extended or adjusted under 35 U.S.C. 154(b) by 0 days.

(21) Appl. No.: 16/507,769

(22) Filed: Jul. 10, 2019

(65) Prior Publication Data

US 2019/0346297 A1    Nov. 14, 2019

Related U.S. Application Data

(63) Continuation-in-part of application No. 16/240,182, filed on Jan. 4, 2019, now Pat. No. 10,386,271, which (Continued)

(51) Int. Cl.
*G16C 20/70* (2019.01)
*G06N 5/02* (2006.01)

(Continued)

(52) U.S. Cl.
CPC ............. *G16C 20/70* (2019.02); *G06F 16/90* (2019.01); *G06N 5/022* (2013.01); *G16C 20/80* (2019.02); *G16C 20/90* (2019.02)

(58) Field of Classification Search
None
See application file for complete search history.

(56) References Cited

U.S. PATENT DOCUMENTS 6,460,068 B1   10/2002 Novaes
7,269,517 B2 *  9/2007 Bondarenko .......... G16B 50/00
                                                       702/19

(Continued)

OTHER PUBLICATIONS

"Main Effects Screening: A Distributed Continuous Quality Assurance Process for Monitoring Performance Degradation in Evolving Software Systems", by C. Yilmaz, A. Krishna, A. Merron, A. Porter, D. Schmidt, A. Gokhale, and B. Natarajan, Proc 27th Int'l Conf on Software Eng, Jan. 2005, pp. 293-302. (Year: 2005).*

(Continued)

*Primary Examiner* — James A Thompson
(74) *Attorney, Agent, or Firm* — Coats & Bennett, PLLC

(57) ABSTRACT

A computing device obtains a metric N indicating a quantity of a plurality of test cases for an output design of an experiment Each element of a test case of the output design is a test condition for testing one of factors for the experiment. The computing device obtains input indicating a quantity p of an indicated plurality of factors for the output design. The computing device determines whether there are stored instructions for generating an initial screening design for the experiment. The computing device responsive to determining that there are stored instructions, selects, using the stored instructions, the initial screening design for the experiment. The computing device determines whether to modify the initial screening design based on modification criteria comprising a secondary criterion, the metric N, and/or the quantity p. The computing device outputs an indication of the updated screening design for the output design of the experiment.

30 Claims, 53 Drawing Sheets

Related U.S. Application Data is a continuation-in-part of application No. 16/154,290, filed on Oct. 8, 2018, now Pat. No. 10,338,993.

(60) Provisional application No. 62/796,214, filed on Jan. 24, 2019, provisional application No. 62/807,286, filed on Feb. 19, 2019, provisional application No. 62/816,150, filed on Mar. 10, 2019, provisional application No. 62/728,361, filed on Sep. 7, 2018, provisional application No. 62/702,247, filed on Jul. 23, 2018, provisional application No. 62/661,057, filed on Apr. 22, 2018.

(51) Int. Cl.
    *G16C 20/80* (2019.01)
    *G06F 16/90* (2019.01)
    *G16C 20/90* (2019.01)

(56) References Cited

U.S. PATENT DOCUMENTS

| | | | |
|---|---|---|---|
| 7,308,418 B2 * | 12/2007 | Malek | G06Q 30/02 705/7.32 |
| 8,019,049 B2 | 9/2011 | Allen, Jr. et al. | |
| 8,495,583 B2 | 7/2013 | Bassin et al. | |
| 8,595,750 B2 | 11/2013 | Agarwal et al. | |
| 8,756,460 B2 | 6/2014 | Blue et al. | |
| 8,866,818 B2 | 10/2014 | Rubin et al. | |
| 9,218,271 B2 | 12/2015 | Segall et al. | |
| 9,529,700 B2 | 12/2016 | Raghavan et al. | |
| 10,152,458 B1 * | 12/2018 | Stepaniants | G06F 17/18 |
| 2003/0233600 A1 | 12/2003 | Hartman et al. | |
| 2005/0055193 A1 * | 3/2005 | Bondarenko | G16B 50/00 703/22 |
| 2005/0261953 A1 * | 11/2005 | Malek | G06Q 30/02 705/7.32 |
| 2008/0256392 A1 | 10/2008 | Garland et al. | |
| 2009/0292180 A1 | 11/2009 | Mirow | |
| 2010/0030521 A1 | 2/2010 | Akhrarov et al. | |
| 2010/0169853 A1 | 7/2010 | Jain et al. | |
| 2011/0184896 A1 * | 7/2011 | Guyon | G06K 9/6231 706/12 |
| 2012/0084043 A1 | 4/2012 | Courtade et al. | |
| 2015/0213631 A1 | 7/2015 | Vander Broek | |
| 2015/0309918 A1 | 10/2015 | Raghavan et al. | |
| 2016/0012152 A1 | 1/2016 | Johnson et al. | |
| 2016/0253311 A1 * | 9/2016 | Xu | H04L 67/02 715/256 |
| 2016/0253466 A1 | 9/2016 | Agaian et al. | |
| 2016/0299836 A1 | 10/2016 | Kuhn et al. | |
| 2017/0103013 A1 | 4/2017 | Grechanik | |
| 2017/0128838 A1 * | 5/2017 | Burge | A63F 13/31 |
| 2019/0236479 A1 * | 8/2019 | Wagner | G06N 20/00 |

OTHER PUBLICATIONS

"Reliable Effects Screening: A Distributed Continuous Quality Assurance Process for Monitoring Performance Degradation in Evolving Software Systems", by C. Yilmaz et al., IEEE Trans. on Software Eng., Feb. 2007, vol. 33, No. 2, pp. 124-141. (Year: 2007).*
Chadjiconstantinidis, S. et al., "A construction method of new D-, A-optimal weighing designs when n E ≡ 3 mod 4 and k ≤ n - 1", Discrete Mathematics, 1994, pp. 39-50, vol. 131.
Chadjipantelis, T. et al., "Supplementary Difference Sets and D-Optimal Designs for n=2 mod 4", Discrete Mathematics, 1985, pp. 211-216, vol. 57.
Chadjipantelis, T. et al., "Construction of D-Optimal Designs for N=2 mod 4 Using Block-Circulant Matrices", Journal of Combinatorial Theory, Series A 40, 1985, pp. 125-135.
Chadjipantelis, T. et al., "The maximum determinant of 21x21(+1,-1)-matrices and d-optimal designs", Journal of Statistical Planning and Inference, 1987, pp. 167-178, vol. 16.
Cheng, C., "Optimality of some weighing and 2n fractional factorial designs", The Annals of Statistics, 1980, pp. 436-446, vol. 8, No. 2.
Cohn, J., "On determinants with elements ±1,II", Bulletin of the London Mathematical Society, 1989, pp. 36-42, vol. 21.
Cohn, J., "Almost D-optimal designs", Utilitas Mathematica, 2000, pp. 121-128, vol. 57.
Cuervo, D. et al., "Optimal design of large-scale screening experiments—A critical look at the coordinate-exchange algorithm", Statistics and Computing, 2016, pp. 15-28, vol. 26.
Deng, L. et al., "Generalized resolution and minimum aberration criteria for Plackett-Burman and other nonregular factorial designs", Statistica Sinica, 1999, pp. 1071-1082, vol. 9.
Dokovic, D., "Some new D-optimal designs", Australasian Journal of Combinatorics, 1997, pp. 221-231, vol. 15.
Dokovic, D., et al., "New results on D-optimal matrices", Journal of Combinatorial Designs, 2012, pp. 278-289, vol. 20.
Dokovic, D. et al., "D-optimal matrices of orders 118, 138, 150, 154, and 17", Algebraic Design Theory and Hadamard Matrices, 2015, pp. 72-82, vol. 133 of Springer Proceedings in Mathematics & Statistics.
Farmakis, N. et al.,"The Excess of Hadamard Matrices and Optimal Designs", Discrete Mathematics, 1987, pp. 165-176, vol. 67.
Farmakis, N., et al., "Two new D-optimal designs (83, 56, 12), (83, 55, 12)", Journal of Statistical Planning and Inference, 1987, pp. 247-257, vol. 15.
Fletcher, R. et al., "New D-optimal designs of order 110", Australasian Journal of Combinatorics, 2001, pp. 49-52, vol. 23.
Galil, Z. et al., "Construction Methods for D-Optimum Weighing Designs When n=3 mod 4", The Annals of Statistics, 1982, pp. 502-510, vol. 10.
Goethals, J. et al., "Orthogonal matrices with zero diagonal", Canadian Journal of Mathematics, 1967, pp. 1001-1010, vol. 19.
Horadam, K., "Hadamard matrices and their applications", Princeton University Press, 2012, pp. 1-278.
Jones, B. et al., "Partial replication of small two-level factorial designs", Quality Engineering, 2017, pp. 190-195, vol. 29.
Kharaghani, H., "A Construction of D-Optimal Designs for N=2 mod 4", Journal of Combinatorial Theory, 1987, pp. 156-158, vol. 46.
Koukouvinos, C. et al., "Supplementary difference sets and optimal designs.", Discrete Mathematics, 1991, pp. 49-58, vol. 88.
Kounias, S. et al., "Some D-optimal weighing designs for n ≡ 3(mod 4)", Journal of Statistical Planning and Inference, 1983, pp. 117-127, vol. 8.
Kounias, S. et al., "A construction of D-optimal weighing designs when n ≡ 3 mod 4", Journal of Statistical Planning and Inference, 1984, pp. 177-187, vol. 10.
Kounias, S. et al., "The Non-equivalent Circulant D-Optimal Designs for . . . n=66", Journal of Combinational Theory, 1994, pp. 26-38, Series A 65.
Kuhfeld, W. et al., "Large factorial designs for product engineering and marketing research applications", Technometrics, 2005, pp. 132-141, vol. 47, No. 2.
London, S., "Constructing New Turyn Type Sequences, T-Sequences and Hadamard Matrices", Ph.D. Thesis, 2013, pp. 1-63.
Meyer, R. et al., "The Coordinate-Exchange Algorithm for constructing exact optimal experimental designs", Technometrics, 1995, pp. 60-69, vol. 37, No. 1.
Moyssiadis, C. et al., "The exact D-optimal first order saturated design with 17 observations", Journal of Statistical Planning and Inference, 1982, pp. 13-27, vol. 7.
Paley, R., "On orthogonal matrices", Journal of Mathematics and Physics, 1933, pp. 311-320, vol. 12.
Payne, S., "On Maximizing Det(AT A)", Discrete Mathematics, 1974, pp. 145-158, vol. 10.
Plackett, R. et al., "The design of optimum multifactorial experiments", Biometrika, 1946, pp. 305-325, vol. 33.
Raghavarao, D., "Some Optimum Weighing Designs", Annals of Mathematical Statistics, 1959, pp. 295-303, vol. 30.

(56) References Cited

OTHER PUBLICATIONS

Sathe, Y. et al., "Construction Method for Some A- and D-Optimal Weighing Designs When N=3 (mod 4)", Journal of Statistical Planning and Inference, 1990, pp. 369-375, vol. 24.

Seberry, J. et al., "Hadamard matrices, sequences, and block designs", Contemporary Design Theory—A Collection of Surveys, 1992, pp. 431-560, John Wiley and Sons.

Smith, W., "Studies in Computational Geometry Motivated by Mesh Generation", PhD. Thesis Princeton University, 1988, pp. 1-496.

Orrick, W. et al., "Large-determinant sign matrices of order 4k+1", Discrete Mathematics, 2007, pp. 226-236, vol. 307.

Street, D. et al., "Partially Balanced Incomplete Block Designs", Handbook of Combinatorial Designs, 2007, pp. 562-565, 2nd Edition.

Sun, D., "Estimation capacity and related topics in experimental designs", A Thesis presented to the University of Waterloo, 1994, pp. 1-184.

Sylvester, J., "Thoughts on inverse orthogonal matrices, simultaneous sign successions, and tessellated pavements", Philosophical Magazine, 1867, pp. 461-475, vol. 34.

Wallis, J., "On supplementary difference sets", Aequationes Mathematicae, 1972, pp. 242-257, vol. 8.

Wallis, J. et al., "Some classes of Hadamard matrices with constant diagonal" Bulletin of the Australian Mathematical Society, 1972, pp. 233-249, vol. 7.

Williamson, J., "Determinants whose elements are 0 and 1", The American Mathematical Monthly, Oct. 1946, pp. 427-434, vol. 53, No. 8.

Williamson, J. et al., "Hadamard's determinant theorem and the sum of four squares", Duke Mathematical Journal, 1944, pp. 65-81, vol. 11, No. 1.

Xu, H. et al., "Generalized minimum aberration for asymmetrical fractional factorial designs", The Annals of Statistics, Aug. 2001, pp. 1066-1077, vol. 29, No. 4.

Indiana University, "The Hadamard maximal determinant problem", pp. 1-4, retrieved on Jul. 5, 2019, retrieved from internet http://www.indiana.edu/~maxdet/fullPage.shtml#tableTop.

Ehlich, H., "Determinant etsimates are binaries", Mathematische Zeitschrift, 1964, pp. 123-132, vol. 83, No. 2.

Ehlich, H., "Determinant for binaries with n = 3 mod 4", Mathematische Zeitschrift, 1964, pp. 438-447, vol. 84.

Kuhn et al. "Software Fault Interactions and Implications for Software Testing"; IEEE Transaction on Software Engineering; Jun. 2004; pp. 418-421; vol. 30, No. 6.

Bryce et al. "Prioritized interaction testing for pair-wise coverage with seeding and constraints"; Information and Software Technology; Feb. 27, 2006; pp. 960-970; vol. 48, No. 10.

Chandrasekaran et al. "Evaluating the effectiveness of BEN in localizing different types of software fault"; IEEE 9th International Conference on Software Testing, Verification and Validation Workshops; Apr. 10, 2016; pp. 1-31.

Colbourn et al. "Locating and Detecting Arrays for Interaction Faults"; Journal of Combinatorial Optimization; 2008; pp. 1-34; vol. 15, No. 1.

Dalal et al. "Factor-Covering Designs for Testing Software"; Technometrics; Aug. 1998; pp. 1-14; vol. 40, No. 3.

Demiroz et al. "Cost-Aware Combinatorial Interaction Testing"; Proc. of the International Conference on Advanaces in System Testing and Validation Lifecycles; 2012; pp. 1-8.

Elbaum et al. "Selecting a Cost-Effective Test Case Prioritization Technique"; Software Quality Journal; Apr. 20, 2004; pp. 1-26; vol. 12, No. 3.

Ghandehari et al. "Identifying Failure-Inducing Combinations in a Combinatorial Test Set"; IEEE Fifth International Conference on Software Testing, Verification and Validation; Apr. 2012; pp. 1-10.

Ghandehari et al. "Fault Localization Based on Failure-Inducing Combinations"; IEEE 24th International Symposium on Software Reliability Engineering; Nov. 2013; pp. 168-177.

Alan Hartman "Software and Hardware Testing Using Combinatorial Covering Suites"; The Final Draft; Jul. 3, 2018; pp. 1-41; IBM Haifa Research Laboratory.

Katona et al. "Two Applications (for Search Theory and Truth Functions) of Sperner Type Theorems"; Periodica Mathematica Hungarica; 1973; pp. 19-26; vol. 3, No. 1-2.

Cohen et al. "Interaction Testing of Highly-Configurable Systems in the Presence of Constraints"; ISSTA '07 London, England, United Kingdom; Jul. 9-12, 2007; pp. 1-11; ACM 978-1-59593-734-6/07/0007.

Cohen et al. "The Combinatorial Design Approach to Automatic Test Generation"; IEEE Software; Sep. 1996; pp. 83-88; vol. 13, No. 5.

Dunietz et al. "Applying Design of Experiments to Software Testing"; Proceedings of 19th ECSE, New York, NY; 1997; pp. 205-215; ACM, Inc.

Cohen et al. "The AETG System: An Approach to Testing Based on Combinatorial Design"; IEEE Transactions on Software Engineering; Jul. 1997; pp. 437-444; vol. 23, No. 7.

Joseph Morgan "Combinatorial Testing: An Approach to Systems and Software Testing Based on Covering Arrays"; Book—Analytic Methods in Systems and Software Testing; 2018; pp. 131-158; John Wiley & Sons Ltd.; Hoboken, NJ, US.

Cohen et al. "Constructing Interaction Test Suites for Highly-Configurable Systems in the Presence of Constraints: A Greedy Approach"; IEEE Transactions on Software Engineering; Sep./Oct. 2008; pp. 633-650; vol. 34, No. 5.

Colbourn et al. "Coverage, Location, Detection, and Measurement"; IEEE Ninth International Conference on Software Testing, Verification and Validation Workshops; Apr. 2016; pp. 19-25.

Kleitman et al. "Families of k-Independent Sets"; Discrete Mathematics; 1973; pp. 255-262; vol. 6, No. 3.

Johnson et al. "Largest Induced Subgraphs of the n-Cube That Contain No 4-Cycles"; Journal of Combinatorial Theory; 1989; pp. 346-355; Series B 46.

Dalal et al. "Model-Based Testing in Practice"; Proceedings of the 21st ICSE, New York, NY; 1999; pp. 1-10.

Moura et al. "Covering Arrays with Mixed Alphabet Sizes"; Journal of Combinatorial Design; 2003; pp. 413-432; vol. 11, No. 6.

Brownlie et al. "Robust Testing of AT&T PMX/StarMAIL Using OATS"; AT&T Technical Journal, May 1992; pp. 41-47; vol. 73, No. 3.

Robert Mandl "Orthogonal Latin Squares: An Application of Experiment Design to Compiler Testing"; Communications of the ACM; Oct. 1985; pp. 1054-1058; vol. 28, No 10.

Hartman et al. "Problems and algorithms for covering arrays"; Discrete Mathematics; 2004; pp. 149-156; vol. 284, No. 1-3.

Jang, D. et al., "Correlation-Based r-plot for Evaluating Supersaturated Designs", Qual. Reliab. Engng. Int., Mar. 11, 2013, pp. 503-512, John Wiley & Sons, Ltd.

Kim, Y. et al., "Graphical methods for evaluating covering arrays", Quality and Reliability Engineering International, Aug. 31, 2016, pp. 1-24, Los Alamos National Laboratory.

Taylor, W. et al., "A Structure Diagram Symbolization for Analysis of Variance", The American Statistician, May 1981, pp. 85-93, vol. 35, No. 2, Taylor & Francis, Ltd.

Iversen, P. et al., "Visualizing Experimental Designs for Balanced ANOVA Models using Lisp-Stat", Journal of Statistical Software, Feb. 2005, pp. 1-18, vol. 13, Issue 3.

Kay, P., "Why design experiments? Reason 2: Process understanding", JMP User Community/JMP Blog, May 1, 2018, pp. 1-10.

Angel M., "Conducting Experiments with Experiment Manager", Proceedings of the 1996 Winter Simulation Conference, 1996, pp. 535-541.

Ghanbari, M., "Visualization Overview", 2007 Thirty-Ninth Southeastern Symposium on System Theory, Mar. 4-6, 2007, pp. 133-137.

Yang, C., "Some designs of maximal (+1,-1) determinant of order n=2 mod 4", Mathematics of Computation, 1966, pp. 147-148, vol. 20.

Yang, C., "On Designs of Maximal (+1, -1)-Matrices of Order n=2 mod 4", Mathematics of Computation, 1968, pp. 174-180, vol. 22.

(56) References Cited

OTHER PUBLICATIONS

Yang, C., "On Designs of Maximal (+1, −1)-Matrices of Order n=2 mod 4", Mathematics of Computation, 1969, pp. 201-205, vol. 23, No. 105.
Yang, C., "Maximal binary matrices and sum of two squares", Mathematics of Computation, 1976, pp. 148-153, vol. 30, No. 133.

\* cited by examiner

|  | Factor a | Factor b | Factor c | Factor d | Factor e | Factor f |
|---|---|---|---|---|---|---|
| Level A | Weight = 1 | Weight= 1 | Weight= 1 | Weight= 1 | Weight=3 | Weight= 1 |
| Level B | Weight =2 | Weight= 1 | Weight= 1 | Weight=2 | Weight= 1 | Weight= 1 |

*FIG. 16C*

| Factor 1 (Level 1) | Factor 2 (Level 2) | Cause Indicator | Normalized Weight |
|---|---|---|---|
| a(A) | b(B) | 1 | 1/14 |
| a(A) | d(B) | 2 | 2/14=1/7 |
| b(B) | c(A) | 1 | 1/14 |
| c(A) | f(B) | 1 | 1/14 |
| d(B) | e(A) | 6 | 6/14=3/7 |
| e(A) | f(B) | 3 | 3/14 |

*FIG. 16D*

Test Case 4 Failed — 1720

1722 / 1724

| Factor 1 (Level 1) | Factor 2 (Level 2) | Combined Weight |
|---|---|---|
| c(B) | d(A) | 1 |
| a(A) | c(B) | 2 |
| a(A) | e(B) | 4 |
| b(A) | c(B) | 2 |
| b(A) | f(B) | 2 |
| d(A) | e(B) | 2 |
| d(A) | f(B) | 1 |

*FIG. 17C*

Test Case 5 Failed — 1730

1732 / 1734

| Factor 1 (Level 1) | Factor 2 (Level 2) | Combined Weight |
|---|---|---|
| c(B) | d(A) | 1 |
| a(B) | d(A) | 2 |
| a(B) | e(A) | 6 |
| b(B) | d(A) | 2 |
| b(B) | f(A) | 2 |
| c(B) | e(A) | 3 |
| c(B) | f(A) | 1 |

*FIG. 17D*

Test Case 4 Failed Taking Into Account Test Case 5

| Factor 1 (Level 1) | Factor 2 (Level 2) | Cause Indicator |
|---|---|---|
| c(B) | d(A) | 146/354 |
| a(A) | c(B) | 32/354 |
| a(A) | e(B) | 64/354 |
| b(A) | c(B) | 32/354 |
| b(A) | f(B) | 32/354 |
| d(A) | e(B) | 32/354 |
| d(A) | f(B) | 16/354 |

*FIG. 17E*

Test Case 5 Failed Taking Into Account Test Case 4

| Factor 1 (Level 1) | Factor 2 (Level 2) | Cause Indicator |
|---|---|---|
| c(B) | d(A) | 146/354 |
| a(B) | d(A) | 26/354 |
| a(B) | e(A) | 78/354 |
| b(B) | d(A) | 26/354 |
| b(B) | f(A) | 26/354 |
| c(B) | e(A) | 39/354 |
| c(B) | f(A) | 13/354 |

*FIG. 17F*

| Factor 1 (Level 1) | Factor 2 (Level 2) | Cause Indicator |
|---|---|---|
| c(B) | d(A) | 146/354 |
| a(B) | e(A) | 78/354 |
| a(A) | e(B) | 64/354 |
| c(B) | e(A) | 39/354 |
| a(A) | c(B) | 32/354 |
| b(A) | c(B) | 32/354 |
| b(A) | f(B) | 32/354 |
| d(A) | e(B) | 32/354 |
| a(B) | d(A) | 26/354 |
| b(B) | d(A) | 26/354 |
| b(B) | f(A) | 26/354 |
| d(A) | f(B) | 16/354 |
| c(B) | f(A) | 13/354 |

*FIG. 17G*

| Test Case | Result | Diagnostic Plot | DensityCurve | GoodnessOfFit | SaveFitQuant | SaveDensForm | SaveSpecLimit |
|---|---|---|---|---|---|---|---|
| 1 | Pass | unchecked | unchecked | unchecked | unchecked | unchecked | unchecked |
| 2 | Pass | checked | checked | checked | checked | checked | checked |
| 3 | Fail | checked | unchecked | checked | unchecked | checked | unchecked |
| 4 | Pass | checked | checked | unchecked | checked | unchecked | unchecked |
| 5 | Pass | unchecked | unchecked | unchecked | checked | checked | checked |
| 6 | Pass | unchecked | checked | checked | unchecked | unchecked | checked |

Summary
Success Runs 5
Failure Runs 1
Missing 0

Failure Analysis Details

2 Factor Interactions

| Factors | Failure Levels | Failure Count | Probabilities |
|---|---|---|---|
| SaveFitQuant, SaveDensForm | unchecked, checked | 1 | 0.429 |
| SaveDensForm, SaveSpecLimit | checked, unchecked | 1 | 0.214 |
| DiagnosticPlot, SaveFitQuant | checked, unchecked | 1 | 0.143 |
| DiagnosticPlot, DensityCurve | checked, unchecked | 1 | 0.071 |
| DensityCurve, GoodnessOfFit | unchecked, checked | 1 | 0.071 |
| GoodnessOfFit, SaveSpecLimit | checked, unchecked | 1 | 0.071 |

*FIG. 20E*

*Prior Art*
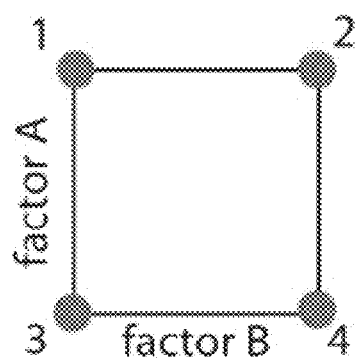
| trial | factor levels | |
|---|---|---|
| | A | B |
| 1 | + | − |
| 2 | + | + |
| 3 | − | − |
| 4 | − | + |
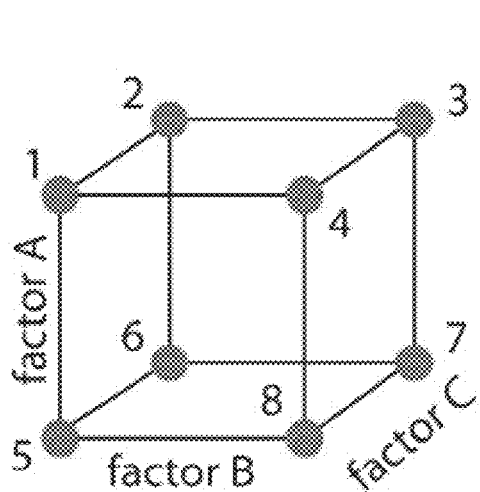
| trial | factor levels | | |
|---|---|---|---|
| | A | B | C |
| 1 | + | − | − |
| 2 | + | − | + |
| 3 | + | + | + |
| 4 | + | + | − |
| 5 | − | − | − |
| 6 | − | − | + |
| 7 | − | + | + |
| 8 | − | + | − |
*FIG. 28*

FIG. 29A

Interactive GUI 2910 — 2300

| Run 2321 | Feed Rate 2322 | Catalyst 2323 | Stir Rate 2324 | Temperature 2325 | Concentration 2326 |
|---|---|---|---|---|---|
| 7 | 1 | -1 | 1 | -1 | -1 |

2320

| Design Metrics | Current Design 2920 | Saved Design 2922 | Original Design 2924 |
|---|---|---|---|
| D-Efficiency 2932 | 0.84158 | 0.84158 | 0.84158 |
| A-Efficiency 2934 | 0.66496 | 0.66496 | 0.66496 |

2900

2940 Save Current Design    2944 Revert to Saved Design
2942 Make Design    2946 Revert to Original Design

FIG. 29B

Interactive GUI 2910 — 2300

| Run 2321 | Feed Rate 2322 | Catalyst 2323 | Stir Rate 2324 | Temperature 2325 | Concentration 2326 |
|---|---|---|---|---|---|
| 7 | -1 | -1 | 1 | -1 | -1 |

2320

| Design Metrics | Current Design 2920 | Saved Design 2922 | Original Design 2924 |
|---|---|---|---|
| D-Efficiency 2932 | 0.87041 | 0.84158 | 0.84158 |
| A-Efficiency 2934 | 0.7355 | 0.66496 | 0.66496 |

2900

2940 Save Current Design    2944 Revert to Saved Design
2942 Make Design    2946 Revert to Original Design

| Run 3220 | X1 3201 | X2 3202 | X3 3203 | X4 3204 | X5 3205 | X6 3206 | X7 3208 | Do Not Care 3210 |
|---|---|---|---|---|---|---|---|---|
| 1 | -1 | 1 | -1 | -1 | 1 | -1 | 1 | |
| 2 | -1 ✓ | 1 ✓ | -1 ✓ | 1 ✓ | 1 ✓ | -1 ✓ | 1 ✓ | ✓ |
| 3 | -1 | 1 | 1 | 1 | -1 | 1 | -1 | |
| 4 | -1 | -1 | -1 | -1 | -1 | -1 | -1 | |
| 5 | 1 | -1 | 1 | 1 | 1 | -1 | 1 | |
| 6 | -1 | -1 | 1 | -1 | 1 | 1 | -1 | |
| 7 | -1 | 1 | 1 | 1 | -1 | 1 | 1 | |
| 8 | 1 | 1 | -1 | -1 | 1 | -1 | -1 | |
| 9 | -1 | 1 | 1 | -1 | 1 | 1 | 1 | |
| 10 | 1 | -1 | 1 | -1 | -1 | 1 | 1 | |
| 11 | 1 | 1 | 1 | -1 | -1 | -1 | 1 | |
| 12 | 1 | -1 | -1 | 1 | -1 | -1 | -1 | |
| 13 | 1 | 1 | -1 | 1 | -1 | -1 | 1 | |
| 14 | 1 ✓ | 1 ✓ | 1 ✓ | 1 ✓ | 1 ✓ | 1 ✓ | 1 ✓ | ✓ |
| 15 | 1 ✓ | 1 ✓ | 1 ✓ | 1 ✓ | 1 ✓ | 1 ✓ | 1 ✓ | ✓ |
| 16 | 1 ✓ | 1 ✓ | 1 ✓ | 1 ✓ | 1 ✓ | 1 ✓ | 1 ✓ | ✓ |

GUI 3230

FIG. 32A

| Design Metrics | Current Design 3241 | Saved Design 3243 | Original Design 3245 |
|---|---|---|---|
| 3-Coverage 3242 | 1 | 1 | 1 |
| 4 Coverage 3244 | 0.78929 | 0.7125 | .7125 |

FIG. 32B $$3801 \begin{bmatrix} 1 & 1 & 1 & 1 & 1 & 1 & 1 & 1 & -1 & -1 & -1 \\ 1 & -1 & 1 & 1 & -1 & 1 & 1 & -1 & 1 & -1 & -1 \\ 1 & 1 & -1 & 1 & 1 & -1 & -1 & -1 & -1 & -1 & -1 \\ 1 & 1 & 1 & 1 & 1 & -1 & -1 & -1 & 1 & 1 & 1 \\ 1 & -1 & 1 & 1 & -1 & -1 & -1 & 1 & -1 & 1 & 1 \\ 1 & 1 & -1 & -1 & 1 & -1 & 1 & 1 & 1 & -1 & 1 \\ 1 & 1 & -1 & -1 & -1 & -1 & 1 & 1 & 1 & 1 & -1 \\ 1 & -1 & -1 & -1 & 1 & 1 & 1 & -1 & -1 & 1 & 1 \\ 1 & -1 & 1 & -1 & 1 & -1 & -1 & 1 & 1 & -1 & -1 \\ 1 & 1 & 1 & -1 & -1 & 1 & -1 & -1 & -1 & 1 & -1 \\ 1 & 1 & 1 & -1 & -1 & -1 & 1 & -1 & -1 & -1 & 1 \end{bmatrix}$$

$$3803 \begin{bmatrix} 1 & -1 & -1 & -1 & -1 & 1 & 1 & 1 & 1 & 1 & 1 \\ 1 & 1 & 1 & 1 & 1 & -1 & 1 & -1 & 1 & -1 & 1 \\ 1 & 1 & 1 & 1 & 1 & -1 & 1 & 1 & -1 & 1 & -1 \\ 1 & 1 & 1 & 1 & 1 & -1 & -1 & 1 & 1 & -1 \\ 1 & 1 & 1 & 1 & 1 & -1 & 1 & -1 & -1 & 1 \\ 1 & 1 & 1 & -1 & -1 & 1 & 1 & -1 & -1 & -1 & -1 \\ 1 & -1 & -1 & 1 & 1 & 1 & 1 & -1 & -1 & -1 & -1 \\ 1 & 1 & -1 & 1 & -1 & -1 & -1 & 1 & 1 & -1 & -1 \\ 1 & -1 & 1 & -1 & 1 & -1 & -1 & 1 & 1 & -1 & -1 \\ 1 & 1 & -1 & -1 & 1 & -1 & -1 & -1 & -1 & 1 & 1 \\ 1 & -1 & 1 & 1 & -1 & -1 & -1 & -1 & -1 & 1 & 1 \end{bmatrix}$$

$$3802 \begin{bmatrix} 1 & 1 & 1 & 1 & -1 & -1 & 1 & 1 & -1 & -1 & -1 \\ 1 & 1 & 1 & 1 & -1 & 1 & -1 & -1 & 1 & -1 & -1 \\ 1 & 1 & 1 & -1 & 1 & -1 & -1 & -1 & -1 & -1 & -1 \\ 1 & 1 & -1 & 1 & 1 & -1 & -1 & -1 & -1 & 1 & 1 \\ 1 & 1 & -1 & -1 & 1 & 1 & 1 & 1 & 1 & -1 & -1 \\ 1 & -1 & 1 & 1 & 1 & 1 & -1 & -1 & -1 & 1 \\ 1 & -1 & -1 & -1 & -1 & -1 & 1 & 1 & -1 & 1 \\ 1 & -1 & -1 & -1 & -1 & 1 & 1 & -1 & -1 & 1 & -1 \\ 1 & -1 & 1 & 1 & 1 & -1 & 1 & 1 & 1 & -1 \\ 1 & 1 & 1 & -1 & -1 & -1 & 1 & -1 & 1 & 1 & 1 \\ 1 & 1 & 1 & -1 & -1 & 1 & -1 & 1 & -1 & 1 & 1 \end{bmatrix}$$

OPTIMAL SCREENING DESIGNS

RELATED APPLICATIONS

This application claims the benefit of U.S. Provisional Application No. 62/796,214, filed Jan. 24, 2019, U.S. Provisional Application No. 62/807,286 filed Feb. 19, 2019, and U.S. Provisional Application No. 62/816,150 filed Mar. 10, 2019, and is a continuation-in-part of U.S. application Ser. No. 16/240,182, filed Jan. 4, 2019, which claims the benefit of U.S. Provisional Application No. 62/728,361 filed Sep. 7, 2018, and which is a continuation-in-part of U.S. application Ser. No. 16/154,290, filed Oct. 8, 2018, which issued as U.S. Pat. No. 10,338,993 on Jul. 2, 2019, which claims the benefit of U.S. Provisional Application No. 62/702,247 filed Jul. 23, 2018, and claims the benefit of U.S. Provisional Application No. 62/661,057, filed Apr. 22, 2018. The disclosures of each of these applications are incorporated herein by reference in their entirety.

BACKGROUND

In a complex system, different components work together to function as the complex system. For example, an airplane may have electrical, mechanical and software components that work together for the airplane to land. An engineer may have different options for a given component in the system (e.g., different control systems or different settings for a control system for the landing gear of the airplane). An engineer testing a complex system can construct a test suite that represents different test cases for the system with selections for the different options for each of the components in the system. The test suite can be referred to as a combinatorial test suite in that it tests different combinations of configurable options for a complex system. If there are failures, the test engineer is faced with the task of identifying the option or combination of options that precipitated the failures (e.g., from a table of entries or summary statistics). When there are multiple components in the complex system, it can be difficult to visualize different options for each component and the results of testing those different options. An engineer may design an experiment with test cases each test case specifying one of different options for each factor of the experiment (e.g., to test a complex system). A screening design, for instance, is useful for determining which active factors in the experiment effect the outcome.

SUMMARY

In an example embodiment, a computer-program product tangibly embodied in a non-transitory machine-readable storage medium is provided. The computer-program product includes instructions to cause a computing device to output an indication of the updated screening design for the output design of the experiment. The computing device obtains a metric N indicating a quantity of a plurality of test cases for an output design of an experiment Each element of a test case of the output design is a test condition for testing one of factors for the experiment. A test condition comprises one of different options for a given factor of the experiment. The computing device obtains input indicating a quantity p of an indicated plurality of factors for the output design. The computing device determines whether there are stored instructions for generating an initial screening design for the experiment. The initial screening design is for identifying one or more active factors of the experiment each of which independently affect an outcome of a given test case of the experiment. The computing device responsive to determining that there are stored instructions for generating the initial screening design for the experiment, selects, using the stored instructions, the initial screening design for the experiment. The computing device obtains a primary criterion and a secondary criterion for scoring the output design. The secondary criterion is different from the primary criterion. The computing device evaluates the initial screening design by determining an initial score for the primary criterion for the initial screening design. The initial score indicates an efficiency of the initial screening design at identifying the one or more active factors. The computing device determines whether to modify the initial screening design based on modification criteria comprising one or more of the secondary criterion, the metric N, and the quantity p. The computing device responsive to determining, based on the modification criteria, to modify the initial screening design, generates an updated screening design for the initial screening design by (1) generating one or more modified screening designs that each has at least one option for a corresponding test case different from the initial screening design; (2) evaluating the one or more modified screening designs by computing a respective score for the primary criterion for each of the one or more modified screening designs; (3) determining that each of the one or more modified screening designs satisfies the primary criterion by respectively comparing the respective score for the primary criterion to the initial score for the primary criterion or a threshold score for the primary criterion; (4) computing a score for the secondary criterion for a given design of the one or more modified screening designs; and (5) selecting, based on the score for the secondary criterion, a given design of the one or more modified screening designs as the updated screening design. The computing device outputs an indication of the updated screening design for the output design of the experiment.

In another example embodiment, a computing device is provided. The computing device includes, but is not limited to, a processor and memory. The memory contains instructions that when executed by the processor control the computing device to output an indication of the updated screening design for an output design of an experiment.

In another example embodiment, a method of outputting an indication of the updated screening design for an output design of an experiment is provided.

Other features and aspects of example embodiments are presented below in the Detailed Description when read in connection with the drawings presented with this application.

BRIEF DESCRIPTION OF THE DRAWINGS

FIG. 16C illustrates an example set of input weights with default input weights in at least one embodiment of the present technology.

FIG. 16D illustrates example cause indicators in at least one embodiment of the present technology.

FIGS. 17C-17D illustrate an example combined weight for each test condition of failed tests in at least one embodiment of the present technology.

FIGS. 17E-17F illustrate example cause indicators taking into account multiple failed test outcomes in at least one embodiment of the present technology.

FIG. 17G illustrates an example ordered ranking of cause indicators in at least one embodiment of the present technology.

FIG. 20C illustrates an example failure indication in at least one embodiment of the present technology.

FIGS. 20D-20E illustrate an example graphical user interface for displaying a most likely potential cause for a potential failure in at least one embodiment of the present technology.

FIG. 28 illustrates a prior art technique of a three dimensional visualization of factors.

FIGS. 29A-29B illustrate an example interactive graphical user interface with design metric evaluation in at least one embodiment of the present technology.

FIGS. 30A-30D illustrate example graphical representations of results of an experiment in at least one embodiment of the present technology.

FIGS. 31A-31B illustrate example graphical representations for diagnosing covering arrays in at least one embodiment of the present technology.

FIGS. 32A-32D illustrate an example interactive graphical user interface for controlling do not care cells in at least one embodiment of the present technology.

FIG. 38 illustrates an example initial screening design and modified screening designs in one or more embodiments.

DETAILED DESCRIPTION

In the following description, for the purposes of explanation, specific details are set forth in order to provide a thorough understanding of embodiments of the technology. However, it will be apparent that various embodiments may be practiced without these specific details. The figures and description are not intended to be restrictive.

The ensuing description provides example embodiments only, and is not intended to limit the scope, applicability, or configuration of the disclosure. Rather, the ensuing description of the example embodiments will provide those skilled in the art with an enabling description for implementing an example embodiment. It should be understood that various changes may be made in the function and arrangement of elements without departing from the spirit and scope of the technology as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional operations not included in a figure. A process may correspond to a method, a function, a procedure, a subroutine, a subprogram, etc. When a process corresponds to a function, its termination can correspond to a return of the function to the calling function or the main function.

Systems depicted in some of the figures may be provided in various configurations. In some embodiments, the systems may be configured as a distributed system where one or more components of the system are distributed across one or more networks in a cloud computing system.

Figure 1:
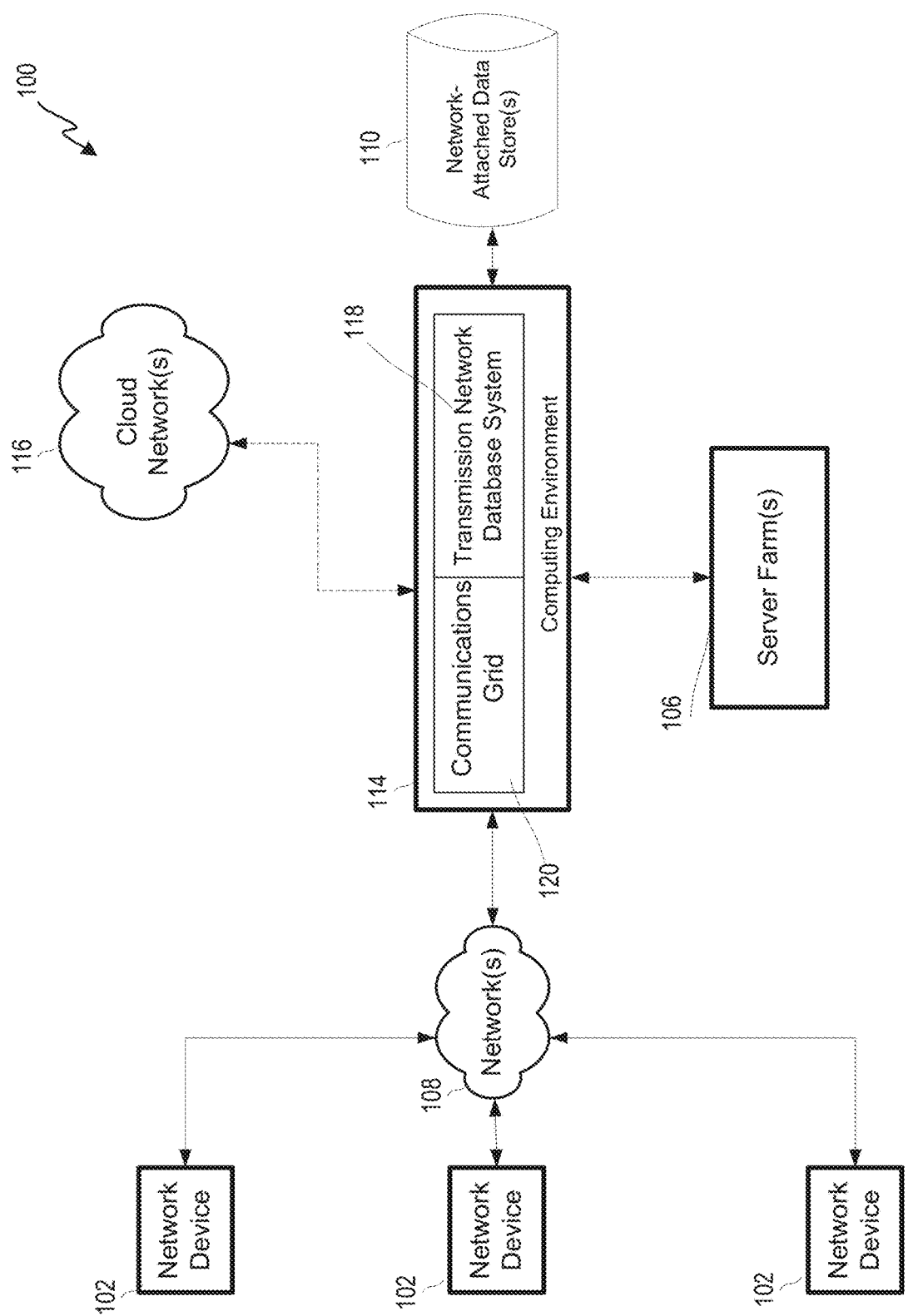
FIG. 1 illustrates a block diagram that provides an illustration of the hardware components of a computing system, according to at least one embodiment of the present technology.

FIG. 1 is a block diagram that provides an illustration of the hardware components of a data transmission network 100, according to embodiments of the present technology. Data transmission network 100 is a specialized computer system that may be used for processing large amounts of data where a large number of computer processing cycles are required.

Data transmission network 100 may also include computing environment 114. Computing environment 114 may be a specialized computer or other machine that processes the data received within the data transmission network 100. Data transmission network 100 also includes one or more network devices 102. Network devices 102 may include client devices that attempt to communicate with computing environment 114. For example, network devices 102 may send data to the computing environment 114 to be processed, may send signals to the computing environment 114 to control different aspects of the computing environment or the data it is processing, among other reasons. Network devices 102 may interact with the computing environment 114 through a number of ways, such as, for example, over one or more networks 108. As shown in FIG. 1, computing environment 114 may include one or more other systems. For example, computing environment 114 may include a database system 118 and/or a communications grid 120.

Figure 8:
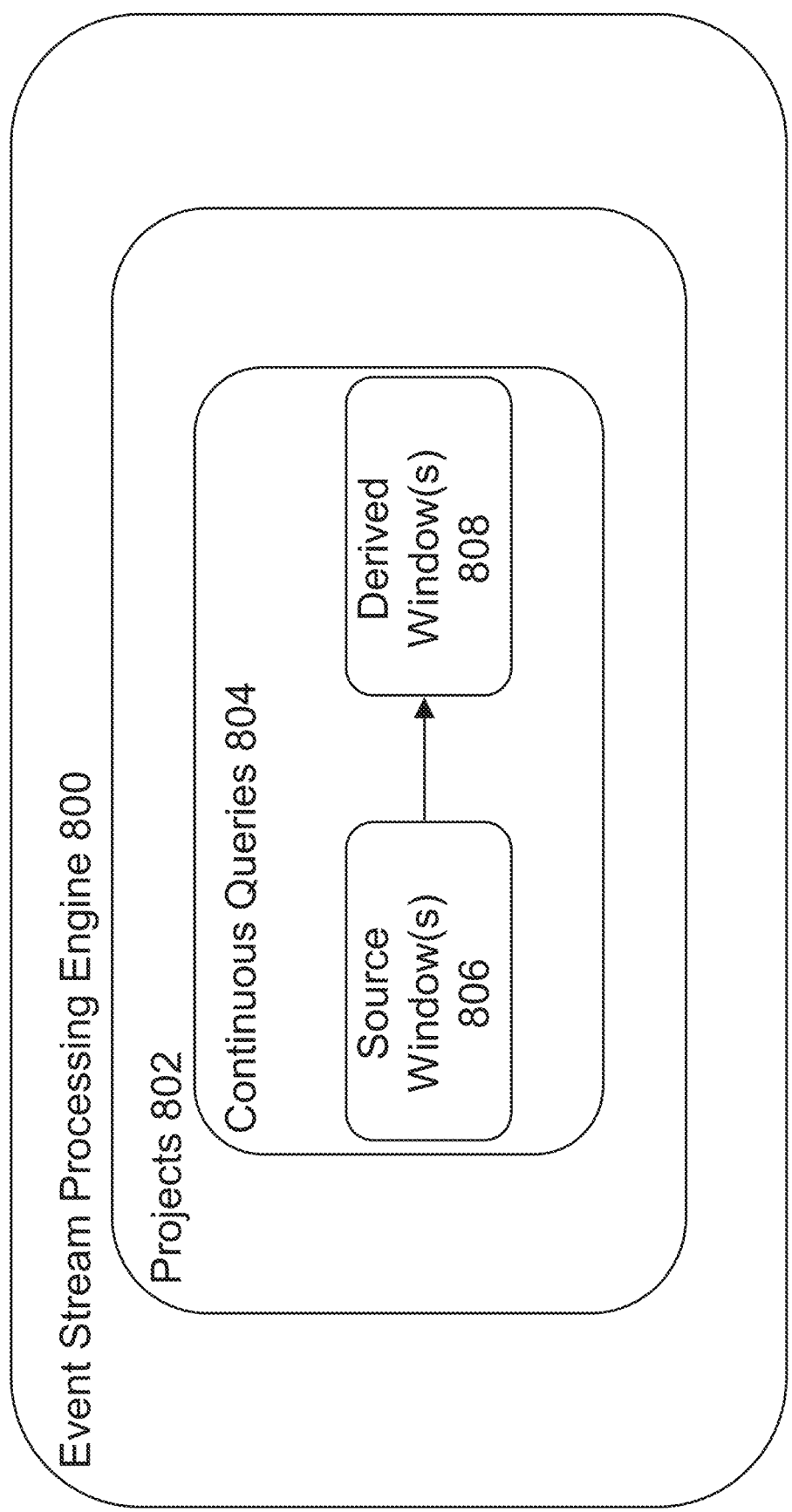
FIG. 8 illustrates a block diagram including components of an Event Stream Processing Engine (ESPE), according to at least one embodiment of the present technology.
Figure 9:
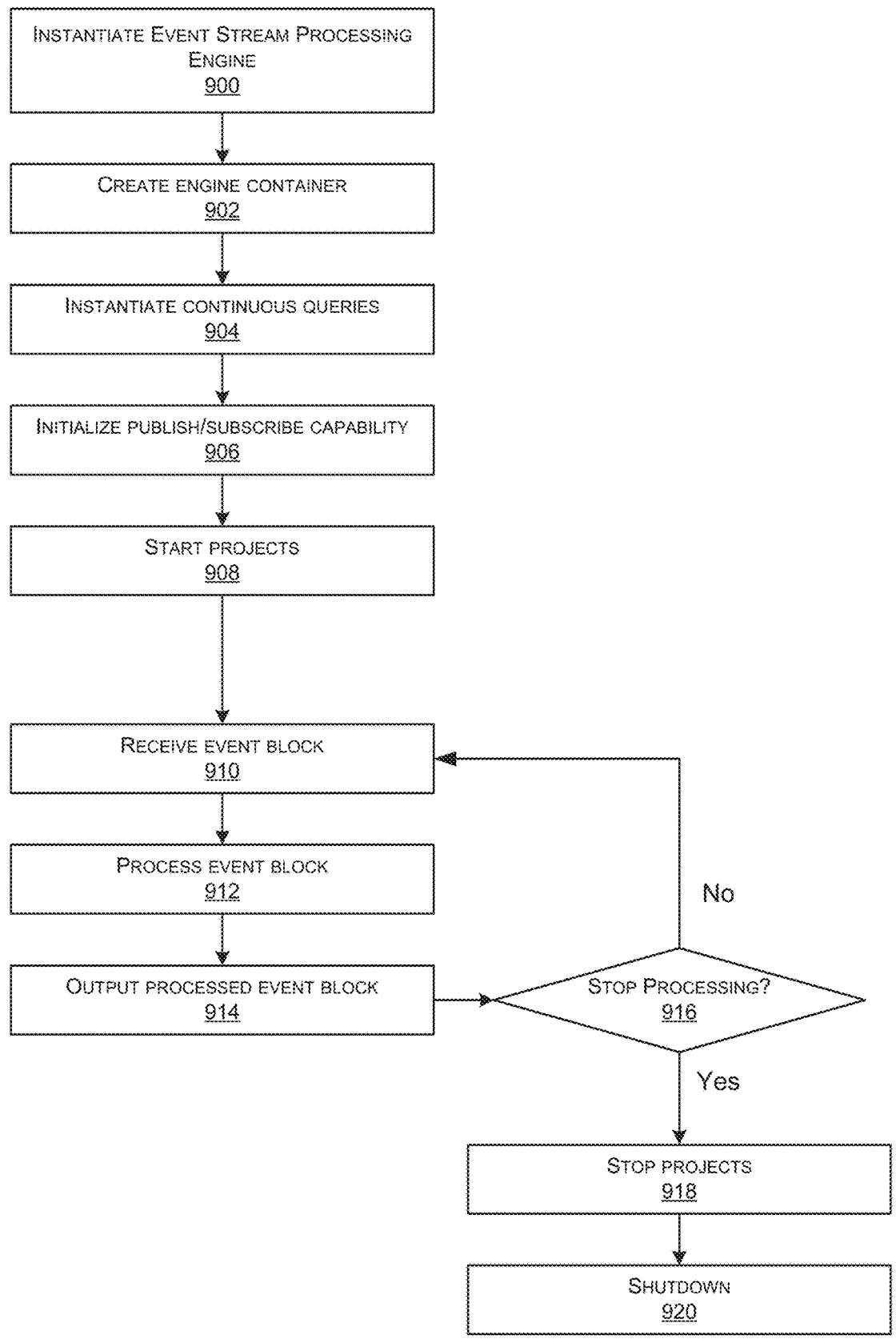
FIG. 9 illustrates a flow chart showing an example process including operations performed by an event stream processing engine, according to at least one embodiment of the present technology.
Figure 10:
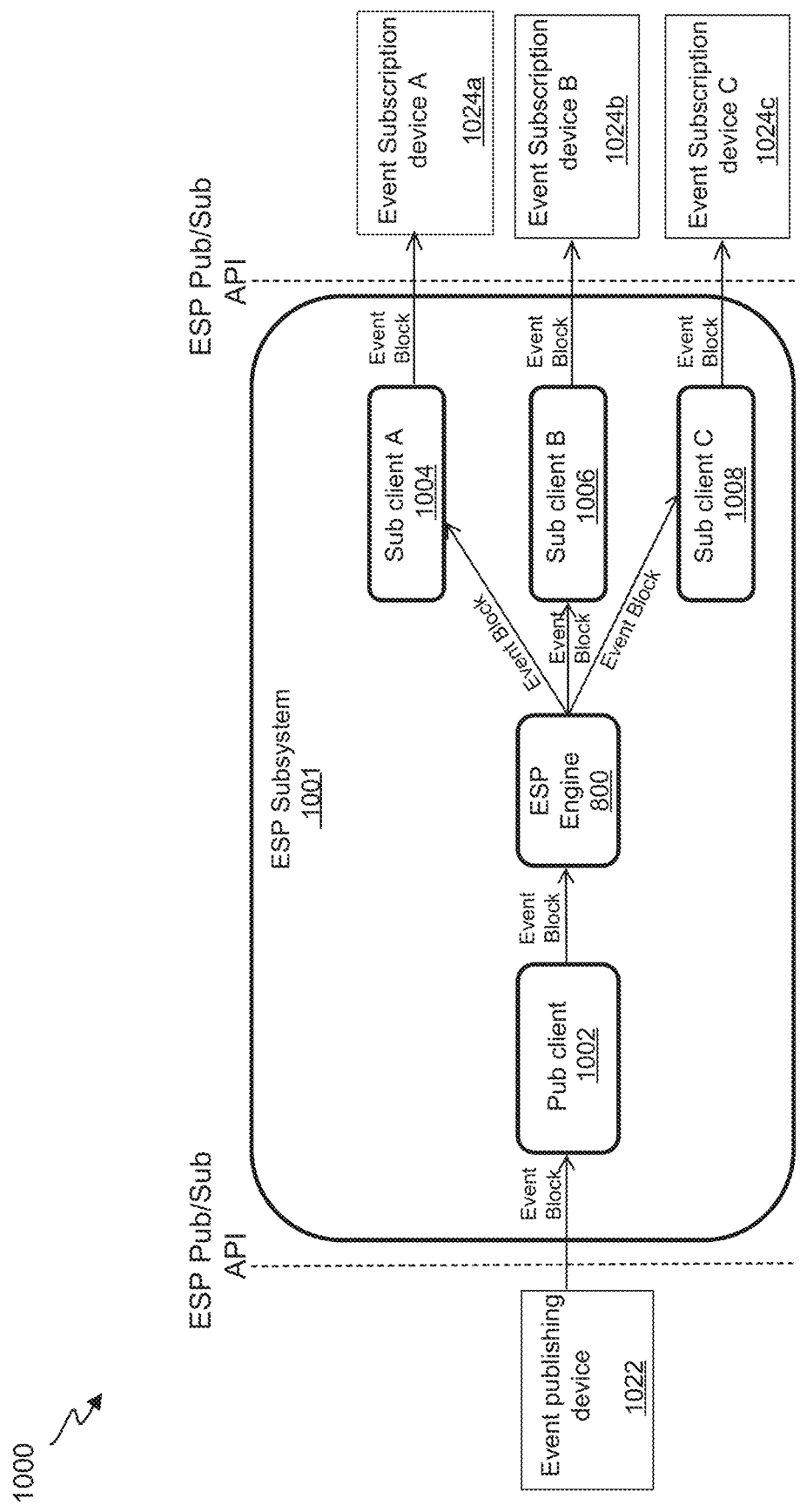
FIG. 10 illustrates an ESP system interfacing between a publishing device and multiple event subscribing devices, according to at least one embodiment of the present technology.

In other embodiments, network devices may provide a large amount of data, either all at once or streaming over a period of time (e.g., using event stream processing (ESP), described further with respect to FIGS. 8-10), to the computing environment 114 via networks 108. For example, network devices 102 may include network computers, sensors, databases, or other devices that may transmit or otherwise provide data to computing environment 114. For example, network devices may include local area network devices, such as routers, hubs, switches, or other computer networking devices. These devices may provide a variety of stored or generated data, such as network data or data specific to the network devices themselves. Network devices may also include sensors that monitor their environment or other devices to collect data regarding that environment or those devices, and such network devices may provide data they collect over time. Network devices may also include devices within the internet of things, such as devices within a home automation network. Some of these devices may be referred to as edge devices, and may involve edge computing circuitry. Data may be transmitted by network devices directly to computing environment 114 or to network-attached data stores, such as network-attached data stores 110 for storage so that the data may be retrieved later by the computing environment 114 or other portions of data transmission network 100.

Data transmission network 100 may also include one or more network-attached data stores 110. Network-attached data stores 110 are used to store data to be processed by the computing environment 114 as well as any intermediate or final data generated by the computing system in non-volatile memory. However in certain embodiments, the configuration of the computing environment 114 allows its operations to be performed such that intermediate and final data results can be stored solely in volatile memory (e.g., RAM), without a requirement that intermediate or final data results be stored to non-volatile types of memory (e.g., disk). This can be useful in certain situations, such as when the computing environment 114 receives ad hoc queries from a user and when responses, which are generated by processing large amounts of data, need to be generated on-the-fly. In this non-limiting situation, the computing environment 114 may be configured to retain the processed information within memory so that responses can be generated for the user at different levels of detail as well as allow a user to interactively query against this information.

Network-attached data stores may store a variety of different types of data organized in a variety of different ways and from a variety of different sources. For example, network-attached data storage may include storage other than primary storage located within computing environment 114 that is directly accessible by processors located therein. Network-attached data storage may include secondary, tertiary or auxiliary storage, such as large hard drives, servers, virtual memory, among other types. Storage devices may include portable or non-portable storage devices, optical storage devices, and various other mediums capable of storing, containing data. A machine-readable storage medium or computer-readable storage medium may include a non-transitory medium in which data can be stored and that does not include carrier waves and/or transitory electronic signals. Examples of a non-transitory medium may include, for example, a magnetic disk or tape, optical storage media such as compact disk or digital versatile disk, flash memory, memory or memory devices. A computer-program product may include code and/or machine-executable instructions that may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, among others. Furthermore, the data stores may hold a variety of different types of data. For example, network-attached data stores 110 may hold unstructured (e.g., raw) data, such as manufacturing data (e.g., a database containing records identifying products being manufactured with parameter data for each product, such as colors and models) or product sales databases (e.g., a database containing individual data records identifying details of individual product sales).

The unstructured data may be presented to the computing environment 114 in different forms such as a flat file or a conglomerate of data records, and may have data values and accompanying time stamps. The computing environment 114 may be used to analyze the unstructured data in a variety of ways to determine the best way to structure (e.g., hierarchically) that data, such that the structured data is tailored to a type of further analysis that a user wishes to perform on the data. For example, after being processed, the unstructured time stamped data may be aggregated by time (e.g., into daily time period units) to generate time series data and/or structured hierarchically according to one or more dimensions (e.g., parameters, attributes, and/or variables). For example, data may be stored in a hierarchical data structure, such as a ROLAP OR MOLAP database, or may be stored in another tabular form, such as in a flat-hierarchy form.

Data transmission network 100 may also include one or more server farms 106. Computing environment 114 may route select communications or data to the one or more sever farms 106 or one or more servers within the server farms. Server farms 106 can be configured to provide information in a predetermined manner. For example, server farms 106 may access data to transmit in response to a communication. Server farms 106 may be separately housed from each other device within data transmission network 100, such as computing environment 114, and/or may be part of a device or system.

Server farms 106 may host a variety of different types of data processing as part of data transmission network 100. Server farms 106 may receive a variety of different data from network devices, from computing environment 114, from cloud network 116, or from other sources. The data may have been obtained or collected from one or more sensors, as inputs from a control database, or may have been received as inputs from an external system or device. Server farms 106 may assist in processing the data by turning raw data into processed data based on one or more rules implemented by the server farms. For example, sensor data may be analyzed to determine changes in an environment over time or in real-time.

Data transmission network 100 may also include one or more cloud networks 116. Cloud network 116 may include a cloud infrastructure system that provides cloud services. In certain embodiments, services provided by the cloud network 116 may include a host of services that are made available to users of the cloud infrastructure system on demand. Cloud network 116 is shown in FIG. 1 as being connected to computing environment 114 (and therefore having computing environment 114 as its client or user), but cloud network 116 may be connected to or utilized by any of the devices in FIG. 1. Services provided by the cloud network can dynamically scale to meet the needs of its users. The cloud network 116 may include one or more computers, servers, and/or systems. In some embodiments, the computers, servers, and/or systems that make up the cloud network 116 are different from the user's own on-premises computers, servers, and/or systems. For example, the cloud network 116 may host an application, and a user may, via a communication network such as the Internet, on demand, order and use the application.

While each device, server and system in FIG. 1 is shown as a single device, it will be appreciated that multiple devices may instead be used. For example, a set of network devices can be used to transmit various communications from a single user, or remote server 140 may include a server stack. As another example, data may be processed as part of computing environment 114.

Each communication within data transmission network 100 (e.g., between client devices, between a device and connection management system 150, between servers 106 and computing environment 114 or between a server and a device) may occur over one or more networks 108. Networks 108 may include one or more of a variety of different types of networks, including a wireless network, a wired network, or a combination of a wired and wireless network. Examples of suitable networks include the Internet, a personal area network, a local area network (LAN), a wide area network (WAN), or a wireless local area network (WLAN). A wireless network may include a wireless interface or combination of wireless interfaces. As an example, a network in the one or more networks 108 may include a short-range communication channel, such as a Bluetooth or a Bluetooth Low Energy channel. A wired network may include a wired interface. The wired and/or wireless networks may be implemented using routers, access points, bridges, gateways, or the like, to connect devices in the network 114, as will be further described with respect to FIG. 2. The one or more networks 108 can be incorporated entirely within or can include an intranet, an extranet, or a combination thereof. In one embodiment, communications between two or more systems and/or devices can be achieved by a secure communications protocol, such as secure sockets layer (SSL) or transport layer security (TLS). In addition, data and/or transactional details may be encrypted.

Some aspects may utilize the Internet of Things (IoT), where things (e.g., machines, devices, phones, sensors) can be connected to networks and the data from these things can be collected and processed within the things and/or external to the things. For example, the IoT can include sensors in many different devices, and high value analytics can be applied to identify hidden relationships and drive increased efficiencies. This can apply to both big data analytics and real-time (e.g., ESP) analytics. IoT may be implemented in various areas, such as for access (technologies that get data and move it), embed-ability (devices with embedded sensors), and services. Industries in the IoT space may automotive (connected car), manufacturing (connected factory), smart cities, energy and retail. This will be described further below with respect to FIG. 2.

As noted, computing environment 114 may include a communications grid 120 and a transmission network database system 118. Communications grid 120 may be a grid-based computing system for processing large amounts of data. The transmission network database system 118 may be for managing, storing, and retrieving large amounts of data that are distributed to and stored in the one or more network-attached data stores 110 or other data stores that reside at different locations within the transmission network database system 118. The compute nodes in the grid-based computing system 120 and the transmission network database system 118 may share the same processor hardware, such as processors that are located within computing environment 114.

Figure 2:
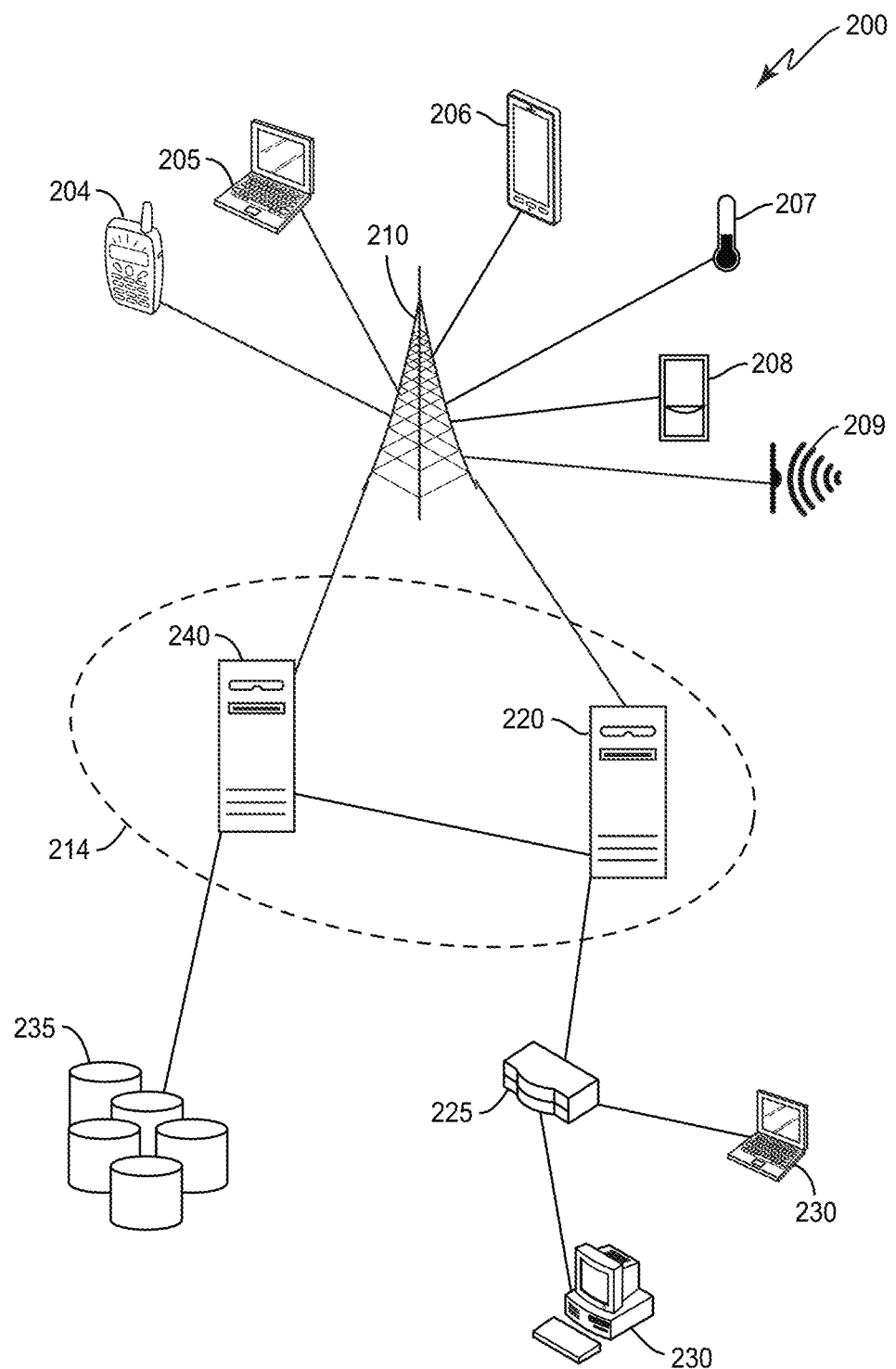
FIG. 2 illustrates an example network including an example set of devices communicating with each other over an exchange system and via a network, according to at least one embodiment of the present technology.

FIG. 2 illustrates an example network including an example set of devices communicating with each other over an exchange system and via a network, according to embodiments of the present technology. As noted, each communication within data transmission network 100 may occur over one or more networks. System 200 includes a network device 204 configured to communicate with a variety of types of client devices, for example client devices 230, over a variety of types of communication channels.

As shown in FIG. 2, network device 204 can transmit a communication over a network (e.g., a cellular network via a base station 210). The communication can be routed to another network device, such as network devices 205-209, via base station 210. The communication can also be routed to computing environment 214 via base station 210. For example, network device 204 may collect data either from its surrounding environment or from other network devices (such as network devices 205-209) and transmit that data to computing environment 214.

Although network devices 204-209 are shown in FIG. 2 as a mobile phone, laptop computer, tablet computer, temperature sensor, motion sensor, and audio sensor respectively, the network devices may be or include sensors that are sensitive to detecting aspects of their environment. For example, the network devices may include sensors such as water sensors, power sensors, electrical current sensors, chemical sensors, optical sensors, pressure sensors, geographic or position sensors (e.g., GPS), velocity sensors, acceleration sensors, flow rate sensors, among others. Examples of characteristics that may be sensed include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, electrical current, among others. The sensors may be mounted to various components used as part of a variety of different types of systems (e.g., an oil drilling operation). The network devices may detect and record data related to the environment that it monitors, and transmit that data to computing environment 214.

As noted, one type of system that may include various sensors that collect data to be processed and/or transmitted to a computing environment according to certain embodiments includes an oil drilling system. For example, the one or more drilling operation sensors may include surface sensors that measure a hook load, a fluid rate, a temperature and a density in and out of the wellbore, a standpipe pressure, a surface torque, a rotation speed of a drill pipe, a rate of penetration, a mechanical specific energy, etc. and downhole sensors that measure a rotation speed of a bit, fluid densities, downhole torque, downhole vibration (axial, tangential, lateral), a weight applied at a drill bit, an annular pressure, a differential pressure, an azimuth, an inclination, a dog leg severity, a measured depth, a vertical depth, a downhole temperature, etc. Besides the raw data collected directly by the sensors, other data may include parameters either developed by the sensors or assigned to the system by a client or other controlling device. For example, one or more drilling operation control parameters may control settings such as a mud motor speed to flow ratio, a bit diameter, a predicted formation top, seismic data, weather data, etc. Other data may be generated using physical models such as an earth model, a weather model, a seismic model, a bottom hole assembly model, a well plan model, an annular friction model, etc. In addition to sensor and control settings, predicted outputs, of for example, the rate of penetration, mechanical specific energy, hook load, flow in fluid rate, flow out fluid rate, pump pressure, surface torque, rotation speed of the drill pipe, annular pressure, annular friction pressure, annular temperature, equivalent circulating density, etc. may also be stored in the data warehouse.

In another example, another type of system that may include various sensors that collect data to be processed and/or transmitted to a computing environment according to certain embodiments includes a home automation or similar automated network in a different environment, such as an office space, school, public space, sports venue, or a variety of other locations. Network devices in such an automated network may include network devices that allow a user to access, control, and/or configure various home appliances located within the user's home (e.g., a television, radio, light, fan, humidifier, sensor, microwave, iron, and/or the like), or outside of the user's home (e.g., exterior motion sensors, exterior lighting, garage door openers, sprinkler systems, or the like). For example, network device 102 may include a home automation switch that may be coupled with a home appliance. In another embodiment, a network device can allow a user to access, control, and/or configure devices, such as office-related devices (e.g., copy machine, printer, or fax machine), audio and/or video related devices (e.g., a receiver, a speaker, a projector, a DVD player, or a television), media-playback devices (e.g., a compact disc player, a CD player, or the like), computing devices (e.g., a home computer, a laptop computer, a tablet, a personal digital assistant (PDA), a computing device, or a wearable device), lighting devices (e.g., a lamp or recessed lighting), devices associated with a security system, devices associated with an alarm system, devices that can be operated in an automobile (e.g., radio devices, navigation devices), and/or the like. Data may be collected from such various sensors in raw form, or data may be processed by the sensors to create parameters or other data either developed by the sensors based on the raw data or assigned to the system by a client or other controlling device.

In another example, another type of system that may include various sensors that collect data to be processed and/or transmitted to a computing environment according to certain embodiments includes a power or energy grid. A variety of different network devices may be included in an energy grid, such as various devices within one or more power plants, energy farms (e.g., wind farm, solar farm, among others) energy storage facilities, factories, homes and businesses of consumers, among others. One or more of such devices may include one or more sensors that detect energy gain or loss, electrical input or output or loss, and a variety of other efficiencies. These sensors may collect data to inform users of how the energy grid, and individual devices within the grid, may be functioning and how they may be made more efficient.

Network device sensors may also perform processing on data it collects before transmitting the data to the computing environment 114, or before deciding whether to transmit data to the computing environment 114. For example, network devices may determine whether data collected meets certain rules, for example by comparing data or values calculated from the data and comparing that data to one or more thresholds. The network device may use this data and/or comparisons to determine if the data should be transmitted to the computing environment 214 for further use or processing.

Computing environment 214 may include machines 220 and 240. Although computing environment 214 is shown in FIG. 2 as having two machines, 220 and 240, computing environment 214 may have only one machine or may have more than two machines. The machines that make up computing environment 214 may include specialized computers, servers, or other machines that are configured to individually and/or collectively process large amounts of data. The computing environment 214 may also include storage devices that include one or more databases of structured data, such as data organized in one or more hierarchies, or unstructured data. The databases may communicate with the processing devices within computing environment 214 to distribute data to them. Since network devices may transmit data to computing environment 214, that data may be received by the computing environment 214 and subsequently stored within those storage devices. Data used by computing environment 214 may also be stored in data stores 235, which may also be a part of or connected to computing environment 214.

Computing environment 214 can communicate with various devices via one or more routers 225 or other inter-network or intra-network connection components. For example, computing environment 214 may communicate with devices 230 via one or more routers 225. Computing environment 214 may collect, analyze and/or store data from or pertaining to communications, client device operations, client rules, and/or user-associated actions stored at one or more data stores 235. Such data may influence communication routing to the devices within computing environment 214, how data is stored or processed within computing environment 214, among other actions.

Notably, various other devices can further be used to influence communication routing and/or processing between devices within computing environment 214 and with devices outside of computing environment 214. For example, as shown in FIG. 2, computing environment 214 may include a web server 240. Thus, computing environment 214 can retrieve data of interest, such as client information (e.g., product information, client rules, etc.), technical product details, news, current or predicted weather, and so on.

In addition to computing environment 214 collecting data (e.g., as received from network devices, such as sensors, and client devices or other sources) to be processed as part of a big data analytics project, it may also receive data in real time as part of a streaming analytics environment. As noted, data may be collected using a variety of sources as communicated via different kinds of networks or locally. Such data may be received on a real-time streaming basis. For example, network devices may receive data periodically from network device sensors as the sensors continuously sense, monitor and track changes in their environments. Devices within computing environment 214 may also perform pre-analysis on data it receives to determine if the data received should be processed as part of an ongoing project. The data received and collected by computing environment 214, no matter what the source or method or timing of receipt, may be processed over a period of time for a client to determine results data based on the client's needs and rules.

Figure 3:
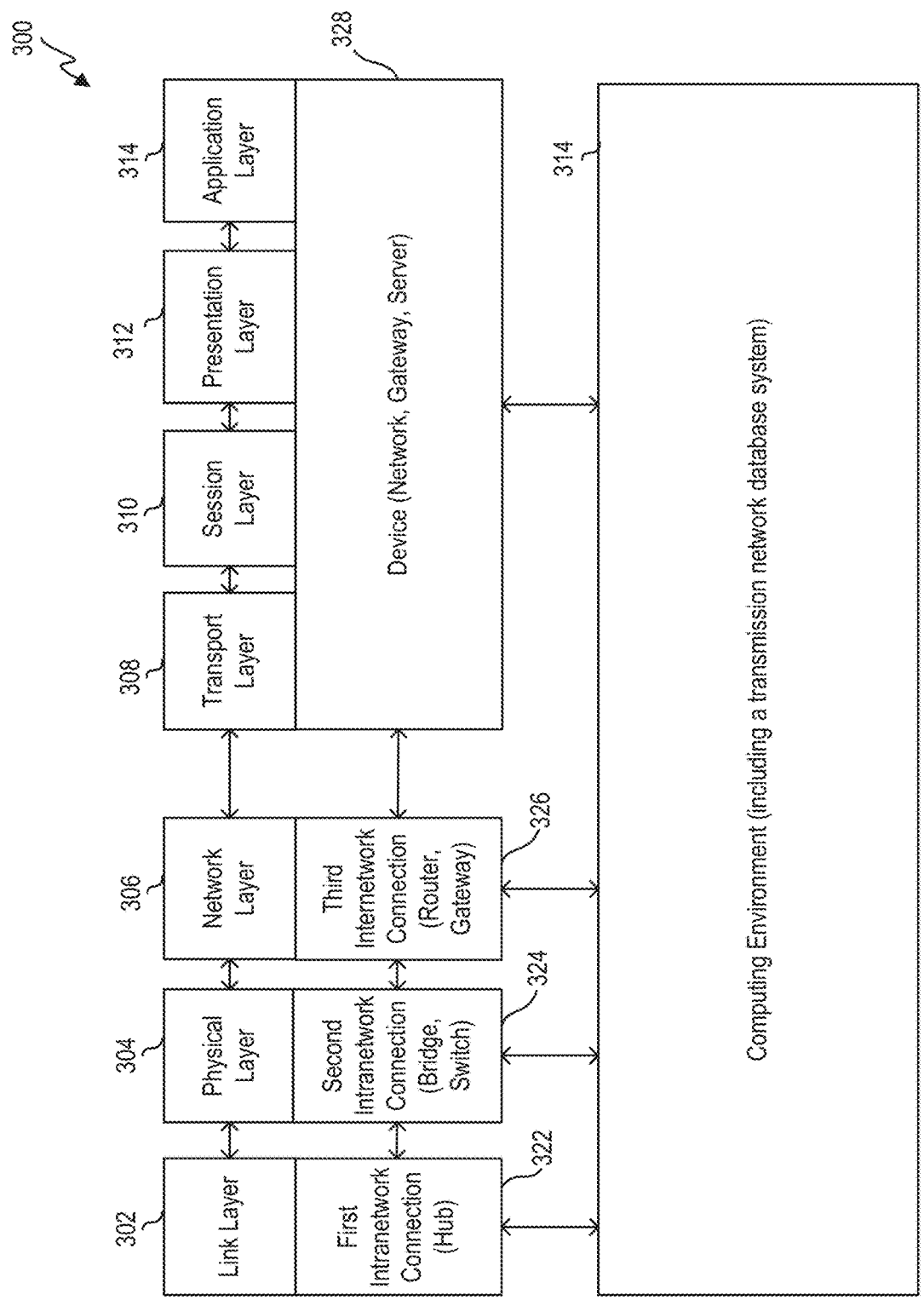
FIG. 3 illustrates a representation of a conceptual model of a communications protocol system, according to at least one embodiment of the present technology.

FIG. 3 illustrates a representation of a conceptual model of a communications protocol system, according to embodiments of the present technology. More specifically, FIG. 3 identifies operation of a computing environment in an Open Systems Interaction model that corresponds to various connection components. The model 300 shows, for example, how a computing environment, such as computing environment 314 (or computing environment 214 in FIG. 2) may communicate with other devices in its network, and control how communications between the computing environment and other devices are executed and under what conditions.

The model can include layers 302-314. The layers are arranged in a stack. Each layer in the stack serves the layer one level higher than it (except for the application layer, which is the highest layer), and is served by the layer one level below it (except for the physical layer, which is the lowest layer). The physical layer is the lowest layer because it receives and transmits raw bites of data, and is the farthest layer from the user in a communications system. On the other hand, the application layer is the highest layer because it interacts directly with a software application.

As noted, the model includes a physical layer 302. Physical layer 302 represents physical communication, and can define parameters of that physical communication. For example, such physical communication may come in the form of electrical, optical, or electromagnetic signals. Physical layer 302 also defines protocols that may control communications within a data transmission network.

Link layer 304 defines links and mechanisms used to transmit (i.e., move) data across a network. The link layer manages node-to-node communications, such as within a grid computing environment. Link layer 304 can detect and correct errors (e.g., transmission errors in the physical layer 302). Link layer 304 can also include a media access control (MAC) layer and logical link control (LLC) layer.

Network layer 306 defines the protocol for routing within a network. In other words, the network layer coordinates transferring data across nodes in a same network (e.g., such as a grid computing environment). Network layer 306 can also define the processes used to structure local addressing within the network.

Transport layer 308 can manage the transmission of data and the quality of the transmission and/or receipt of that data. Transport layer 308 can provide a protocol for transferring data, such as, for example, a Transmission Control Protocol (TCP). Transport layer 308 can assemble and disassemble data frames for transmission. The transport layer can also detect transmission errors occurring in the layers below it.

Session layer 310 can establish, maintain, and manage communication connections between devices on a network. In other words, the session layer controls the dialogues or nature of communications between network devices on the network. The session layer may also establish checkpointing, adjournment, termination, and restart procedures.

Presentation layer 312 can provide translation for communications between the application and network layers. In other words, this layer may encrypt, decrypt and/or format data based on data types known to be accepted by an application or network layer.

Application layer 314 interacts directly with software applications and end users, and manages communications between them. Application layer 314 can identify destinations, local resource states or availability and/or communication content or formatting using the applications.

Intra-network connection components 322 and 324 are shown to operate in lower levels, such as physical layer 302 and link layer 304, respectively. For example, a hub can operate in the physical layer, a switch can operate in the physical layer, and a router can operate in the network layer. Inter-network connection components 326 and 328 are shown to operate on higher levels, such as layers 306-314. For example, routers can operate in the network layer and network devices can operate in the transport, session, presentation, and application layers.

As noted, a computing environment 314 can interact with and/or operate on, in various embodiments, one, more, all or any of the various layers. For example, computing environment 314 can interact with a hub (e.g., via the link layer) so as to adjust which devices the hub communicates with. The physical layer may be served by the link layer, so it may implement such data from the link layer. For example, the computing environment 314 may control which devices it will receive data from. For example, if the computing environment 314 knows that a certain network device has turned off, broken, or otherwise become unavailable or unreliable, the computing environment 314 may instruct the hub to prevent any data from being transmitted to the computing environment 314 from that network device. Such a process may be beneficial to avoid receiving data that is inaccurate or that has been influenced by an uncontrolled environment. As another example, computing environment 314 can communicate with a bridge, switch, router or gateway and influence which device within the system (e.g., system 200) the component selects as a destination. In some embodiments, computing environment 314 can interact with various layers by exchanging communications with equipment operating on a particular layer by routing or modifying existing communications. In another embodiment, such as in a grid computing environment, a node may determine how data within the environment should be routed (e.g., which node should receive certain data) based on certain parameters or information provided by other layers within the model.

As noted, the computing environment 314 may be a part of a communications grid environment, the communications of which may be implemented as shown in the protocol of FIG. 3. For example, referring back to FIG. 2, one or more of machines 220 and 240 may be part of a communications grid computing environment. A gridded computing environment may be employed in a distributed system with non-interactive workloads where data resides in memory on the machines, or compute nodes. In such an environment, analytic code, instead of a database management system, controls the processing performed by the nodes. Data is co-located by pre-distributing it to the grid nodes, and the analytic code on each node loads the local data into memory. Each node may be assigned a particular task such as a portion of a processing project, or to organize or control other nodes within the grid.

Figure 4:
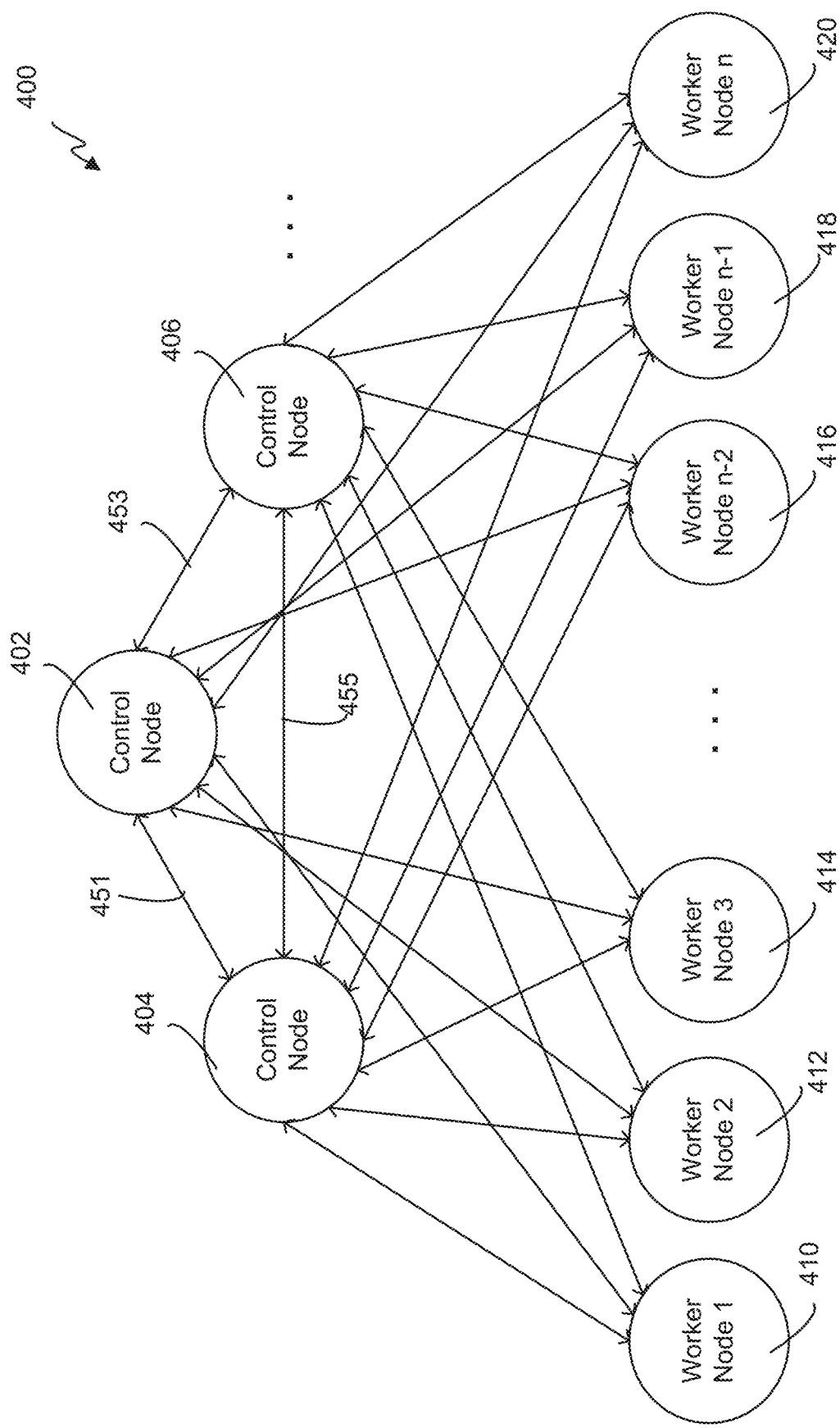
FIG. 4 illustrates a communications grid computing system including a variety of control and worker nodes, according to at least one embodiment of the present technology.

FIG. 4 illustrates a communications grid computing system 400 including a variety of control and worker nodes, according to embodiments of the present technology. Communications grid computing system 400 includes three control nodes and one or more worker nodes. Communications grid computing system 400 includes control nodes 402, 404, and 406. The control nodes are communicatively connected via communication paths 451, 453, and 455. Therefore, the control nodes may transmit information (e.g., related to the communications grid or notifications), to and receive information from each other. Although communications grid computing system 400 is shown in FIG. 4 as including three control nodes, the communications grid may include more or less than three control nodes.

Communications grid computing system (or just "communications grid") 400 also includes one or more worker nodes. Shown in FIG. 4 are six worker nodes 410-420. Although FIG. 4 shows six worker nodes, a communications grid according to embodiments of the present technology may include more or less than six worker nodes. The number of worker nodes included in a communications grid may be dependent upon how large the project or data set is being processed by the communications grid, the capacity of each worker node, the time designated for the communications grid to complete the project, among others. Each worker node within the communications grid 400 may be connected (wired or wirelessly, and directly or indirectly) to control nodes 402-406. Therefore, each worker node may receive information from the control nodes (e.g., an instruction to perform work on a project) and may transmit information to the control nodes (e.g., a result from work performed on a project). Furthermore, worker nodes may communicate with each other (either directly or indirectly). For example, worker nodes may transmit data between each other related to a job being performed or an individual task within a job being performed by that worker node. However, in certain embodiments, worker nodes may not, for example, be connected (communicatively or otherwise) to certain other worker nodes. In an embodiment, worker nodes may only be able to communicate with the control node that controls it, and may not be able to communicate with other worker nodes in the communications grid, whether they are other worker nodes controlled by the control node that controls the worker node, or worker nodes that are controlled by other control nodes in the communications grid.

A control node may connect with an external device with which the control node may communicate (e.g., a grid user, such as a server or computer, may connect to a controller of the grid). For example, a server or computer may connect to control nodes and may transmit a project or job to the node. The project may include a data set. The data set may be of any size. Once the control node receives such a project including a large data set, the control node may distribute the data set or projects related to the data set to be performed by worker nodes. Alternatively, for a project including a large data set, the data set may be receive or stored by a machine other than a control node (e.g., a Hadoop data node).

Control nodes may maintain knowledge of the status of the nodes in the grid (i.e., grid status information), accept work requests from clients, subdivide the work across worker nodes, coordinate the worker nodes, among other responsibilities. Worker nodes may accept work requests from a control node and provide the control node with results of the work performed by the worker node. A grid may be started from a single node (e.g., a machine, computer, server, etc.). This first node may be assigned or may start as the primary control node that will control any additional nodes that enter the grid.

When a project is submitted for execution (e.g., by a client or a controller of the grid) it may be assigned to a set of nodes. After the nodes are assigned to a project, a data structure (i.e., a communicator) may be created. The communicator may be used by the project for information to be shared between the project code running on each node. A communication handle may be created on each node. A handle, for example, is a reference to the communicator that is valid within a single process on a single node, and the handle may be used when requesting communications between nodes.

A control node, such as control node 402, may be designated as the primary control node. A server, computer or other external device may connect to the primary control node. Once the control node receives a project, the primary control node may distribute portions of the project to its worker nodes for execution. For example, when a project is initiated on communications grid 400, primary control node 402 controls the work to be performed for the project in order to complete the project as requested or instructed. The primary control node may distribute work to the worker nodes based on various factors, such as which subsets or portions of projects may be completed most efficiently and in the correct amount of time. For example, a worker node may perform analysis on a portion of data that is already local (e.g., stored on) the worker node. The primary control node also coordinates and processes the results of the work performed by each worker node after each worker node executes and completes its job. For example, the primary control node may receive a result from one or more worker nodes, and the control node may organize (e.g., collect and assemble) the results received and compile them to produce a complete result for the project received from the end user.

Any remaining control nodes, such as control nodes 404 and 406, may be assigned as backup control nodes for the project. In an embodiment, backup control nodes may not control any portion of the project Instead, backup control nodes may serve as a backup for the primary control node and take over as primary control node if the primary control node were to fail. If a communications grid were to include only a single control node, and the control node were to fail (e.g., the control node is shut off or breaks) then the communications grid as a whole may fail and any project or job being run on the communications grid may fail and may not complete. While the project may be run again, such a failure may cause a delay (severe delay in some cases, such as overnight delay) in completion of the project Therefore, a grid with multiple control nodes, including a backup control node, may be beneficial.

To add another node or machine to the grid, the primary control node may open a pair of listening sockets, for example. A socket may be used to accept work requests from clients, and the second socket may be used to accept connections from other grid nodes). The primary control node may be provided with a list of other nodes (e.g., other machines, computers, servers) that will participate in the grid, and the role that each node will fill in the grid. Upon startup of the primary control node (e.g., the first node on the grid), the primary control node may use a network protocol to start the server process on every other node in the grid. Command line parameters, for example, may inform each node of one or more pieces of information, such as: the role that the node will have in the grid, the host name of the primary control node, the port number on which the primary control node is accepting connections from peer nodes, among others. The information may also be provided in a configuration file, transmitted over a secure shell tunnel, recovered from a configuration server, among others. While the other machines in the grid may not initially know about the configuration of the grid, that information may also be sent to each other node by the primary control node. Updates of the grid information may also be subsequently sent to those nodes.

For any control node other than the primary control node added to the grid, the control node may open three sockets. The first socket may accept work requests from clients, the second socket may accept connections from other grid members, and the third socket may connect (e.g., permanently) to the primary control node. When a control node (e.g., primary control node) receives a connection from another control node, it first checks to see if the peer node is in the list of configured nodes in the grid. If it is not on the list, the control node may clear the connection. If it is on the list, it may then attempt to authenticate the connection. If authentication is successful, the authenticating node may transmit information to its peer, such as the port number on which a node is listening for connections, the host name of the node, information about how to authenticate the node, among other information. When a node, such as the new control node, receives information about another active node, it will check to see if it already has a connection to that other node. If it does not have a connection to that node, it may then establish a connection to that control node.

Any worker node added to the grid may establish a connection to the primary control node and any other control nodes on the grid. After establishing the connection, it may authenticate itself to the grid (e.g., any control nodes, including both primary and backup, or a server or user controlling the grid). After successful authentication, the worker node may accept configuration information from the control node.

When a node joins a communications grid (e.g., when the node is powered on or connected to an existing node on the grid or both), the node is assigned (e.g., by an operating system of the grid) a universally unique identifier (UUID). This unique identifier may help other nodes and external entities (devices, users, etc.) to identify the node and distinguish it from other nodes. When a node is connected to the grid, the node may share its unique identifier with the other nodes in the grid. Since each node may share its unique identifier, each node may know the unique identifier of every other node on the grid. Unique identifiers may also designate a hierarchy of each of the nodes (e.g., backup control nodes) within the grid. For example, the unique identifiers of each of the backup control nodes may be stored in a list of backup control nodes to indicate an order in which the backup control nodes will take over for a failed primary control node to become a new primary control node. However, a hierarchy of nodes may also be determined using methods other than using the unique identifiers of the nodes. For example, the hierarchy may be predetermined, or may be assigned based on other predetermined factors.

The grid may add new machines at any time (e.g., initiated from any control node). Upon adding a new node to the grid, the control node may first add the new node to its table of grid nodes. The control node may also then notify every other control node about the new node. The nodes receiving the notification may acknowledge that they have updated their configuration information.

Primary control node 402 may, for example, transmit one or more communications to backup control nodes 404 and 406 (and, for example, to other control or worker nodes within the communications grid). Such communications may sent periodically, at fixed time intervals, between known fixed stages of the project's execution, among other protocols. The communications transmitted by primary control node 402 may be of varied types and may include a variety of types of information. For example, primary control node 402 may transmit snapshots (e.g., status information) of the communications grid so that backup control node 404 always has a recent snapshot of the communications grid. The snapshot or grid status may include, for example, the structure of the grid (including, for example, the worker nodes in the grid, unique identifiers of the nodes, or their relationships with the primary control node) and the status of a project (including, for example, the status of each worker node's portion of the project). The snapshot may also include analysis or results received from worker nodes in the communications grid. The backup control nodes may receive and store the backup data received from the primary control node. The backup control nodes may transmit a request for such a snapshot (or other information) from the primary control node, or the primary control node may send such information periodically to the backup control nodes.

As noted, the backup data may allow the backup control node to take over as primary control node if the primary control node fails without requiring the grid to start the project over from scratch. If the primary control node fails, the backup control node that will take over as primary control node may retrieve the most recent version of the snapshot received from the primary control node and use the snapshot to continue the project from the stage of the project indicated by the backup data. This may prevent failure of the project as a whole.

A backup control node may use various methods to determine that the primary control node has failed. In one example of such a method, the primary control node may transmit (e.g., periodically) a communication to the backup control node that indicates that the primary control node is working and has not failed, such as a heartbeat communication. The backup control node may determine that the primary control node has failed if the backup control node has not received a heartbeat communication for a certain predetermined period of time. Alternatively, a backup control node may also receive a communication from the primary control node itself (before it failed) or from a worker node that the primary control node has failed, for example because the primary control node has failed to communicate with the worker node.

Different methods may be performed to determine which backup control node of a set of backup control nodes (e.g., backup control nodes 404 and 406) will take over for failed primary control node 402 and become the new primary control node. For example, the new primary control node may be chosen based on a ranking or "hierarchy" of backup control nodes based on their unique identifiers. In an alternative embodiment, a backup control node may be assigned to be the new primary control node by another device in the communications grid or from an external device (e.g., a system infrastructure or an end user, such as a server or computer, controlling the communications grid). In another alternative embodiment, the backup control node that takes over as the new primary control node may be designated based on bandwidth or other statistics about the communications grid.

A worker node within the communications grid may also fail. If a worker node fails, work being performed by the failed worker node may be redistributed amongst the operational worker nodes. In an alternative embodiment, the primary control node may transmit a communication to each of the operable worker nodes still on the communications grid that each of the worker nodes should purposefully fail also. After each of the worker nodes fail, they may each retrieve their most recent saved checkpoint of their status and re-start the project from that checkpoint to minimize lost progress on the project being executed.

Figure 5:
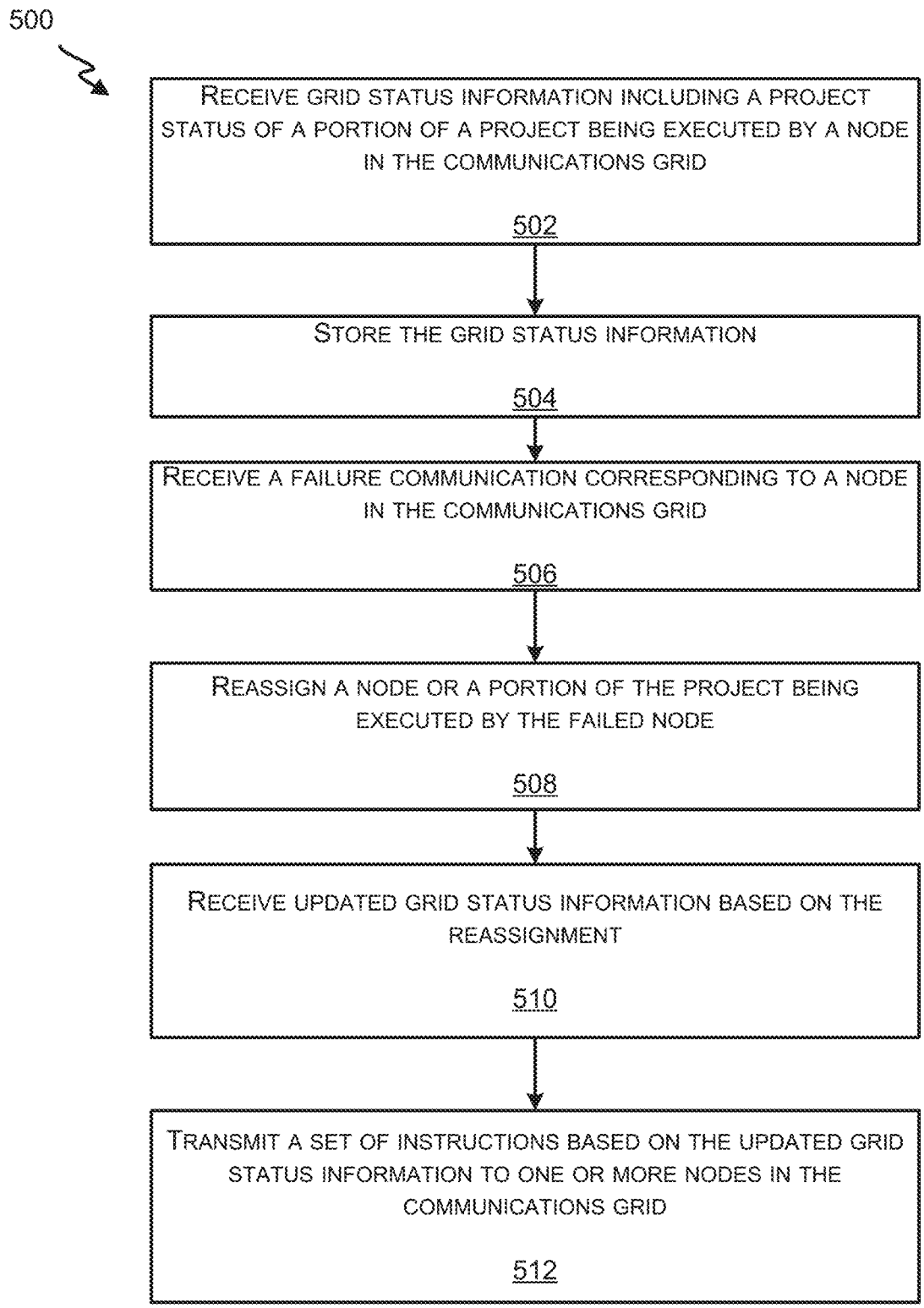
FIG. 5 illustrates a flow chart showing an example process for adjusting a communications grid or a work project in a communications grid after a failure of a node, according to at least one embodiment of the present technology.

FIG. 5 illustrates a flow chart showing an example process for adjusting a communications grid or a work project in a communications grid after a failure of a node, according to embodiments of the present technology. The process may include, for example, receiving grid status information including a project status of a portion of a project being executed by a node in the communications grid, as described in operation 502. For example, a control node (e.g., a backup control node connected to a primary control node and a worker node on a communications grid) may receive grid status information, where the grid status information includes a project status of the primary control node or a project status of the worker node. The project status of the primary control node and the project status of the worker node may include a status of one or more portions of a project being executed by the primary and worker nodes in the communications grid. The process may also include storing the grid status information, as described in operation 504. For example, a control node (e.g., a backup control node) may store the received grid status information locally within the control node. Alternatively, the grid status information may be sent to another device for storage where the control node may have access to the information.

The process may also include receiving a failure communication corresponding to a node in the communications grid in operation 506. For example, a node may receive a failure communication including an indication that the primary control node has failed, prompting a backup control node to take over for the primary control node. In an alternative embodiment, a node may receive a failure that a worker node has failed, prompting a control node to reassign the work being performed by the worker node. The process may also include reassigning a node or a portion of the project being executed by the failed node, as described in operation 508. For example, a control node may designate the backup control node as a new primary control node based on the failure communication upon receiving the failure communication. If the failed node is a worker node, a control node may identify a project status of the failed worker node using the snapshot of the communications grid, where the project status of the failed worker node includes a status of a portion of the project being executed by the failed worker node at the failure time.

The process may also include receiving updated grid status information based on the reassignment, as described in operation 510, and transmitting a set of instructions based on the updated grid status information to one or more nodes in the communications grid, as described in operation 512. The updated grid status information may include an updated project status of the primary control node or an updated project status of the worker node. The updated information may be transmitted to the other nodes in the grid to update their stale stored information.

Figure 6:
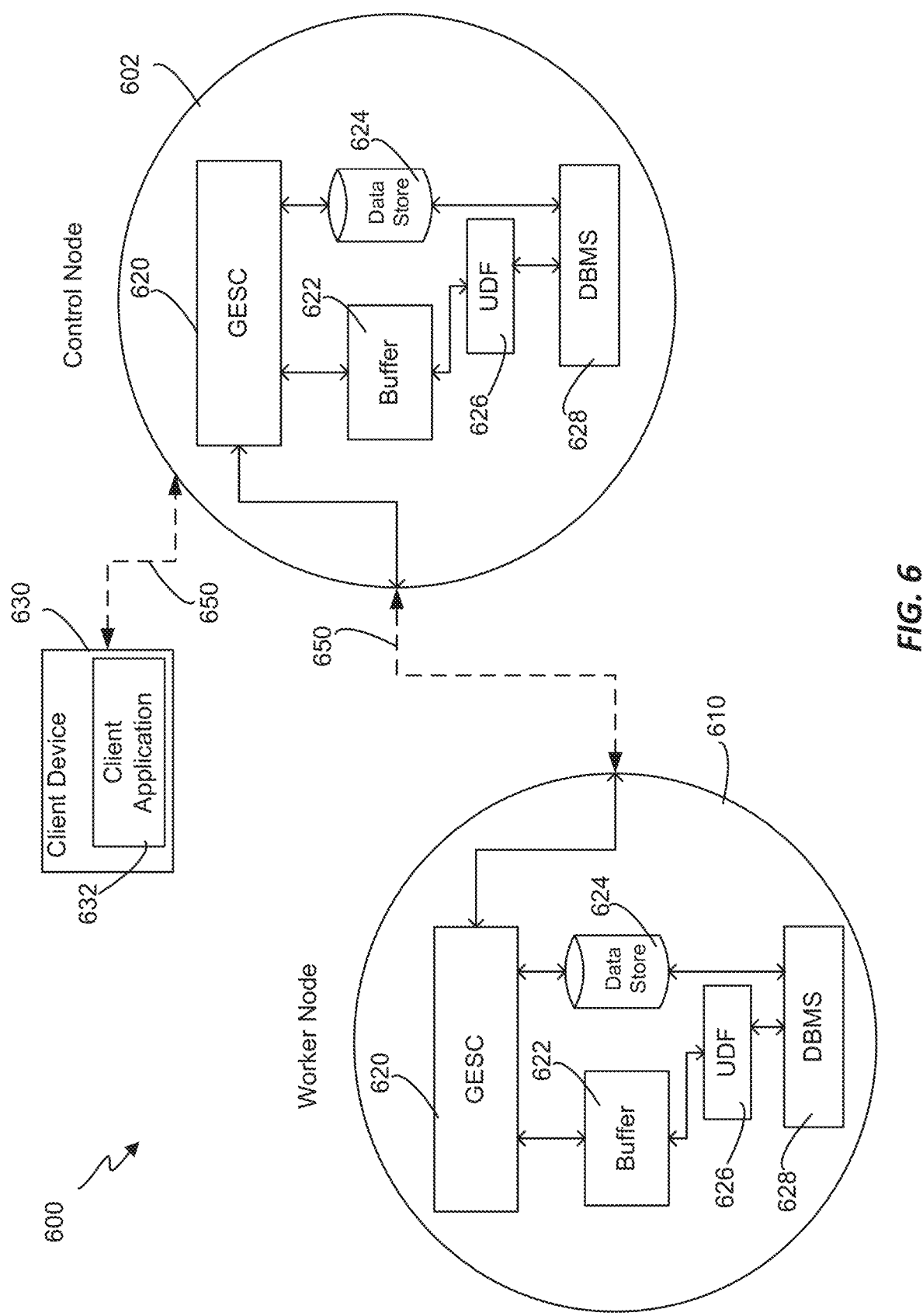
FIG. 6 illustrates a portion of a communications grid computing system including a control node and a worker node, according to at least one embodiment of the present technology.

FIG. 6 illustrates a portion of a communications grid computing system 600 including a control node and a worker node, according to embodiments of the present technology. Communications grid 600 computing system includes one control node (control node 602) and one worker node (worker node 610) for purposes of illustration, but may include more worker and/or control nodes. The control node 602 is communicatively connected to worker node 610 via communication path 650. Therefore, control node 602 may transmit information (e.g., related to the communications grid or notifications), to and receive information from worker node 610 via path 650.

Similar to in FIG. 4, communications grid computing system (or just "communications grid") 600 includes data processing nodes (control node 602 and worker node 610). Nodes 602 and 610 include multi-core data processors. Each node 602 and 610 includes a grid-enabled software component (GESC) 620 that executes on the data processor associated with that node and interfaces with buffer memory 622 also associated with that node. Each node 602 and 610 includes a database management software (DBMS) 628 that executes on a database server (not shown) at control node 602 and on a database server (not shown) at worker node 610.

Each node also includes a data store 624. Data stores 624, similar to network-attached data stores 110 in FIG. 1 and data stores 235 in FIG. 2, are used to store data to be processed by the nodes in the computing environment. Data stores 624 may also store any intermediate or final data generated by the computing system after being processed, for example in non-volatile memory. However in certain embodiments, the configuration of the grid computing environment allows its operations to be performed such that intermediate and final data results can be stored solely in volatile memory (e.g., RAM), without a requirement that intermediate or final data results be stored to non-volatile types of memory. Storing such data in volatile memory may be useful in certain situations, such as when the grid receives queries (e.g., ad hoc) from a client and when responses, which are generated by processing large amounts of data, need to be generated quickly or on-the-fly. In such a situation, the grid may be configured to retain the data within a memory so that responses can be generated at different levels of detail and so that a client may interactively query against this information.

Each node also includes a user-defined function (UDF) 626. The UDF provides a mechanism for the DMBS 628 to transfer data to or receive data from the database stored in the data stores 624 that are managed by the DBMS. For example, UDF 626 can be invoked by the DBMS to provide data to the GESC for processing. The UDF 626 may establish a socket connection (not shown) with the GESC to transfer the data. Alternatively, the UDF 626 can transfer data to the GESC by writing data to shared memory accessible by both the UDF and the GESC.

The GESC 620 at the nodes 602 and 620 may be connected via a network, such as network 108 shown in FIG. 1. Therefore, nodes 602 and 620 can communicate with each other via the network using a predetermined communication protocol such as, for example, the Message Passing Interface (MPI). Each GESC 620 can engage in point-to-point communication with the GESC at another node or in collective communication with multiple GESCs via the network. The GESC 620 at each node may contain identical (or nearly identical) software instructions. Each node may be capable of operating as either a control node or a worker node. The GESC at the control node 602 can communicate, over a communication path 652, with a client device 630. More specifically, control node 602 may communicate with client application 632 hosted by the client device 630 to receive queries and to respond to those queries after processing large amounts of data.

DMBS 628 may control the creation, maintenance, and use of database or data structure (not shown) within a nodes 602 or 610. The database may organize data stored in data stores 624. The DMBS 628 at control node 602 may accept requests for data and transfer the appropriate data for the request With such a process, collections of data may be distributed across multiple physical locations. In this example, each node 602 and 610 stores a portion of the total data managed by the management system in its associated data store 624.

Furthermore, the DBMS may be responsible for protecting against data loss using replication techniques. Replication includes providing a backup copy of data stored on one node on one or more other nodes. Therefore, if one node fails, the data from the failed node can be recovered from a replicated copy residing at another node. However, as described herein with respect to FIG. 4, data or status information for each node in the communications grid may also be shared with each node on the grid.

Figure 7:
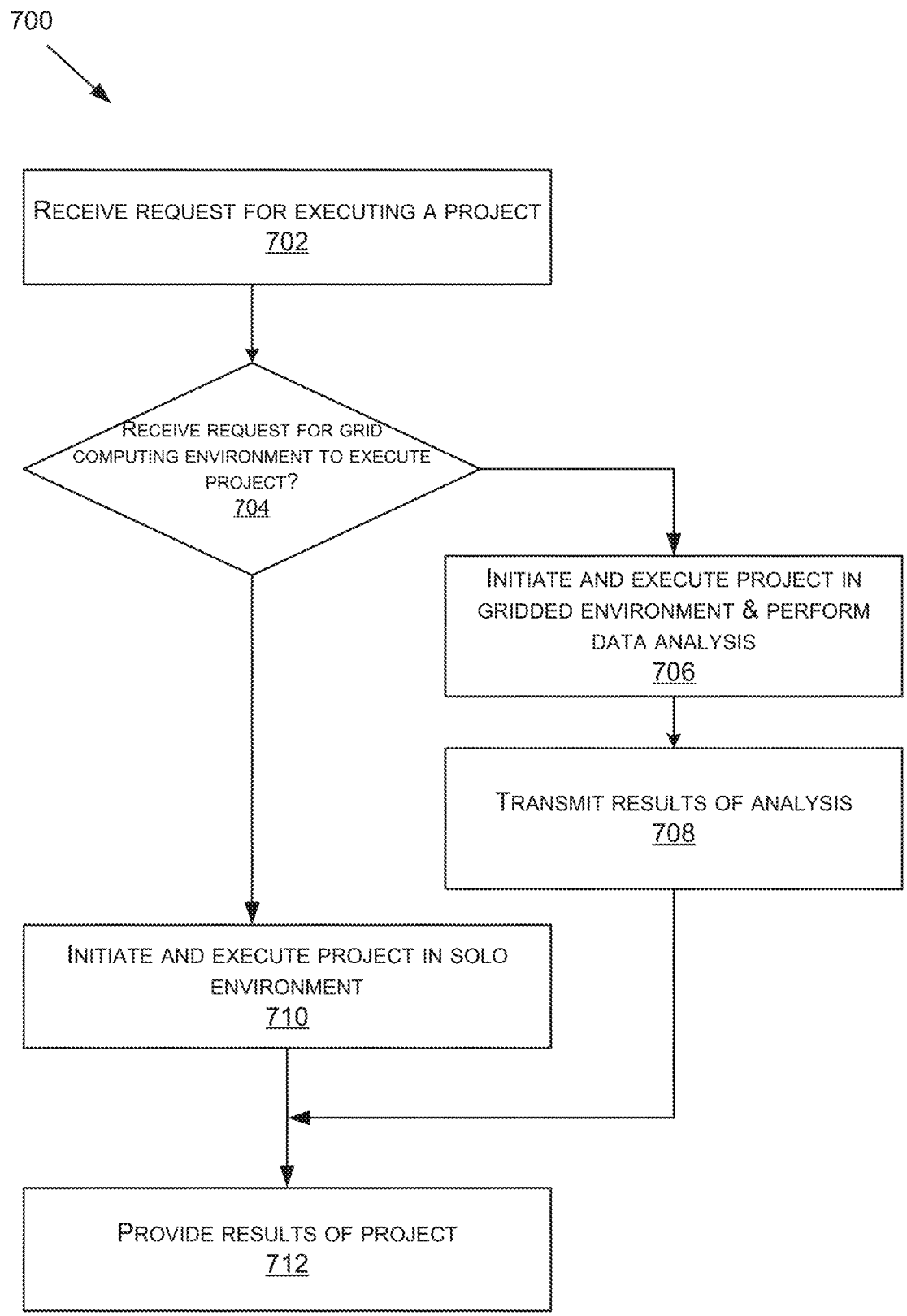
FIG. 7 illustrates a flow chart showing an example process for executing a data analysis or processing project, according to at least one embodiment of the present technology.

FIG. 7 illustrates a flow chart showing an example method for executing a project within a grid computing system, according to embodiments of the present technology. As described with respect to FIG. 6, the GESC at the control node may transmit data with a client device (e.g., client device 630) to receive queries for executing a project and to respond to those queries after large amounts of data have been processed. The query may be transmitted to the control node, where the query may include a request for executing a project, as described in operation 702. The query can contain instructions on the type of data analysis to be performed in the project and whether the project should be executed using the grid-based computing environment, as shown in operation 704.

To initiate the project, the control node may determine if the query requests use of the grid-based computing environment to execute the project. If the determination is no, then the control node initiates execution of the project in a solo environment (e.g., at the control node), as described in operation 710. If the determination is yes, the control node may initiate execution of the project in the grid-based computing environment, as described in operation 706. In such a situation, the request may include a requested configuration of the grid. For example, the request may include a number of control nodes and a number of worker nodes to be used in the grid when executing the project After the project has been completed, the control node may transmit results of the analysis yielded by the grid, as described in operation 708. Whether the project is executed in a solo or grid-based environment, the control node provides the results of the project.

As noted with respect to FIG. 2, the computing environments described herein may collect data (e.g., as received from network devices, such as sensors, such as network devices 204-209 in FIG. 2, and client devices or other sources) to be processed as part of a data analytics project, and data may be received in real time as part of a streaming analytics environment (e.g., ESP). Data may be collected using a variety of sources as communicated via different kinds of networks or locally, such as on a real-time streaming basis. For example, network devices may receive data periodically from network device sensors as the sensors continuously sense, monitor and track changes in their environments. More specifically, an increasing number of distributed applications develop or produce continuously flowing data from distributed sources by applying queries to the data before distributing the data to geographically distributed recipients. An event stream processing engine (ESPE) may continuously apply the queries to the data as it is received and determines which entities should receive the data. Client or other devices may also subscribe to the ESPE or other devices processing ESP data so that they can receive data after processing, based on for example the entities determined by the processing engine. For example, client devices 230 in FIG. 2 may subscribe to the ESPE in computing environment 214. In another example, event subscription devices 1024*a-c*, described further with respect to FIG. 10, may also subscribe to the ESPE. The ESPE may determine or define how input data or event streams from network devices or other publishers (e.g., network devices 204-209 in FIG. 2) are transformed into meaningful output data to be consumed by subscribers, such as for example client devices 230 in FIG. 2.

FIG. 8 illustrates a block diagram including components of an Event Stream Processing Engine (ESPE), according to embodiments of the present technology. ESPE 800 may include one or more projects 802. A project may be described as a second-level container in an engine model managed by ESPE 800 where a thread pool size for the project may be defined by a user. Each project of the one or more projects 802 may include one or more continuous queries 804 that contain data flows, which are data transformations of incoming event streams. The one or more continuous queries 804 may include one or more source windows 806 and one or more derived windows 808.

The ESPE may receive streaming data over a period of time related to certain events, such as events or other data sensed by one or more network devices. The ESPE may perform operations associated with processing data created by the one or more devices. For example, the ESPE may receive data from the one or more network devices 204-209 shown in FIG. 2. As noted, the network devices may include sensors that sense different aspects of their environments, and may collect data over time based on those sensed observations. For example, the ESPE may be implemented within one or more of machines 220 and 240 shown in FIG. 2. The ESPE may be implemented within such a machine by an ESP application. An ESP application may embed an ESPE with its own dedicated thread pool or pools into its application space where the main application thread can do application-specific work and the ESPE processes event streams at least by creating an instance of a model into processing objects.

The engine container is the top-level container in a model that manages the resources of the one or more projects 802. In an illustrative embodiment, for example, there may be only one ESPE 800 for each instance of the ESP application, and ESPE 800 may have a unique engine name. Additionally, the one or more projects 802 may each have unique project names, and each query may have a unique continuous query name and begin with a uniquely named source window of the one or more source windows 806. ESPE 800 may or may not be persistent.

Continuous query modeling involves defining directed graphs of windows for event stream manipulation and transformation. A window in the context of event stream manipulation and transformation is a processing node in an event stream processing model. A window in a continuous query can perform aggregations, computations, pattern-matching and other operations on data flowing through the window. A continuous query may be described as a directed graph of source, relational, pattern matching, and procedural windows. The one or more source windows 806 and the one or more derived windows 808 represent continuously executing queries that generate updates to a query result set as new event blocks stream through ESPE 800. A directed graph, for example, is a set of nodes connected by edges, where the edges have a direction associated with them.

An event object may be described as a packet of data accessible as a collection of fields, with at least one of the fields defined as a key or unique identifier (ID). The event object may be created using a variety of formats including binary, alphanumeric, XML, etc. Each event object may include one or more fields designated as a primary identifier (ID) for the event so ESPE 800 can support operation codes (opcodes) for events including insert, update, upsert, and delete. Upsert opcodes update the event if the key field already exists; otherwise, the event is inserted. For illustration, an event object may be a packed binary representation of a set of field values and include both metadata and field data associated with an event. The metadata may include an opcode indicating if the event represents an insert, update, delete, or upsert, a set of flags indicating if the event is a normal, partial-update, or a retention generated event from retention policy management, and a set of microsecond timestamps that can be used for latency measurements.

An event block object may be described as a grouping or package of event objects. An event stream may be described as a flow of event block objects. A continuous query of the one or more continuous queries 804 transforms a source event stream made up of streaming event block objects published into ESPE 800 into one or more output event streams using the one or more source windows 806 and the one or more derived windows 808. A continuous query can also be thought of as data flow modeling.

The one or more source windows 806 are at the top of the directed graph and have no windows feeding into them. Event streams are published into the one or more source windows 806, and from there, the event streams may be directed to the next set of connected windows as defined by the directed graph. The one or more derived windows 808 are all instantiated windows that are not source windows and that have other windows streaming events into them. The one or more derived windows 808 may perform computations or transformations on the incoming event streams. The one or more derived windows 808 transform event streams based on the window type (that is operators such as join, filter, compute, aggregate, copy, pattern match, procedural, union, etc.) and window settings. As event streams are published into ESPE 800, they are continuously queried, and the resulting sets of derived windows in these queries are continuously updated.

FIG. 9 illustrates a flow chart showing an example process including operations performed by an event stream processing engine, according to some embodiments of the present technology. As noted, the ESPE 800 (or an associated ESP application) defines how input event streams are transformed into meaningful output event streams. More specifically, the ESP application may define how input event streams from publishers (e.g., network devices providing sensed data) are transformed into meaningful output event streams consumed by subscribers (e.g., a data analytics project being executed by a machine or set of machines).

Within the application, a user may interact with one or more user interface windows presented to the user in a display under control of the ESPE independently or through a browser application in an order selectable by the user. For example, a user may execute an ESP application, which causes presentation of a first user interface window, which may include a plurality of menus and selectors such as drop down menus, buttons, text boxes, hyperlinks, etc. associated with the ESP application as understood by a person of skill in the art. As further understood by a person of skill in the art, various operations may be performed in parallel, for example, using a plurality of threads.

At operation 900, an ESP application may define and start an ESPE, thereby instantiating an ESPE at a device, such as machine 220 and/or 240. In an operation 902, the engine container is created. For illustration, ESPE 800 may be instantiated using a function call that specifies the engine container as a manager for the model.

In an operation 904, the one or more continuous queries 804 are instantiated by ESPE 800 as a model. The one or more continuous queries 804 may be instantiated with a dedicated thread pool or pools that generate updates as new events stream through ESPE 800. For illustration, the one or more continuous queries 804 may be created to model business processing logic within ESPE 800, to predict events within ESPE 800, to model a physical system within ESPE 800, to predict the physical system state within ESPE 800, etc. For example, as noted, ESPE 800 may be used to support sensor data monitoring and management (e.g., sensing may include force, torque, load, strain, position, temperature, air pressure, fluid flow, chemical properties, resistance, electromagnetic fields, radiation, irradiance, proximity, acoustics, moisture, distance, speed, vibrations, acceleration, electrical potential, or electrical current, etc.).

ESPE 800 may analyze and process events in motion or "event streams." Instead of storing data and running queries against the stored data, ESPE 800 may store queries and stream data through them to allow continuous analysis of data as it is received. The one or more source windows 806 and the one or more derived windows 808 may be created based on the relational, pattern matching, and procedural algorithms that transform the input event streams into the output event streams to model, simulate, score, test, predict, etc. based on the continuous query model defined and application to the streamed data.

In an operation 906, a publish/subscribe (pub/sub) capability is initialized for ESPE 800. In an illustrative embodiment, a pub/sub capability is initialized for each project of the one or more projects 802. To initialize and enable pub/sub capability for ESPE 800, a port number may be provided. Pub/sub clients can use a host name of an ESP device running the ESPE and the port number to establish pub/sub connections to ESPE 800.

FIG. 10 illustrates an ESP system 1000 interfacing between publishing device 1022 and event subscribing devices 1024*a-c*, according to embodiments of the present technology. ESP system 1000 may include ESP device or subsystem 1001, event publishing device 1022, an event subscribing device A 1024*a*, an event subscribing device B 1024*b*, and an event subscribing device C 1024*c*. Input event streams are output to ESP device 1001 by publishing device 1022. In alternative embodiments, the input event streams may be created by a plurality of publishing devices. The plurality of publishing devices further may publish event streams to other ESP devices. The one or more continuous queries instantiated by ESPE 800 may analyze and process the input event streams to form output event streams output to event subscribing device A 1024*a*, event subscribing device B 1024*b*, and event subscribing device C 1024*c*. ESP system 1000 may include a greater or a fewer number of event subscribing devices of event subscribing devices.

Publish-subscribe is a message-oriented interaction paradigm based on indirect addressing. Processed data recipients specify their interest in receiving information from ESPE 800 by subscribing to specific classes of events, while information sources publish events to ESPE 800 without directly addressing the receiving parties. ESPE 800 coordinates the interactions and processes the data. In some cases, the data source receives confirmation that the published information has been received by a data recipient.

A publish/subscribe API may be described as a library that enables an event publisher, such as publishing device 1022, to publish event streams into ESPE 800 or an event subscriber, such as event subscribing device A 1024*a*, event subscribing device B 1024*b*, and event subscribing device C 1024*c*, to subscribe to event streams from ESPE 800. For illustration, one or more publish/subscribe APIs may be defined. Using the publish/subscribe API, an event publishing application may publish event streams into a running event stream processor project source window of ESPE 800, and the event subscription application may subscribe to an event stream processor project source window of ESPE 800.

The publish/subscribe API provides cross-platform connectivity and endianness compatibility between ESP application and other networked applications, such as event publishing applications instantiated at publishing device 1022, and event subscription applications instantiated at one or more of event subscribing device A 1024*a*, event subscribing device B 1024*b*, and event subscribing device C 1024*c*.

Referring back to FIG. 9, operation 906 initializes the publish/subscribe capability of ESPE 800. In an operation 908, the one or more projects 802 are started. The one or more started projects may run in the background on an ESP device. In an operation 910, an event block object is received from one or more computing device of the event publishing device 1022.

ESP subsystem 800 may include a publishing client 1002, ESPE 800, a subscribing client A 1004, a subscribing client B 1006, and a subscribing client C 1008. Publishing client 1002 may be started by an event publishing application executing at publishing device 1022 using the publish/subscribe API. Subscribing client A 1004 may be started by an event subscription application A, executing at event subscribing device A 1024*a* using the publish/subscribe API. Subscribing client B 1006 may be started by an event subscription application B executing at event subscribing device B 1024*b* using the publish/subscribe API. Subscribing client C 1008 may be started by an event subscription application C executing at event subscribing device C 1024*c* using the publish/subscribe API.

An event block object containing one or more event objects is injected into a source window of the one or more source windows 806 from an instance of an event publishing application on event publishing device 1022. The event block object may be generated, for example, by the event publishing application and may be received by publishing client 1002. A unique ID may be maintained as the event block object is passed between the one or more source windows 806 and/or the one or more derived windows 808 of ESPE 800, and to subscribing client A 1004, subscribing client B 806, and subscribing client C 808 and to event subscription device A 1024*a*, event subscription device B 1024*b*, and event subscription device C 1024*c*. Publishing client 1002 may further generate and include a unique embedded transaction ID in the event block object as the event block object is processed by a continuous query, as well as the unique ID that publishing device 1022 assigned to the event block object.

In an operation 912, the event block object is processed through the one or more continuous queries 804. In an operation 914, the processed event block object is output to one or more computing devices of the event subscribing devices 1024*a-c*. For example, subscribing client A 804, subscribing client B 806, and subscribing client C 808 may send the received event block object to event subscription device A 1024*a*, event subscription device B 1024*b*, and event subscription device C 1024*c*, respectively.

ESPE 800 maintains the event block containership aspect of the received event blocks from when the event block is published into a source window and works its way through the directed graph defined by the one or more continuous queries 804 with the various event translations before being output to subscribers. Subscribers can correlate a group of subscribed events back to a group of published events by comparing the unique ID of the event block object that a publisher, such as publishing device 1022, attached to the event block object with the event block ID received by the subscriber.

In an operation 916, a determination is made concerning whether or not processing is stopped. If processing is not stopped, processing continues in operation 910 to continue receiving the one or more event streams containing event block objects from the, for example, one or more network devices. If processing is stopped, processing continues in an operation 918. In operation 918, the started projects are stopped. In operation 920, the ESPE is shutdown.

As noted, in some embodiments, big data is processed for an analytics project after the data is received and stored. In other embodiments, distributed applications process continuously flowing data in real-time from distributed sources by applying queries to the data before distributing the data to geographically distributed recipients. As noted, an event stream processing engine (ESPE) may continuously apply the queries to the data as it is received and determines which entities receive the processed data. This allows for large amounts of data being received and/or collected in a variety of environments to be processed and distributed in real time. For example, as shown with respect to FIG. 2, data may be collected from network devices that may include devices within the internet of things, such as devices within a home automation network. However, such data may be collected from a variety of different resources in a variety of different environments. In any such situation, embodiments of the present technology allow for real-time processing of such data.

Aspects of the current disclosure provide technical solutions to technical problems, such as computing problems that arise when an ESP device fails which results in a complete service interruption and potentially significant data loss. The data loss can be catastrophic when the streamed data is supporting mission critical operations such as those in support of an ongoing manufacturing or drilling operation. An embodiment of an ESP system achieves a rapid and seamless failover of ESPE running at the plurality of ESP devices without service interruption or data loss, thus significantly improving the reliability of an operational system that relies on the live or real-time processing of the data streams. The event publishing systems, the event subscribing systems, and each ESPE not executing at a failed ESP device are not aware of or effected by the failed ESP device. The ESP system may include thousands of event publishing systems and event subscribing systems. The ESP system keeps the failover logic and awareness within the boundaries of out-messaging network connector and out-messaging network device.

In one example embodiment, a system is provided to support a failover when event stream processing (ESP) event blocks. The system includes, but is not limited to, an out-messaging network device and a computing device. The computing device includes, but is not limited to, a processor and a computer-readable medium operably coupled to the processor. The processor is configured to execute an ESP engine (ESPE). The computer-readable medium has instructions stored thereon that, when executed by the processor, cause the computing device to support the failover. An event block object is received from the ESPE that includes a unique identifier. A first status of the computing device as active or standby is determined. When the first status is active, a second status of the computing device as newly active or not newly active is determined. Newly active is determined when the computing device is switched from a standby status to an active status. When the second status is newly active, a last published event block object identifier that uniquely identifies a last published event block object is determined. A next event block object is selected from a non-transitory computer-readable medium accessible by the computing device. The next event block object has an event block object identifier that is greater than the determined last published event block object identifier. The selected next event block object is published to an out-messaging network device. When the second status of the computing device is not newly active, the received event block object is published to the out-messaging network device. When the first status of the computing device is standby, the received event block object is stored in the non-transitory computer-readable medium.

Figure 11:
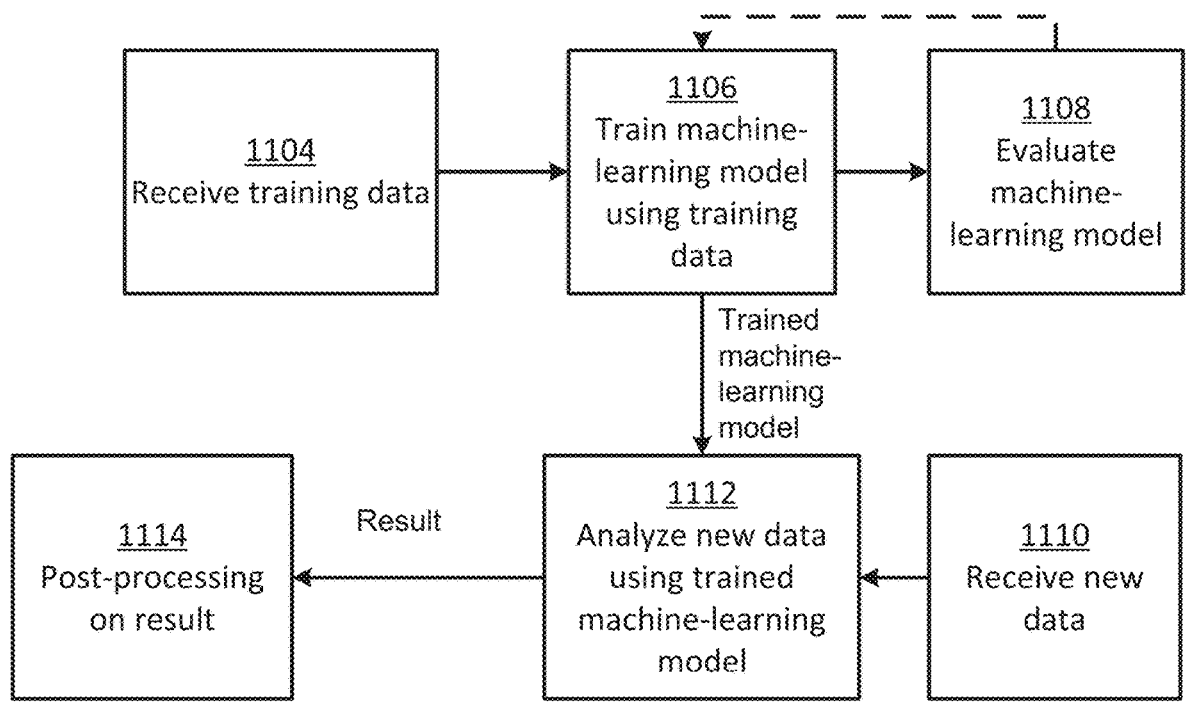
FIG. 11 illustrates a flow chart of an example of a process for generating and using a machine-learning model according to at least one embodiment of the present technology.

FIG. 11 is a flow chart of an example of a process for generating and using a machine-learning model according to some aspects. Machine learning is a branch of artificial intelligence that relates to mathematical models that can learn from, categorize, and make predictions about data. Such mathematical models, which can be referred to as machine-learning models, can classify input data among two or more classes; cluster input data among two or more groups; predict a result based on input data; identify patterns or trends in input data; identify a distribution of input data in a space; or any combination of these. Examples of machine-learning models can include (i) neural networks; (ii) decision trees, such as classification trees and regression trees; (iii) classifiers, such as Naïve bias classifiers, logistic regression classifiers, ridge regression classifiers, random forest classifiers, least absolute shrinkage and selector (LASSO) classifiers, and support vector machines; (iv) clusterers, such as k-means clusterers, mean-shift clusterers, and spectral clusterers; (v) factorizers, such as factorization machines, principal component analyzers and kernel principal component analyzers; and (vi) ensembles or other combinations of machine-learning models. In some examples, neural networks can include deep neural networks, feed-forward neural networks, recurrent neural networks, convolutional neural networks, radial basis function (RBF) neural networks, echo state neural networks, long short-term memory neural networks, bi-directional recurrent neural networks, gated neural networks, hierarchical recurrent neural networks, stochastic neural networks, modular neural networks, spiking neural networks, dynamic neural networks, cascading neural networks, neuro-fuzzy neural networks, or any combination of these.

Different machine-learning models may be used interchangeably to perform a task. Examples of tasks that can be performed at least partially using machine-learning models include various types of scoring; bioinformatics; cheminformatics; software engineering; fraud detection; customer segmentation; generating online recommendations; adaptive websites; determining customer lifetime value; search engines; placing advertisements in real time or near real time; classifying DNA sequences; affective computing; performing natural language processing and understanding; object recognition and computer vision; robotic locomotion; playing games; optimization and metaheuristics; detecting network intrusions; medical diagnosis and monitoring; or predicting when an asset, such as a machine, will need maintenance.

Any number and combination of tools can be used to create machine-learning models. Examples of tools for creating and managing machine-learning models can include SAS® Enterprise Miner, SAS® Rapid Predictive Modeler, and SAS® Model Manager, SAS Cloud Analytic Services (CAS)®, SAS Viya® of all which are by SAS Institute Inc. of Cary, N.C.

Machine-learning models can be constructed through an at least partially automated (e.g., with little or no human involvement) process called training. During training, input data can be iteratively supplied to a machine-learning model to enable the machine-learning model to identify patterns related to the input data or to identify relationships between the input data and output data. With training, the machine-learning model can be transformed from an untrained state to a trained state. Input data can be split into one or more training sets and one or more validation sets, and the training process may be repeated multiple times. The splitting may follow a k-fold cross-validation rule, a leave-one-out-rule, a leave-p-out rule, or a holdout rule. An overview of training and using a machine-learning model is described below with respect to the flow chart of FIG. 11.

In block 1104, training data is received. In some examples, the training data is received from a remote database or a local database, constructed from various subsets of data, or input by a user. The training data can be used in its raw form for training a machine-learning model or pre-processed into another form, which can then be used for training the machine-learning model. For example, the raw form of the training data can be smoothed, truncated, aggregated, clustered, or otherwise manipulated into another form, which can then be used for training the machine-learning model.

In block 1106, a machine-learning model is trained using the training data. The machine-learning model can be trained in a supervised, unsupervised, or semi-supervised manner. In supervised training, each input in the training data is correlated to a desired output. This desired output may be a scalar, a vector, or a different type of data structure such as text or an image. This may enable the machine-learning model to learn a mapping between the inputs and desired outputs. In unsupervised training, the training data includes inputs, but not desired outputs, so that the machine-learning model has to find structure in the inputs on its own. In semi-supervised training, only some of the inputs in the training data are correlated to desired outputs.

In block 1108, the machine-learning model is evaluated. For example, an evaluation dataset can be obtained, for example, via user input or from a database. The evaluation dataset can include inputs correlated to desired outputs. The inputs can be provided to the machine-learning model and the outputs from the machine-learning model can be compared to the desired outputs. If the outputs from the machine-learning model closely correspond with the desired outputs, the machine-learning model may have a high degree of accuracy. For example, if 90% or more of the outputs from the machine-learning model are the same as the desired outputs in the evaluation dataset, the machine-learning model may have a high degree of accuracy. Otherwise, the machine-learning model may have a low degree of accuracy. The 90% number is an example only. A realistic and desirable accuracy percentage is dependent on the problem and the data.

In some examples, if the machine-learning model has an inadequate degree of accuracy for a particular task, the process can return to block 1106, where the machine-learning model can be further trained using additional training data or otherwise modified to improve accuracy. If the machine-learning model has an adequate degree of accuracy for the particular task, the process can continue to block 1110.

In block 1110, new data is received. In some examples, the new data is received from a remote database or a local database, constructed from various subsets of data, or input by a user. The new data may be unknown to the machine-learning model. For example, the machine-learning model may not have previously processed or analyzed the new data.

In block 1112, the trained machine-learning model is used to analyze the new data and provide a result. For example, the new data can be provided as input to the trained machine-learning model. The trained machine-learning model can analyze the new data and provide a result that includes a classification of the new data into a particular class, a clustering of the new data into a particular group, a prediction based on the new data, or any combination of these.

In block 1114, the result is post-processed. For example, the result can be added to, multiplied with, or otherwise combined with other data as part of a job. As another example, the result can be transformed from a first format, such as a time series format, into another format, such as a count series format. Any number and combination of operations can be performed on the result during post-processing.

Figure 12:
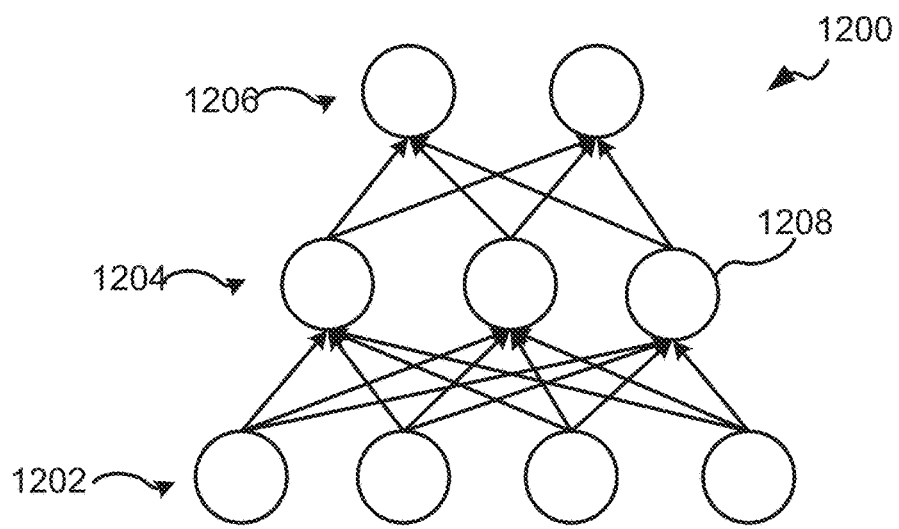
FIG. 12 illustrates an example of a machine-learning model as a neural network.

A more specific example of a machine-learning model is the neural network 1200 shown in FIG. 12. The neural network 1200 is represented as multiple layers of interconnected neurons, such as neuron 1208, that can exchange data between one another. The layers include an input layer 1202 for receiving input data, a hidden layer 1204, and an output layer 1206 for providing a result. The hidden layer 1204 is referred to as hidden because it may not be directly observable or have its input directly accessible during the normal functioning of the neural network 1200. Although the neural network 1200 is shown as having a specific number of layers and neurons for exemplary purposes, the neural network 1200 can have any number and combination of layers, and each layer can have any number and combination of neurons.

The neurons and connections between the neurons can have numeric weights, which can be tuned during training. For example, training data can be provided to the input layer 1202 of the neural network 1200, and the neural network 1200 can use the training data to tune one or more numeric weights of the neural network 1200. In some examples, the neural network 1200 can be trained using backpropagation. Backpropagation can include determining a gradient of a particular numeric weight based on a difference between an actual output of the neural network 1200 and a desired output of the neural network 1200. Based on the gradient, one or more numeric weights of the neural network 1200 can be updated to reduce the difference, thereby increasing the accuracy of the neural network 1200. This process can be repeated multiple times to train the neural network 1200. For example, this process can be repeated hundreds or thousands of times to train the neural network 1200.

In some examples, the neural network 1200 is a feed-forward neural network. In a feed-forward neural network, every neuron only propagates an output value to a subsequent layer of the neural network 1200. For example, data may only move one direction (forward) from one neuron to the next neuron in a feed-forward neural network.

In other examples, the neural network 1200 is a recurrent neural network. A recurrent neural network can include one or more feedback loops, allowing data to propagate in both forward and backward through the neural network 1200. This can allow for information to persist within the recurrent neural network. For example, a recurrent neural network can determine an output based at least partially on information that the recurrent neural network has seen before, giving the recurrent neural network the ability to use previous input to inform the output.

In some examples, the neural network 1200 operates by receiving a vector of numbers from one layer; transforming the vector of numbers into a new vector of numbers using a matrix of numeric weights, a nonlinearity, or both; and providing the new vector of numbers to a subsequent layer of the neural network 1200. Each subsequent layer of the neural network 1200 can repeat this process until the neural network 1200 outputs a final result at the output layer 1206. For example, the neural network 1200 can receive a vector of numbers as an input at the input layer 1202. The neural network 1200 can multiply the vector of numbers by a matrix of numeric weights to determine a weighted vector. The matrix of numeric weights can be tuned during the training of the neural network 1200. The neural network 1200 can transform the weighted vector using a nonlinearity, such as a sigmoid tangent or the hyperbolic tangent. In some examples, the nonlinearity can include a rectified linear unit, which can be expressed using the following equation:

$$y=\max(x,0)$$

where y is the output and x is an input value from the weighted vector. The transformed output can be supplied to a subsequent layer, such as the hidden layer 1204, of the neural network 1200. The subsequent layer of the neural network 1200 can receive the transformed output, multiply the transformed output by a matrix of numeric weights and a nonlinearity, and provide the result to yet another layer of the neural network 1200. This process continues until the neural network 1200 outputs a final result at the output layer 1206.

Other examples of the present disclosure may include any number and combination of machine-learning models having any number and combination of characteristics. The machine-learning model(s) can be trained in a supervised, semi-supervised, or unsupervised manner, or any combination of these. The machine-learning model(s) can be implemented using a single computing device or multiple computing devices, such as the communications grid computing system 400 discussed above.

Implementing some examples of the present disclosure at least in part by using machine-learning models can reduce the total number of processing iterations, time, memory, electrical power, or any combination of these consumed by a computing device when analyzing data. For example, a neural network may more readily identify patterns in data than other approaches. This may enable the neural network to analyze the data using fewer processing cycles and less memory than other approaches, while obtaining a similar or greater level of accuracy.

Some machine-learning approaches may be more efficiently and speedily executed and processed with machine-learning specific processors (e.g., not a generic CPU). Such processors may also provide an energy savings when compared to generic CPUs. For example, some of these processors can include a graphical processing unit (GPU), an application-specific integrated circuit (ASIC), a field-programmable gate array (FPGA), an artificial intelligence (AI) accelerator, a neural computing core, a neural computing engine, a neural processing unit, a purpose-built chip architecture for deep learning, and/or some other machine-learning specific processor that implements a machine learning approach or one or more neural networks using semiconductor (e.g., silicon (Si), gallium arsenide (GaAs)) devices. Furthermore, these processors may also be employed in heterogeneous computing architectures with a number of and a variety of different types of cores, engines, nodes, and/or layers to achieve various energy efficiencies, processing speed improvements, data communication speed improvements, and/or data efficiency targets and improvements throughout various parts of the system when compared to a homogeneous computing architecture that employs CPUs for general purpose computing.

Figure 13:
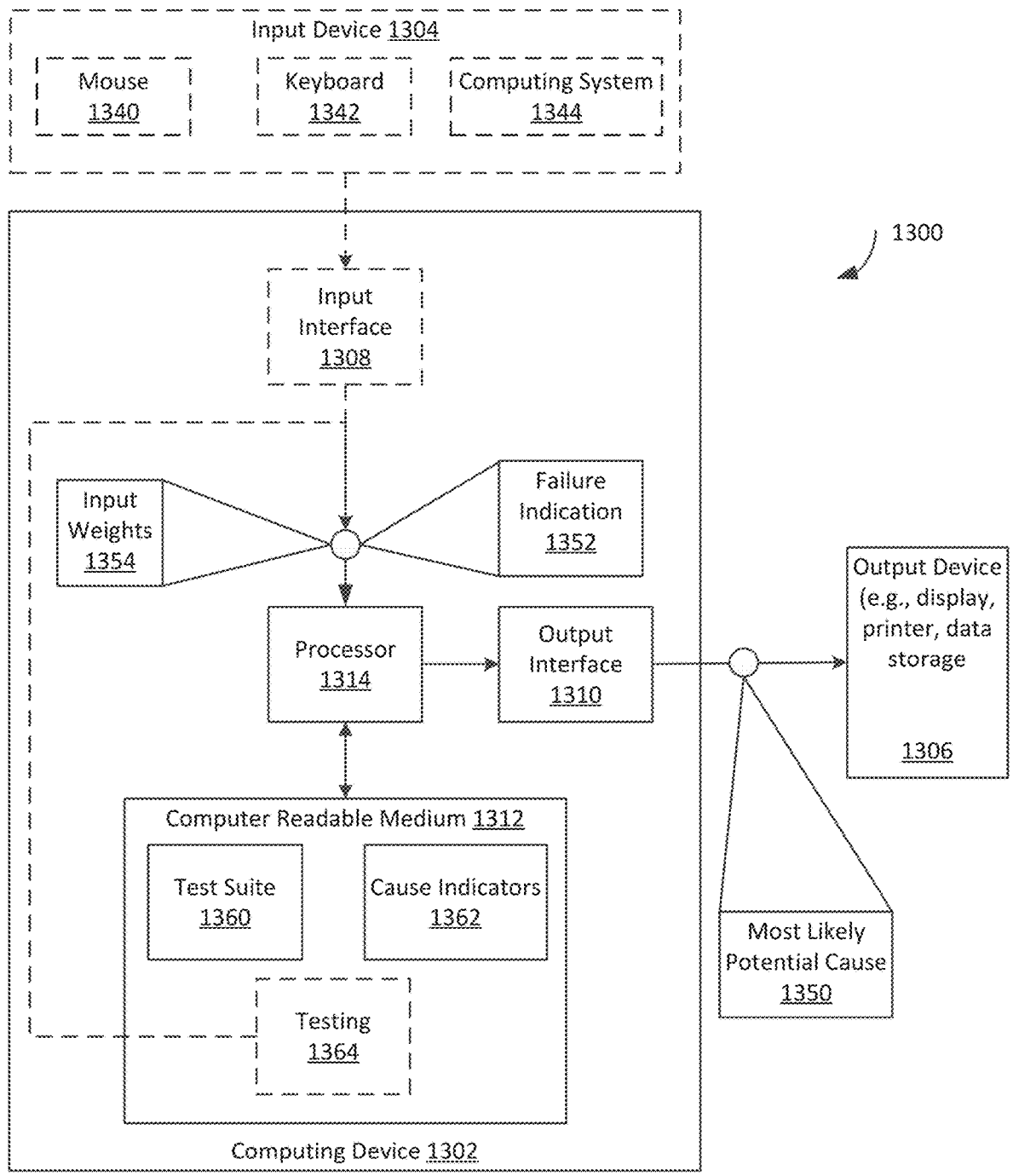
FIG. 13 illustrates an example block diagram of a system for outputting a most likely potential cause for a potential failure in at least one embodiment of the present technology.

FIG. 13 shows a block diagram of a system 1300 in at least one embodiment of the present technology. The system 1300 includes a computing device 1302 and an output device 1306. In one or more embodiments, the system 1300 includes other devices (e.g., input device 1304). The system is configured to exchange information between devices in the system (e.g., via wired and/or wireless transmission). For example, a network (not shown) can connect one or more devices of system 1300 to one or more other devices of system 1300. In one or more embodiments, the system 1300 is useful for outputting to output device 1306 a most likely potential cause 1350 for a potential failure of a complex system (not shown).

The computing device 1302 has a computer-readable medium 1312 and a processor 1314. Computer-readable medium 1312 is an electronic holding place or storage for information so the information can be accessed by processor 1314. Computer-readable medium 1312 can include, but is not limited to, any type of random access memory (RAM), any type of read only memory (ROM), any type of flash memory, etc. such as magnetic storage devices (e.g., hard disk, floppy disk, magnetic strips), optical disks (e.g., compact disc (CD), digital versatile disc (DVD)), smart cards, flash memory devices, etc.

Processor 1314 executes instructions (e.g., stored at the computer readable medium 1312). The instructions can be carried out by a special purpose computer, logic circuits, or hardware circuits. In one or more embodiments, processor 1314 is implemented in hardware and/or firmware. Processor 1314 executes an instruction, meaning it performs or controls the operations called for by that instruction. The term "execution" is the process of running an application or the carrying out of the operation called for by an instruction. The instructions can be written using one or more programming language, scripting language, assembly language, etc. Processor 1314 in one or more embodiments can retrieve a set of instructions from a permanent memory device and copy the instructions in an executable form to a temporary memory device that is generally some form of RAM, for example.

In one or more embodiments computer-readable medium 1312 stores instructions for execution by processor 1314. For example, computer-readable medium 1312 comprises instructions for a test suite application 1360 and cause indicators application 1362.

In one or more embodiments, the test suite application 1360 determines or generates a test suite that provides test cases for testing a complex system. This is useful, for instance, to identify a most likely potential cause 1350 for a potential failure of the system. Complex systems can include software, hardware, mechanical, chemical, biological components, combinations thereof, or computer-simulated models thereof. For example, a complex system could include an airplane as discussed in the background. As another example the test cases could be used to test a mobile phone with different hardware components (e.g., camera types) and different software configurations (e.g., display options and ringtone configurations). Test cases are used to test the mobile phone or a computer-simulation of the mobile phone to determine whether a particular display configuration with a particular camera could cause the mobile phone to fail (e.g., in taking a picture). In another example, the complex system could be a microwave oven and test cases are used to test whether the microwave oven fails (e.g., a control module of the microwave oven fails) when the power is set to one configuration (e.g. "High" or "Low") and the microwave oven receives a certain time input (e.g. 20 minutes or 30 minutes). In yet another example, the complex system could be a sprinkler fire system with different biological agents or chemical agents for corrosion prevention in the system with different piping and mechanical and/or electrical valve options for transporting the water in the sprinkler system. Test cases are used to test whether a particular chemical agent in combination with a particular piping could cause a particular valve to malfunction and the sprinkler system to fail (e.g., fail to initiate in the presence of a fire).

In one or more embodiments, the cause indictors application 1362 determines or generates cause indicators that represent a likelihood that a test condition or combination of test conditions of a test case of the test suite caused a failed test case. For example, in the case of a complex system that is a mobile phone as described above, if the mobile phone fails when taking a picture, a combination of the display option and camera type used when the mobile phone failed could have caused the mobile phone to fail. Alternatively, a combination of the display option and a ringtone configuration used when the mobile phone failed could have caused the mobile phone to fail, or a combination of a camera type and ringtone configuration. Cause indicators would represent the likelihood that it was the display option and camera type versus other possible combinations that caused the failed test case. For example, the cause indicator could be a probability or percentage.

In one or more embodiments, the computer readable medium 1312 also includes a testing application 1364 for testing a complex system according to the test suite and generating an indication of a failed test case. Testing could include testing the actual complex system or a computer-simulated environment modeling the complex system. The complex system is also referred to as a tested system or simply system. For simplicity, these terms to describe the complex system are used interchangeably herein. However, one of ordinary skill in the art will appreciate that a test system in one or more embodiments could be a model (e.g., a computer-simulated model) of the complex system.

In one or more embodiments, one or more applications stored on computer-readable medium 1312 are implemented in software (e.g., computer-readable and/or computer-executable instructions) stored in computer-readable medium 1312 and accessible by processor 1314 for execution of the instructions. The applications can be written using one or more programming languages, assembly languages, scripting languages, etc. The one or more application can be integrated with other analytic tools. As an example, test suite application 1360 and cause indicators 1362 are integrated data analytics software application and/or software architecture such as that offered by SAS Institute Inc. of Cary, N.C., USA. Merely for illustration, the applications are implemented using or integrated with one or more SAS software tools such as JMP®, Base SAS, SAS® Enterprise Miner™, SAS/STAT®, SAS® High Performance Analytics Server, SAS® Visual Data Mining and Machine Learning, SAS® LASR™ SAS® In-Database Products, SAS® Scalable Performance Data Engine, SAS® Cloud Analytic Services, SAS/OR®, SAS/ETS®, SAS® Inventory Optimization, SAS® Inventory Optimization Workbench, SAS® Visual Analytics, SAS® Viya™. SAS In-Memory Statistics for Hadoop®, SAS® Forecast Server, and SAS/IML® all of which are developed and provided by SAS Institute Inc. of Cary, N.C., USA.

One or more applications stored on computer-readable medium 1312 can be implemented as a Web application. For example, an application can be configured to receive hypertext transport protocol (HTTP) responses and to send HTTP requests. The HTTP responses may include web pages such as hypertext markup language (HTML) documents and linked objects generated in response to the HTTP requests. Each web page may be identified by a uniform resource locator (URL) that includes the location or address of the computing device that contains the resource to be accessed in addition to the location of the resource on that computing device. The type of file or resource depends on the Internet application protocol such as the file transfer protocol, HTTP, H.323, etc. The file accessed may be a simple text file, an image file, an audio file, a video file, an executable, a common gateway interface application, a Java applet, an extensible markup language (XML) file, or any other type of file supported by HTTP.

In one or more embodiments, fewer, different, and additional components can be incorporated into computing device 1302. For instance, in one or more embodiments, computing device 1302 further includes an input interface 1308. Processor 1314 operably couples with components of computing device 1302 (e.g., input interface 1308, with output interface 1310 and with computer readable medium 1312) to receive, to send, and to process information.

In one or more embodiments, the computing device 1302 receives information from input device 1304 via input interface 1308. In one or more embodiments, the input device 1304 is one or more devices for user entry (e.g. input weights 1354 and failure indication 1352) into the system 1300. For instance the input device 1304 could include one or more of a mouse 1340 or a keyboard 1342. Alternatively or additionally the input device 1304 includes a display, a track ball, a keypad, one or more buttons, a sensor, a phone, etc. For instance, one or more test engineers tests a physical complex system according to the test suite and inputs failure indication 1352 of a failed test case to the computing device 1302 (e.g., using mouse 1340 or keyboard 1342). In one or more embodiments, failure indication 1352 is multiple failure indications. In the same or different example, one or more test engineers inputs weights for the complex system (e.g., weights representing how likely it is that a given option for a given categorical factor will cause a failure of the complex system).

Alternatively, or additionally, input interface 1308 further provides an interface for receiving information from another device or machine such as a computing system 1344. For instance, in one or more embodiments, another computing system 1344 tests the complex system or a computer simulation of the complex system and generates one or more failure indications of a failed test case and sends failure indication 1352 to computing device 1302.

The computing device 1302 outputs information to output device 1306 via output interface 1310. Output interface 1310 provides an interface for outputting information (e.g., information representing a most likely potential cause 1350) for review by a user and/or for use by another application or device or multiple applications or devices (e.g., a display, printer, data storage).

In an alternative embodiment, the same interface supports both input interface 1308 and output interface 1310. For example, a touch screen provides a mechanism for user input and for presentation of output to the user. Alternatively, the input interface 1308 has more than one input interface that uses the same or different interface technology. Alternatively or additionally, the output interface 1310 has more than one output interface that uses the same or different interface technology.

In one or more embodiments, the computing device 1302 generates one or more input weights 1354 or one or more failure indications 1352. For instance, the testing of the complex system via the testing application 1364 can result in a failure indication 1352 or can be used to generate one or more input weights 1354. Alternatively or additionally, the computing device 1302 can generate default weights of the input weights 1354 (e.g., if an input weight is not received for a particular option via input interface 1308).

In one or more embodiments, the system 1300 implements a method as described herein (e.g., a method shown in FIG. 14) for outputting a most likely potential cause 1350 for a potential failure of the complex system.

Figure 14:
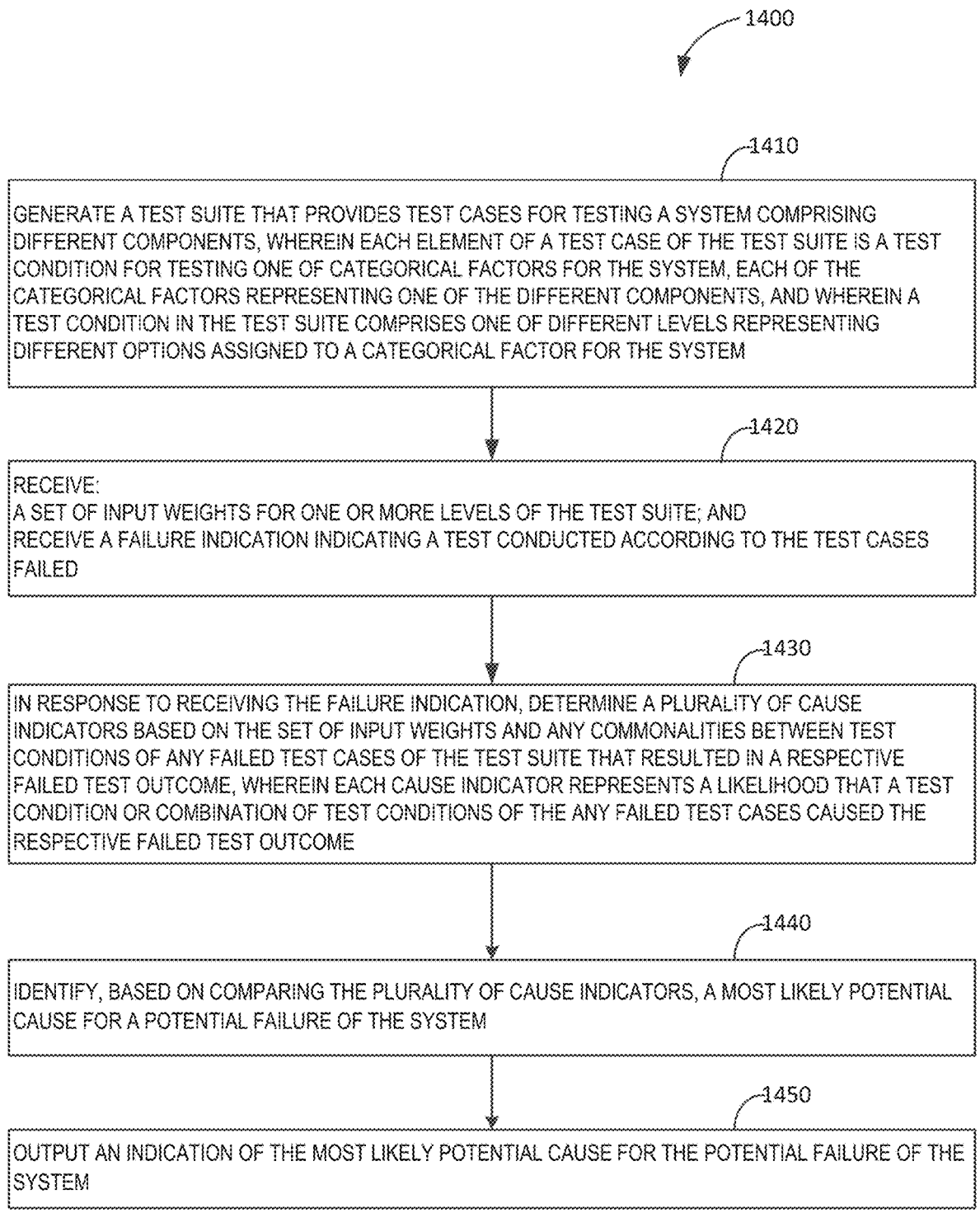
FIG. 14 illustrates an example flow diagram for outputting a most likely potential cause for a potential failure in at least one embodiment of the present technology.

FIG. 14 illustrates a flow diagram for a computer-implemented method 1400 that can be used to output an indication of the most likely potential cause for a potential failure of the system.

The method 1400 illustrates an operation 1410, in which a test suite is generated. In one or more embodiments, the test suite provides test cases for testing a system that has different components. The different components can be represented or referred to as categorical factors for the system. In one or more embodiments herein categorical factors are referred to as factors or inputs interchangeably. Different options for a component can be represented by different levels assigned to the categorical factor. In one or more embodiments, each element of a test case of the test suite is a test condition for testing one of categorical factors for the system. Each of the categorical factors represents one of the different components. A test condition in the test suite comprises one of different levels representing different options assigned to a categorical factor for the system. Typically, a categorical factor has different levels that represent discrete values or options for a component of the complex system in contrast to a continuous variable that describes a range of possible values or options. However, in one or more embodiments, levels of a categorical factor for the system are equivalence classes derived from continuous variables. Discrete values from a particular partitioned range of the possible values for the continuous variable are considered "equivalent" testing for other values in the range. For example, if the system is a software system, equivalence partitioning can be applied to input or output data of the software system to derive categorical factors for the software system.

The method 1400 illustrates an operation 1420 for receiving information. A set of input weights for one or more levels of the test suite is received. For example, a user in one or more embodiments provides the set of input weights. A failure indication is received. The failure indication indicates a test conducted according to the test cases failed.

The method 1400 illustrates an operation 1430 for determining cause indicators. In one or more embodiments, the cause indicators are determined in response to receiving the failure indication. The determined cause indicators are based on the set of input weights and any commonalities between test conditions of any failed test cases of the test suite that resulted in a respective failed test outcome. For example, in one or more embodiments, a same test condition is involved in multiple failed test cases. Each cause indicator represents a likelihood that a test condition or combination of test conditions of the any failed test cases caused the respective failed test outcome. In the same or different embodiments, cause indicators in a test case that received a failure indication are eliminated if they did not cause a failure in a different test case.

The method 1400 illustrates an operation 1440 for identifying, based on comparing the cause indicators, a most likely potential cause for a potential failure of the system. The method 1400 illustrates an operation 1450 in which an indication of the most likely potential cause for a potential failure of the system is output. In one or more embodiments, the indication is part of an ordered ranking of potential causes for a potential failure of the system. In one or more embodiments, one or more of the potential causes precipitated an actual failure of the tested system or a model of the test system. In one or more embodiments, this indication is used for further testing, which may cause the potential failure, and/or for refraining from design a complex system, which may cause the potential failure.

Figure 15:
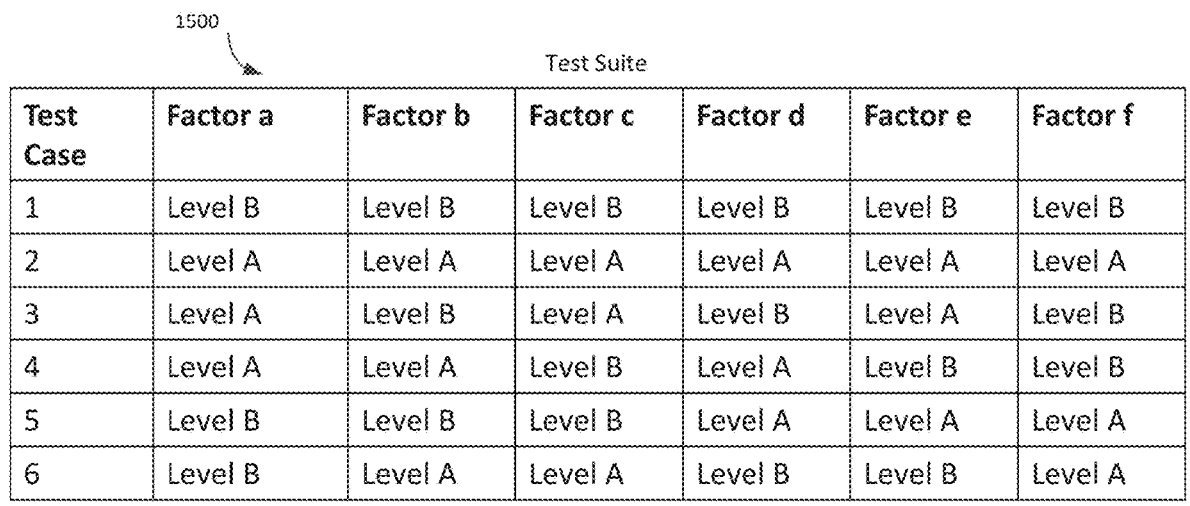
FIG. 15 illustrates an example test suite in some embodiments of the present technology.

FIG. 15 shows an example test suite 1500 according to embodiments herein. In one or more embodiments shown in FIG. 15, a test suite is a covering array. Covering arrays are useful tools to determine test cases for testing complex engineered systems.

One reason covering arrays are attractive for this purpose is that they are an efficient way to construct test cases that are effective at precipitating failures that are due to the combination of several inputs. Testing complex systems is a difficult undertaking, where test engineers are tasked with constructing a set of test cases that can efficiently identify faults in the system. The engineers are usually expected to work within tight time, computational and resource constraints. Covering arrays ensure that all possible combinations among t categorical factors or inputs appear in a test suite, where t is known as the strength of the covering array.

FIG. 15 shows a test suite 1500 that is a covering array of strength two where each input or categorical factor (factors a-f) has two levels (Level A and Level B). This means that each of the factors or components of a complex system can be one of two options.

Alternatively or additionally, a test suite is another type of array. For example, the array in one or more embodiments is an orthogonal array in which each possible combination occurs the same amount of times (e.g., only once). In one or more embodiments, the array is a randomly generated array with random combinations. In one or more embodiments, the array is generated based on previous failed test cases. In one or more embodiments, a test suite can be referred to as an array D with n rows and l columns. Let column i have $s_i$ levels for i=1, . . . , l. D is said to be a covering array of strength t if any subset of t columns has the property that all $\Pi\, s_i$ level combinations occur at least once.

Covering arrays have been shown to be effective as a means of identifying suites of test cases for testing complex engineered systems. A software system is an example of such a complex engineered system. In one or more embodiments, each row of the array represents one of the test cases and each column of the array represents one of the categorical factors. For instance, as shown in FIG. 15 the inputs of the system are mapped to the columns of test suite 1500 and the levels of the columns are mapped to the allowed values of the corresponding inputs. The rows of the test suite 1500 are the test cases of test suite 1500. Alternatively, each column of a test suite represents one of the test cases and each row of the test suite represents one of the categorical factors.

Given a test suite derived from a covering array, if all the test cases result in a pass (e.g., produce a success indication and/or the expected result), then the test engineer can ascertain that there are no faults due to combinations of inputs involving t or fewer inputs. However, if there are failures, the test engineer is faced with the task of identifying the particular inputs and their level combinations that precipitated the failures. For instance, there is empirical evidence that nearly all faults are due to some combination of values for five or fewer inputs.[1] For many systems, devising a test suite for the system is only the beginning. If a failure is discovered, the test engineer typically wants to know which combination of inputs and associated levels induced the failure. This is known as the fault location problem. This problem can also be referred to as a failure localization problem. The number of combinations makes it difficult or even infeasible to determine a list of potential causes without using a computing approach.

[1] D. R. Kuhn, D. R. Wallace, and A. M. Gallo, "Software fault interactions and implications for software testing," *IEEE Transactions on Software Engineering*, vol. 30, no. 6, pp. 4 I 8-42 I, June 2004.

There are two categories of computing approaches to the fault location problem: exact approaches and stochastic (or probabilistic) approaches. In the simplest form in an exact approach, for combinations involving f inputs, the exact computing method starts with all input combinations involved in test cases that induce a failure, and removes input combinations that appear in the test suite for test cases in which a failure did not occur. The value of (investigated is the smallest value for which the set of potential causes is non-empty. A stochastic computing approach instead uses modeling techniques and statistics to investigate and determine a set of potential causes.

One or more embodiments described herein are an improvement on these traditional computing approaches to the fault location problem. Further this improved computing approach allows modification of the computing based on a test engineer's knowledge of the system. For example, a test engineer typically has prior knowledge of the system, through particular inputs, or combinations of inputs, that may have been problematic in the past when testing a system, or with recent changes to the complex system that may not have been rigorously tested. One or more embodiments provides a method for specifying prior knowledge of inputs and levels in a computing approach to the analysis of a test suite when failures are discovered. This analysis provides a ranking of potential causes for investigating potential causes.

Figure 16A:
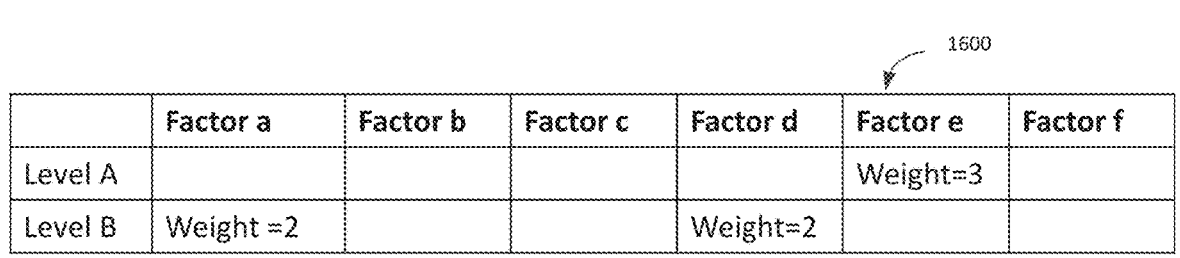
FIG. 16A illustrates an example set of input weights in at least one embodiment of the present technology.

FIGS. 16A-16D are applicable to an example test scenario with 6 inputs (factors a-f), each having two levels (Level A and Level B). FIG. 16A shows an example of representing or quantifying prior knowledge as a set of input weights 1600 for particular inputs and levels (factor a, level B; factor d, level B; and factor e, level A). In one or more embodiments, the weights are all greater than or equal to a predefined threshold and/or a baseline weight. In this example shown in FIG. 16A, define $w_i(j) \geq 0$ as the weight of level j for input i, for j=1, ..., $s_j$. While any positive weight in this example can be assigned, for simplicity a baseline weight for any non-provided weight $w_i[j]$ is set to be 1. If level j of input i is assumed more likely to be involved in a failure based on prior knowledge, $w_i[j]$ should be assigned a value greater than 1 as shown in FIG. 16A. A weight of less than 1 is used for levels that are known to be less problematic. A value of 0 can be assigned to a $w_i[j]$, if it is known with absolute certainty that a failure cannot occur due to any interactions that include level j for input i. The weight $w_i[j]$ can be thought of as how much more (or less) likely level j for input i may lead to a failure compared to a baseline input having weight 1.

Based on previous testing, level A of factor e is known to be problematic, as is level B of input a and level B of factor d, but to a lesser extent. The test engineer assigns the highest weight of 3 to level A of factor e, and higher weights of 2 to level B of input a and level B of factor d. The remaining weights are set at the baseline value of 1. FIG. 16C shows an example of weights 1640 assigned to all of the factors and levels for the tested system by assigning a default or baseline weight of 1 to each of the remaining factors.

Figure 16B:
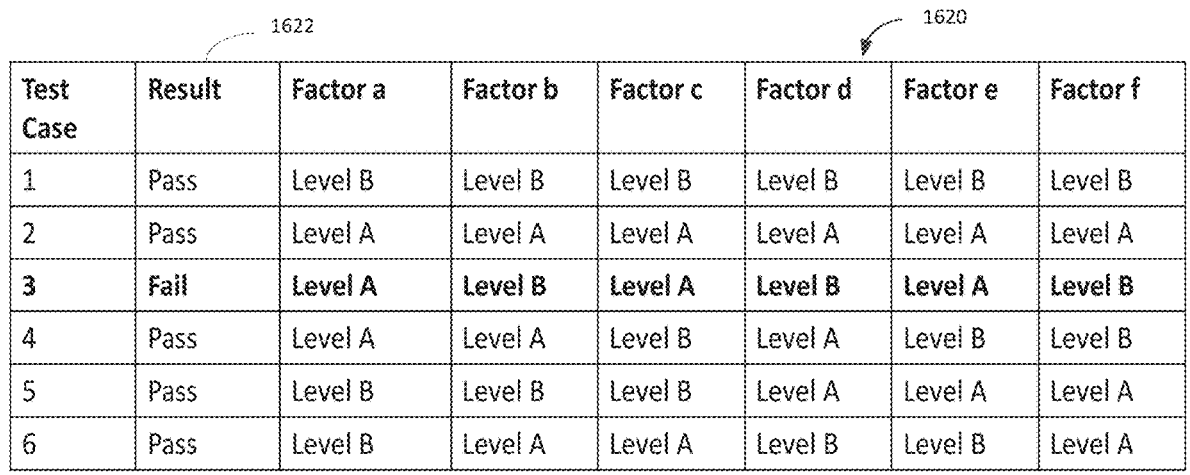
FIG. 16B illustrates an example single failed test outcome of a test suite in at least one embodiment of the present technology.

FIG. 16B presents the results 1620 of testing a test suite 1500 that is a strength 2 covering array, where each input has 2 levels. The outcome of each test case is presented in the results column 1622. Only one test case, test case 3 resulted in a failure indication or "Fail" in results column 1622. The other test cases resulted in a success indication or "Pass" in results column 1622. Since each factor and level of test case 3 is represented in a passed test, the failure is due to a combination of factors. The failure due to test case 3 has six potential causes of a failure for the test system involving combination of two factors. In other examples, a single factor and level is common to several failed test cases, and would be a potential cause. In this case, if it is a strength 2 covering array, the single factor and level would be the only potential cause.

FIG. 16D presents a table 1660 of the potential causes of a potential failure for the test system involving combination of two factors. Input column 1662 presents a first factor (Factor 1) of a given level (Level 1) of the combination and Input column 1664 presents a second factor (Factor 2) of a given level (Level 2) of the combination. The weights 1640 do not themselves provide sufficient information for determining what combination of factors is the most likely potential cause. A cause indicator is computed for each of the combinations, with a cause indicator value assigned for each in Cause Indicator column 1666.

In this example shown in FIG. 16D, the value assigned to each cause indicator is a multiplication of the individual weights for the levels of each of the factors that make up the combinations. For instance, a value for the combination of input $i_1$ at level $j_1$ and input $i_2(i_1 \neq i_2)$ at level $j_2$ is represented as $w_{i_1 i_2}(j_1, j_2)$. The weight of $w_{i_1 i_2}(j_1, j_2)$ is computed as $$w_{i_1 i_2} = w_{i_1}(j_1) w_{i_2}(j_2), \quad (1)$$

where $j_1 \in 1, \ldots, s_{i_1}$, and $j_2 \in 1, \ldots, s_{i_2}$.

Equation (1) does not preclude the test engineer from changing the value of $w_{i_1 i_2}(j_1, j_2)$. In one or more embodiments, the test engineer inputs a value for a combination with the set of input weights or knowledge about particular combinations can be reflected by using a different value for $w_{i_1 i_2}(j_1, j_2)$. Assuming baseline weights of 1, values of $w_{i_1 i_2}(j_1, j_2)$ greater than 1 indicate combinations more likely to induce a failure, while a value less than 1 indicates combinations less likely to induce a failure for determining an ordered ranking and/or a most likely potential cause for a failure of the system.

Cause indicators in Cause Indicator column 1666 can be compared (e.g., to provide an ordered ranking). Alternatively or additionally a normalized weight is computed as shown in Normalized Weight column 1668 for a cause indicator in order to provide an ordered ranking. As shown in FIG. 16D, the normalized weights in the Normalized Weight column 1668 are generated by normalizing any weights assigned to one or more levels or weights assigned to a combination of one or more levels such that each normalized weight is greater than zero and a sum of the normalized weights is one and assign one of the normalized weights to each of the plurality of cause indicators. For example, in FIG. 16D the sum total of all of the cause indicator values in the Cause Indicator column 1666 is 14, so a normalized weight in the Normalized Weight column 1668 is the value in the Cause Indicator column 1666 divided by the sum total (i.e. 14) of all of the cause indicator values.

Based on this analysis, instead of treating all combinations equally likely to have caused the failure, the most likely candidate based on either the Cause Indicator column 1666 or Normalized Weight column 1668 is combination 1670 followed by combination 1672, followed by combination 1674. The remaining potential causes are equally likely. This allows the test engineer to focus on combination 1670 and combination 1672 (e.g., by further testing of combination 1670 and combination 1672) before needing to consider any other combinations (e.g., further testing of combination 1674).

The example shown in FIGS. 16A-16D resulted in a single failed test and assumed that a combination of 2 inputs (i.e. Factor 1 (Level 1) and Factor 2 (Level 2)) is the source of the failed test and thus a potential cause for a potential failure for the system. In other embodiments, the set of potential causes includes a different number of inputs and/or the number of failed tests. In one or more embodiments, to determine the set of potential causes $\psi_k(m)$ involving k inputs given a failure in test case m, determine if all combinations of size k in test case m appear elsewhere in the test suite in a test case that passed. If a combination did pass elsewhere, it is not a potential cause, otherwise it belongs in $\psi_k(m)$ as a potential cause. If all combinations involving k inputs have passed in the test suite, then consider combinations involving k+1 inputs, and so on, until the set of potential causes is not empty. If there is more than one failure, it is also important to determine if an element in $\psi_k(m)$ occurs in $\psi_k(m')$ where $m \neq m'$.

In the simplest case, assume that test case m results in a failure and all potential causes in $\psi_k(m)$ only occur in test case m. Denoting $C_{i_1 i_2}(j_1, j_2)$ as the combination of level $j_1$ for input $i_1$ and level $j_2$ for input $i_2$ with associated weight $w_{i_1 i_2}(j_1, j_2)$, then for $C_{i_1 i_2}(j_1, j_2) \in \psi_k(m)$, the probability that $C_{i_1 i_2}(j_1, j_2)$ is the cause, $P[C_{i_1 i_2}(j_1, j_2)|\psi_k(m)]$, can be calculated as $$P[C_{i_1 i_2}(j_1, j_2)|\psi_k(m)] = \frac{w_{i_1 i_2}(j_1, j_2)}{\sum_{C_{a_1 a_2}(b_1, bj_2) \in \psi_k(m)} w_{a_1 a_2}(b_1, bj_2)}, \quad (2)$$

where $$P[C_{i_1 i_2}(j_1, j_2)|\psi_k(m)] = 0 \text{ if } C_{i_1 i_2}(j_1, j_2) \notin \psi_k(m).$$

Simply put, if there is a single failure, the likelihood of a particular combination being the cause is the weight for that combination divided by the sum of the weights for all combinations in $\psi_k(m)$. There are two underlying assumptions in using Equation (2): i) that the failure is not caused by a combination of greater than k inputs, and ii) if it is due to a combination of k inputs, there is only one cause for the failure in test case m.

The example presented in FIGS. 16A-16D is a simple example, and yet there are still six potential causes for the single failure. As the number of inputs grows and test suites become larger, the resulting increase in the number of potential causes is an issue that test engineers must deal with. A ranking provided by embodiments herein makes such situations manageable.

Figure 17A:
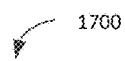
FIG. 17A illustrates an example set of input weights in at least one embodiment of the present technology.

FIGS. 17A-17G present an example case in which there are two failed test cases for the test suite 1500 in FIG. 15, which shows a covering array of strength two with 6 inputs (factors a-f) each having two levels. FIG. 17A shows input weights 1700 entered, in this example embodiment, for every one of the potential inputs.

Figure 17B:
FIG. 17B illustrates example multiple failed test outcomes of a test suite in at least one embodiment of the present technology.

FIG. 17B presents the results 1710 of testing a test suite 1500. The outcome of each test case is presented in the results column 1712. In this example, two test cases, test cases 4 and 5 resulted in a failure indication or "Fail" in results column 1712. The other test cases resulted in a success indication or "Pass" in results column 1712.

Analyzing the failures, for each test case there is a different list of potential causes as shown in FIGS. 17C and 17D. FIG. 17C shows a table 1720 of the potential causes 1722 for test case 4 along with computed or combined weights 1724. The combined weights 1724 are calculated using the input weights of FIG. 17A in Equation (1). FIG. 17D shows a table 1730 of the potential causes 1732 for test case 5 along with their combined weights 1734 as calculated using the input weights of FIG. 17A in Equation (1). While the combined weights are based on the input weights 1700 Tables 1720 and table 1730 do not account for commonalities between test cases.

When the results of a test suite have more than one test case with a failure, and a potential cause occurs in multiple test cases, additional care is taken in determining the relative likelihood a test condition will cause a failure (e.g., considering any commonalities between test conditions of failed test cases). Intuitively, if there are multiple failures and there are potential causes that are common to the multiple test cases, it is more likely that the failures are due to the common cause than distinct causes from the sets of potential causes for each failure. To account for this in one or more embodiments, a joint probability mass function, treating the test cases in which failures occur as random variables, is used to determine a value assigned to a cause indicator.

FIGS. 17E-17G show cause indicators determined based on the combined weight and commonalities between test conditions of failed test cases 4 and 5. Table 1740 in FIG. 17E shows cause indicators 1742 for test case 4 taking into account test case 5. Table 1750 in FIG. 17F shows cause indicators 1752 for test case 4 taking into account test case 5. For example, combination 1770 is common to both table 1740 in FIG. 17E and table 1750 in FIG. 17F. The cause indicators in tables 1740 and 1750 are computed to form a basis for comparison between all the cause indicators for the test cases. As shown, the computations for both tables result in a same cause indicator value for the combination 1770. FIG. 17G shows a single ordered ranking of all the potential causes and cause indicators from tables 1740 and tables 1750. FIG. 17G can also be considered a union of the set of potential causes in table 1740 and table 1750.

In general, a set of potential causes involving k inputs given a failure in test case m is denoted by $\psi_k(m)$. In the case of two failures as shown in FIGS. 17A-17G, where at least one potential cause is common to both test cases (e.g., combination 1770) with failures, define $\psi_k$ for all the test cases as the set $\{\psi_k(m_1 \cup \psi_k m_2)\}$ where test cases $m_1$ and $m_2$ result in failures (e.g., test cases 4 and 5 of FIG. 17B), and at least one potential cause exists in both $\psi_k(m_1)$ and $\psi_k(m_2)$ (e.g., combination 1770).

If failures have been observed for two test cases $m_1$ and $m_2$, and failures are due to two-input combinations, there are two different possibilities to consider to determine the cause indicators (e.g., via a joint probability mass function):
1) A single potential cause that exists in both $\psi_2(m_1)$ and $\psi_2(m_2)$ caused the failure for both test cases.
2) A potential cause in $\psi_2(m_1)$ that is not in $\psi_2(m_2)$ caused the failure for test case $m_1$, and a potential cause in $\psi_2(m_2)$ that is not in $\psi_2(m_1)$ caused the failure for test case $m_2$.

In FIGS. 17E-17G, the combination 1770 appears in both test cases with a failure. As shown in FIGS. 17C and 17D, the combined weight calculated for this combination 1770 is small (a combined weight of 1) relative to the other potential causes. However, because it is a potential cause in both test cases, it becomes a question of whether or not it is more likely than two independent causes from different test cases. That is, what is the probability a given single cause or pair of independent causes result in failures, conditional on observing failures in test cases.

In one or more embodiments, the cause indicators for individual test cases are computed to form a basis for comparison for outputting a most likely potential cause for a potential failure of the system. To find the most likely potential causes for further investigation, the computed probabilities account for the input weights 1700 and commonalities between test conditions of failed test cases (i.e. combination 1770).

To provide a method for comparison, a probability is defined that one would expect to see a failure for any given combination, prior to knowing that any failure has occurred. As an example, the probability is computed as shown in Equation 3:

$$P[C_{i_1 i_2}(j_1, j_2)] = \frac{w_{i_1 i_2}(j_1, j_2)}{\sum_{a_1 < a_2} \sum_{b_1=1}^{s_{a_1}} \sum_{b_2=1}^{s_{a_2}} w_{a_1 a_2}(b_1, b_2)} \text{ for} \quad (3)$$

$$j_1 = 1, \ldots, s_{i_1}, j_2 = 1, \ldots, s_{i_2}, \text{ and } 1 \leq i_1 < i_2 \leq n.$$

Assuming that a two-input combination caused the failure, to find the probability of observing failures for $m_1$ and $m_2$, one considers the combination of configurations in $\psi_k$ that would lead to failures for $m_1$ and $m_2$. The probability of observing failures for $m_i$ and $m_2$, $P[|\psi_k]$, can be calculated as the probability that a single combination caused the failure, P[single cause], plus the probability that there are two independent failures, P[two causes]. For each single cause, the probability that it causes a failure can be calculated from Equation (3). Then the probability that a single cause leads to the failures is simply $$P[\text{single cause}] = \Sigma_{C_{i_1 i_2}(j_1, j_2) \in \psi_2(m_1) \& \psi_2(m_2)} P[C_{i_1 i_2}(j_1, j_2)] \quad (4)$$

In the case of two different causes leading to failures on separate test cases, these occur independently of one another, so to calculate the probability of a particular combination of two different causes requires multiplying the two individual probabilities. Taking the summation of those different combinations, $$P[\text{two causes}] = \sum_\theta P[C_{i_1 i_2}(j_1, j_2)] P[C_{i_3 i_4}(j_3, j_4)] \quad (5)$$

where $$\theta = \{C_{i_1 i_2}(j_1, j_2) \in \psi_2(m_1) \& \notin \psi_2(m_2),$$
$$C_{i_3 i_4}(j_3, j_4) \notin \psi_2(m_1) \& \in \psi_2(m_2)\}.$$

Combining (4) and (5), $$P[\psi_k] = P[\text{single cause}] + P[\text{two causes}]. \quad (6)$$

For analysis, the probability that a given combination or set of combinations precipitated the failures is determined, given the set of potential causes in which there were observed failures in the particular test cases that generated the set of potential causes. For a potential cause that is common to the two test cases, the probability by Bayes' Theorem that the combination precipitated the failure is then $$P[C_{i_1 i_2}(j_1, j_2) | \psi_k] = \frac{P[C_{i_1 i_2}(j_1, j_2)]}{P[\psi_k]} \quad (7)$$

since $P[\psi_k | C_{i_1 i_2}(j_1, j_2)] = 1$. For a combination $C_{i_1 i_2}(j_1, j_2) \in \psi_2(m_1)$ and $\in \psi_2(m_2)$ and $C_{i_3 i_4}(j_3, j_4) \in \psi_2(m_1)$ and $\in \psi_2(m_2)$, the probability the two independent causes precipitated the two failures on different test cases is $$P[C_{i_1 i_2}(j_1, j_2) \cap \psi_k C_{i_3 i_4}(j_3, j_4) | \psi_k] = \quad (8)$$
$$\frac{P[C_{i_1 i_2}(j_1, j_2)] P[C_{i_3 i_4}(j_3, j_4)]}{P[\psi_k]}$$

Through (7) and (8), there is a joint probability mass function for the two failures. If a test engineer wants to focus on the cause for a particular test case, the marginal probability can be calculated by taking the sum of the probabilities in Equation (8) involving the possible combinations from the other test case where a failure occurred.

As an example, the calculation for the cause indicators for combination 1770 and combination 1780 in FIGS. 17E and 17G are calculated. For both cause indicators, $P[\psi_k]$ is computed. Using Equation (4), the only single cause or cause in common to both failed test cases is combination 1770, i.e. the combination of c(B) and d(A).

$$P[\text{single cause}] = P[c(B), d(A)] = 1/146 = 146/21316,$$

while for the remaining potential causes, using Equation (5), $$P[\text{two causes}] = 208/21316.$$

Combining these, from Equation (6), $$P[\psi_k] = P[\text{single cause}] + P[\text{two causes}] = 354/21316.$$

Each of the cause indicators in FIGS. 17E-17G is computed as a conditional probability using Equation (7). For combination 1770, the cause indicator can be defined as:

$$P[c(B), d(A) | \psi_k] = \frac{P[c(B), d(A)]}{P[\psi_k]} = \frac{146/21316}{354/21316} = 146/354$$

Each of the other combinations in FIGS. 17E-G (e.g., combination 1780 and combination 1790) would be independent causes of a failure. This means that different combinations one in each of test cases 4 and 5 caused the respective test case failure. As an example, the cause indicator for combination 1780 is computed taking into account each of the other single cause combinations in FIG. 17F. Combination 1780 is a first single cause combination in FIG. 17E corresponding to factor/level combinations of a(A), c(B). Combination 1790 is a first single cause combination in FIG. 17F corresponding to factor/level combinations of a(B), d(A). Each of these combinations had a weight of 2 as opposed to 1 for combination 1770 as shown in FIGS. 17C and 17D. The probability that these two combinations caused the failures, is computed as:

$$P[a(A), c(B)] \cap P[a(B), d(A)] = \frac{2}{146} * \frac{2}{146} = \frac{4}{21316}$$

The conditional probability then that combination 1780 and combination 1790 caused a failure is then computed using Equation (8):

$$\frac{P[a(A), c(B) \cap a(B), d(A)]}{P[\psi_k]} = \frac{4/21316}{354/21316} = 4/354$$

Each of the remaining probabilities of a failure involving combination 1780 and each of the other independent causes of failure in FIG. 17F is computed similarly. To compute then the cause indicator or P[a(A),c(B)]] for combination 1780, each of these individual probabilities is summed.

$$P[a(A), c(B)]] = \frac{4}{354} + \frac{12}{354} + \frac{4}{354} + \frac{4}{354} + \frac{6}{354} + \frac{2}{354} = \frac{32}{354}$$

As demonstrated in FIGS. 17A-17G, and this example calculation when one or more cause(s) appear for multiple failures, they tend to be the most likely potential cause compared to independent causes for different failures even if an individual cause is weighted higher. That is what intuitively one would expect if failures are rare.

From a practical standpoint, it is often preferable to present potential causes from multiples test cases separately from the unique occurrences. That is, do a weighted comparison of the potential causes appearing in multiple test cases first. If it is discovered that none of the multiple-test case potential causes are a cause, then the test engineer can examine a weighted analysis on the remaining potential causes unique to each test case. If there are more than two failures, this approach is more tractable than generating the joint probability mass function for the multiple failure test cases.

Figure 18:
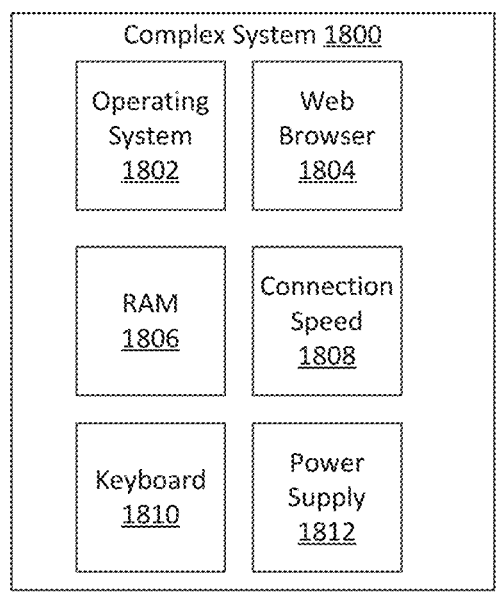
FIG. 18 illustrates an example complex system in at least one embodiment of the present technology.

FIG. 18 illustrates an example complex system 1800 in at least one embodiment of the present technology. The complex system 1800 has many different components or features. For instance, the complex system 1800 comprises software programs (e.g. an operating system 1802) and computer hardware (e.g. keyboard 1810) and other components including a web browser 1804, a RAM 1806, a connection speed 1808, and a power supply 1812. Each of these components is present in the complex system 1800, but a given component takes on different forms or properties depending on options selected by the designer of the complex system. For example, the operating system 1802 could be one of many different types including Windows® or Linux®. The web browser 1804 could be Safari®, Internet Explorer®, Firefox®, or Chrome™. The RAM 1806 could be 4, or 8 MB. The connection speed 1808 could have many different settings leading to different connection speeds including 0-1 Mbps or 1-5 Mbps. The keyboard 1810 could be wireless handheld or wired. The power supply 1812 could have different efficiencies including 80% or 90%. Any one of these features or options alone or in combination with another feature or option of another component could cause a failure in the complex system 1800 if it were designed with that particular combination.

Figure 19:
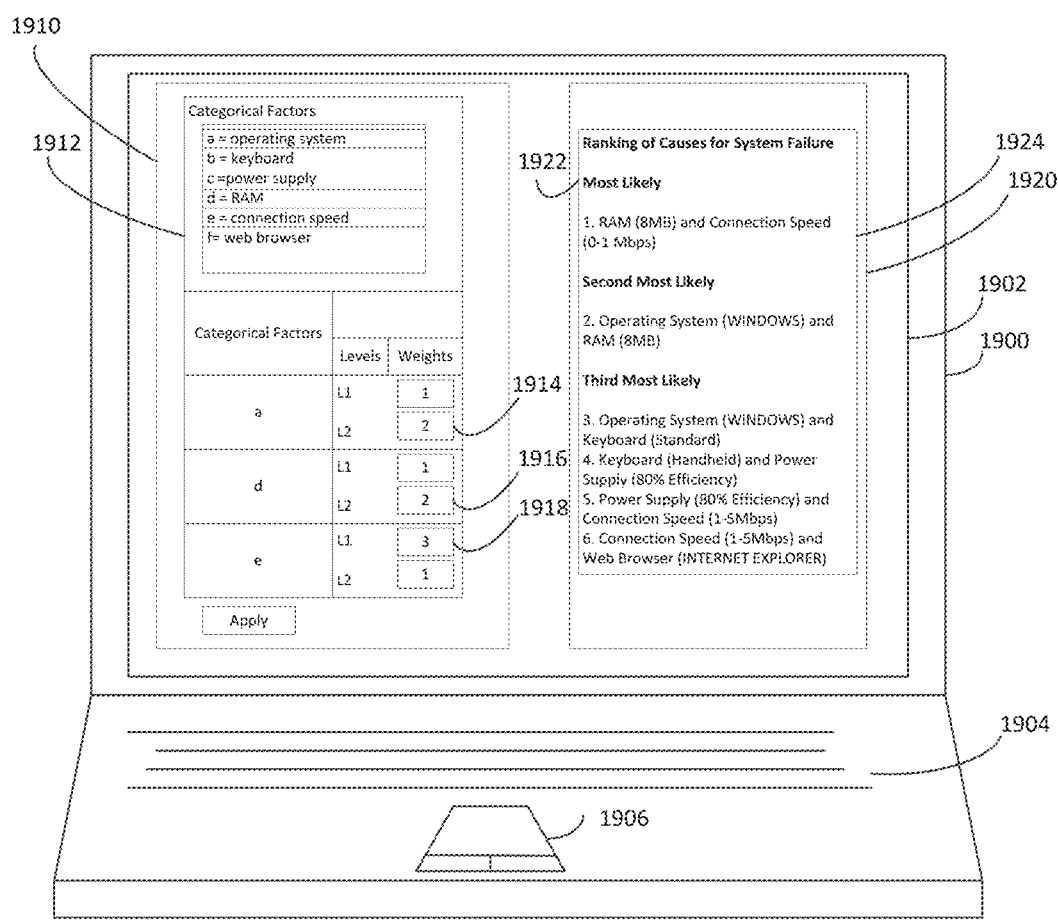
FIG. 19 illustrates an example graphical user interface displaying a most likely potential cause for a potential failure in at least one embodiment of the present technology.

FIG. 19 illustrates an example graphical user interface for displaying an indication of the most likely potential cause for the potential failure of complex system 1800. FIG. 19 shows a computing device 1900 with an integrated display device 1902. The display device 1902 displays a first graphical user interface 1910. The components of the system are represented as categorical factors 1912. In one or more embodiments, the user inputs the particular categorical factors or a number of categorical factors in a same or different interface than graphical user interface 1910. Alternatively or additionally, the user inputs particular levels or a number of levels for the categorical factors in a same or different interface than graphical user interface 1910. In one or more embodiments, the graphical user interface 1910 as shown allows for selection of particular categorical factors 1912 for entry of particular weights for one or more levels assigned to the categorical factor.

As shown in FIG. 19, the graphical user interface 1910 displays text boxes for entry of weights for particular levels of the selected ones of categorical factors 1912. The user sets particular weights in text boxes 1914, 1916, and 1918. For instance, a categorical factor a of L2 corresponds to an operating system of Linux® and has a corresponding text box 1914. A categorical factor d of L2 corresponds to an RAM of 8 MB and has a corresponding text box 1916. A categorical factor e of L1 corresponds to a connection speed of 0-1 Mbps and has a corresponding text box 1918. Default weights can be assigned to the other levels or for levels of unselected categorical factors (e.g., a default weight of 1). As an example, a test engineer based on prior knowledge of testing the complex system 1800 or another system not shown may believe that when the operating system is Linux® or when the RAM used is 8 MB, the complex system 1800 is more likely to fail and thus a weight greater than a predefined threshold (e.g., a default weight of 1) is entered into text box 1914 and text box 1918 using the keyboard 1904 and trackpad 1906. However, in this example this is the first time that a connection speed of 0-1 Mbps is studied, so the test engineer assigns the categorical factor of connection speed in text box 1918 a highest weight to place more attention on this component should failures occur involving this component.

In one or more embodiments, a component models an operation of the software program (e.g., modeling the operation of an operating system 1802). A computing device (e.g., computing device 1302) is used to test each of the test cases of the test suite by executing the software program on computer hardware using respective test conditions of the respective test case (e.g., executing a Windows® or Linux® operating system). In one or more embodiments, a failure indication indicates that executing the software program using the respective test conditions did not operate in accordance with a set of predefined behaviors for the software program. For instance, it may take beyond a predefined threshold for processing time for the operating system 1802 to manage a particular resource of the complex system 1800 or the operating system 1802 fails entirely in an operational task. In other examples, the output from a software program may not produce expected outcomes (e.g., a statistical program using RAM 1806 may produce an unexpected model or mathematical numbers).

In one or more embodiments, the complex system 1800 is a computer-simulated model that represents behavior of computer hardware (e.g., keyboard 1810) for testing a computer-simulated environment. In one or more embodiments, the computer-simulated model is a deterministic model in which the output of the model is fully determined by the parameter values and initial conditions. Other computer-simulated models include stochastic models in which a same set of parameter values and initial conditions will lead to an ensemble of different outputs. Alternatively or additionally, aspects of the system are physically tested. For instance, a categorical factor represents operation of a circuit of the keyboard 1810 in a physical test.

Regardless of the particular testing method performed, as shown in FIG. 19, a graphical user interface 1920 displays an indication 1922 of the most likely potential cause 1922 for a potential failure of the complex system 1800 that accounts for the input weights and any failure indications from testing the complex system 1800. Of course one of ordinary skill in the art will appreciate that weights could be input following testing to generate the ordered ranking. In this case, the most likely cause for a failure is using the RAM of 8 MB and a connection speed of 0-1 Mpbs. Thus, the test engineer will likely test combinations for the test system 1800 that involve this combination and/or recommend refraining from designing a system 1800 with that combination.

As shown in FIG. 19, the indication 1922 is part of an ordered ranking 1924 of combinations for further testing of the system. In one or more embodiments, the graphical user interface displays a single most likely potential cause a particular number of causes, or particular tiers of causes. As shown in FIG. 19, three tiers are shown in which combinations of a same probability are displayed in the same tier. In one or more embodiments, a user sets a preference for display of the most likely potential cause (e.g., the user sets a preference for the number of potential causes to display). Should testing indicate that the combination of RAM (8 MB) and connection speed (0-1 Mbps) does not cause a failure of complex system 1800, a test engineer can test the other combinations according to the ordered ranking.

Figure 20A:
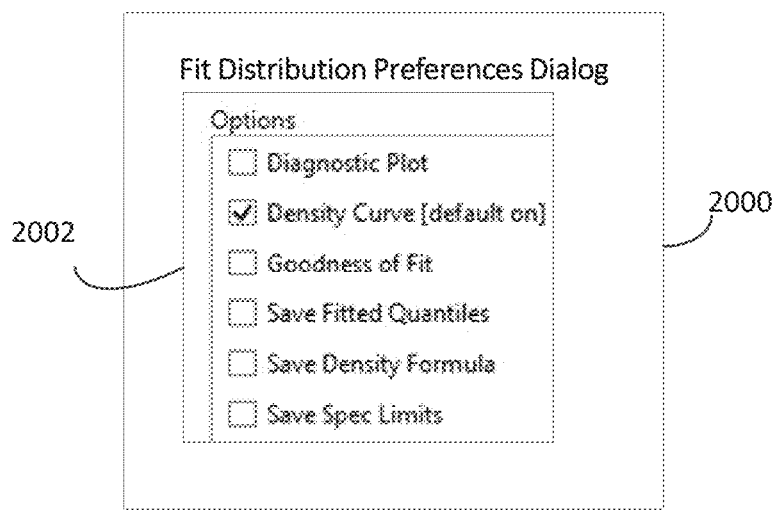
FIG. 20A illustrates an example complex system in at least one embodiment of the present technology.

FIG. 20A illustrates another example complex system 2000. In this example, the complex system 2000 involves components or categorical factors 2002 that are preferences for a fit distribution application of a software program. A user can check or uncheck particular preferences to include or not include these preferences for the fit distribution application. Thus, the options for a particular component are in use or not in use in the application represented by checked or unchecked respectively in a graphical user interface for the fit distribution application.

Figure 20B:
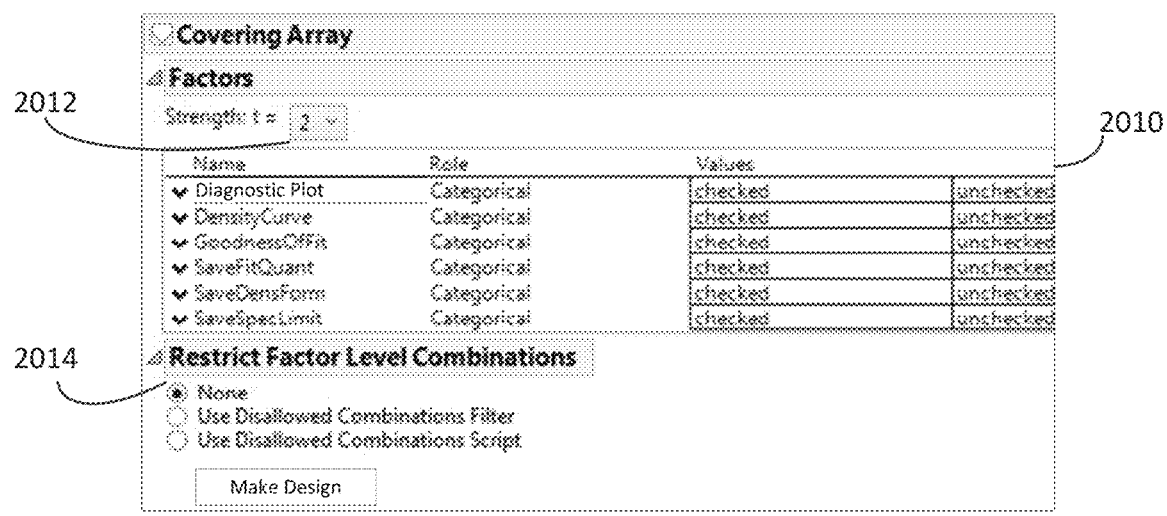
FIG. 20B illustrates an example graphical user interface for a covering array in at least one embodiment of the present technology.

FIG. 20B illustrates an example graphical user interface 2010 for generating a test suite. In one or more embodiments, a graphical user interface is displayed for setting criteria for generating the test suite. For example, in FIG. 20B a covering array is used to test the complex system 2000. The graphical user interface 2010 displays a drop-down box 2012 for setting the strength of the covering array (e.g., a strength of 2) for the categorical factors 2002. The graphical user interface 2010 also shows selections 2014 for restricting certain level combinations that are not allowed in the covering array (i.e., disallowed combinations). An example of a disallowed combination is a given categorical factor is always unchecked whenever another categorical factor is checked. Alternatively or additionally, a disallowed combination could be assigned a weight (e.g. a weight of 0) to indicate that a particular combination would never be a source of error because it is disallowed. One of ordinary skill in the art will appreciate other settings for generating the test suite, such as setting the test suite to be an orthogonal array or a number of test cases.

FIG. 20C illustrates a graphical user interface 2020 displaying the results of a test suite for testing complex system 2000 according to the user selections displayed in FIG. 20B. Only test case 3 failed as indicated on the graphical user interface 2020 by indicating "Fail" in the result column 2022. A success indication is displayed in the graphical user interface 2020 for the other test cases by indicating "Pass" for the respective test case.

Figure 20D:
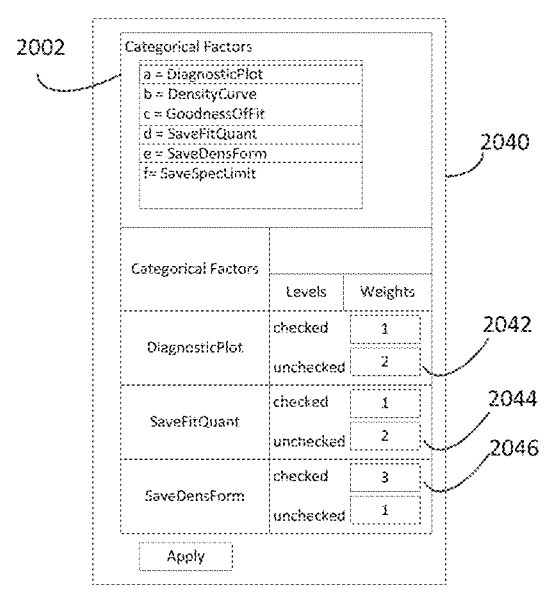

FIG. 20D illustrates an example graphical user interface 2040 for user entry of weights for selected categorical factors. As shown the user has selected particular ones of the categorical factors 2002 for assigning weights. The user has input particular weights in text boxes 2042, 2044, and 2046.

FIG. 20E illustrates an example graphical user interface 2050 that indicates the most likely potential cause for the potential failure of the system. As shown in FIG. 20E, the graphical user interface 2050 displays an ordered ranking 2052 of potential causes for a potential failure of the system arranged based on cause indicators expressed as probabilities 2054 assigned to particular combinations. As shown each of the categorical factors of a combination in the ordered ranking 2052 was involved in the test case that resulted in a failure indication as shown in FIG. 20C. In this embodiment, the computing system outputting to a displaying device the indication of the most likely potential cause also tests the test suite, so a summary 2056 of the test results as an example is also shown in graphical user interface 2050.

While example embodiments focused on causes due to combinations involving two inputs, the same methodology holds if all combinations due to two inputs have been ruled out. In addition, if one were to assign a prior weight to interactions of each strength, analysis could include interactions of different strengths that are potential causes. For example, if one believed that two-input combinations are four times more likely than three-input combinations to cause a failure, each $w_{i_1 i_2}(j_1, j_2)$ would be multiplied by four before making comparisons. This can be useful in uncovering cases in which a higher-order combination appears in multiple test cases, and no lower-order combinations appear or have been ruled out.

In one or more example embodiments that extend to three inputs, for distinct inputs $i_1 i_2$, and $i_3$ at levels $j_1, j_2$, and $j_3 (j_a \in 1, \ldots, s_a)$, respectively, the weight of the three-input combination, denoted by $w_{i_1 i_2 i_3}(j_1, j_2, j_3)$, can be calculated as $$w_{i_1 i_2 i_3}(j_1, j_2, j_3) = w_{i_1}(j_1) w_{i_2}(j_2) w_{i_3}(j_3) \tag{9}$$

assuming that Equation (1) was used for the weights of two-input combinations. As before, individual weights can be assigned to $w_{i_1 i_2 i_3}(j_1, j_2, j_3)$ (e.g., based on prior knowledge) instead of using Equation (9). If Equation (1) was not used for any pair of inputs in $\{i_1 i_2 i_3\}$, an adjustment should be made for $w_{i_1 i_2 i_3}(j_1, j_2, j_3)$. Two possibilities are:

$$1) \ w_{i_1 i_2 i_3}(j_1, j_2, j_3) = \max\{w_{i_1 i_2}(j_1, j_2) w_{i_3}(j_3), w_{i_1 i_3}(j_1, j_3) w_{i_2}(j_2), w_{i_2 i_3}(j_2, j_3) w_{i_1}(j_1)\}, \tag{10}$$

where max refers to the maximum value among the set of values, or $$2) \ w_{i_1 i_2 i_3}(j_1, j_2, j_3) = \text{ave}\{w_{i_1 i_2}(j_1, j_2) w_{i_3}(j_3), w_{i_1 i_3}(j_1, j_3) w_{i_2}(j_2), w_{i_2 i_3}(j_2, j_3) w_{i_1}(j_1)\}, \tag{11}$$

where ave refers to the average of the values.

Equation (10) places greater emphasis on the prior knowledge that has been specified using Equation (1).

Weights for combinations involving more than three inputs can be defined in a similar fashion. In general for f>2 inputs, the weight of a combination is the product of the weights of the individual inputs:

$$w_{i_1 i_2, \ldots, i_j}(j_1, j_2, \ldots, j_j) = w_{i_1}(j_1), w_{i_2}(j_2), \ldots, w_{i_j}(j_j).$$

Equations (10) and (11) can be expressed similarly, with adjustments to the number of ways to group inputs as m increases.

Embodiments herein allows the failures resulting from executing a test suite to be analyzed so that the potential causes of the failures can be ranked. One of ordinary skill in the art will appreciate that embodiments herein are useful for other applications and purposes that those expressly described herein. For example, the use of weights as a criterion for test suites can also be particularly useful when a test engineer has a testing budget that allows more test cases than a covering array of optimal size. Weights can help determine which additional test cases to add to the test suite. These additional test cases can have the beneficial effect of reducing the number of potential causes and can therefore provide a happy medium between optimal size covering arrays and error-locating arrays. Alternatively, one or more embodiments of computing weights could be used by algorithms that construct biased covering arrays or to encode prior information for a test suite prioritization technique. In addition, use of weights could instead represent costs for algorithms that construct cost-aware covering arrays.

Further, in one or more embodiments, the results of testing in accordance with the ranking can be used to augment the weights for future test cases. For example, a test engineer can learn that a combination of test conditions probably should not be weighted as problematic or should be weighted to downgrade the likelihood of it being a potential cause of failure in future test suites if testing indicates it is not a source of failure in a current test suite. In one or more embodiments, a test suite is generated in a repeating pattern (e.g., every day) and the test cases in the test suite or the weights applied can be augmented based on the performance of testing in a previous period of the repeating pattern.

Further, in one or more embodiments, the results of testing in accordance with the ranking can be used to augment the weights for future test cases. For example, a test engineer can learn that a combination of test conditions probably should not be weighted as problematic or should be weighted to downgrade the likelihood of it being a potential cause of failure in future test suites if testing indicates it is not a source of failure in a current test suite. In one or more embodiments, a test suite is generated in a repeating schedule (e.g., every day) and the test cases in the test suite or the weights applied can be augmented based on the performance of testing in a previous period of the repeating pattern.

In one or more embodiments, a graphical user interface is provided to allow users to visualize a test suite in a graphical representation and interact with key aspects of the design of the test suite (e.g., in an interactive report or viewer of the graphical user interface). This is particularly useful when there are more than three factors to test cases of a test suite. For instance, the user of the graphical user interface can interact with the graphical user interface to change levels associated with factors of the test suite and explore projections into fewer factors needed for a test suite. This allows test planners to explore and select different design options for a best design based on a visual assessment rather than solely on a table of entries or summary of statistics of test results resulting in a more complete understanding of their design. In particular, by providing a visual representation of a design, a user of the graphical user interface can identify missing pieces or gaps in a design of an experiment and rearrange levels and factors in the design to see the impact of the changes on the design in real time (e.g., in improving design efficiency or design coverage).

Figure 21:
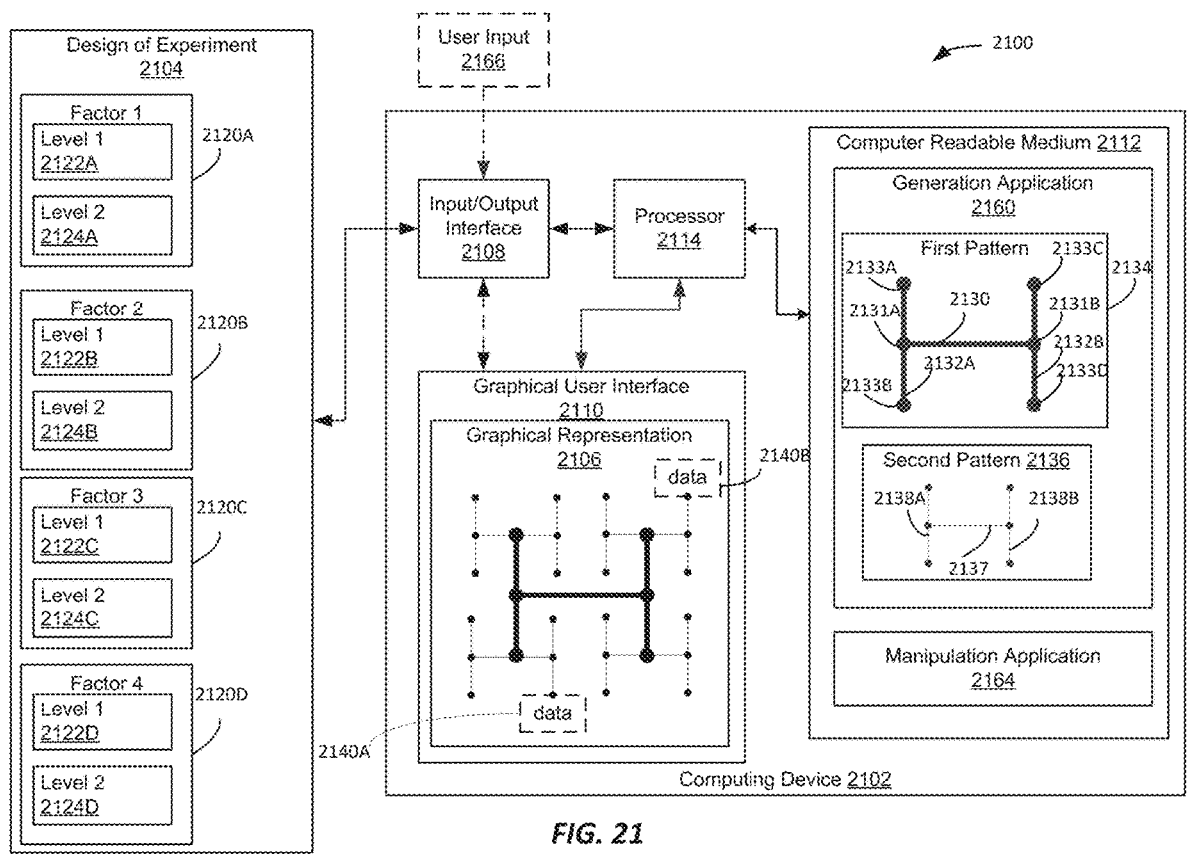
FIG. 21 illustrates an example block diagram of a system for displaying a graphical user interface with a graphical representation in at least one embodiment of the present technology.

FIG. 21 illustrates an example block diagram of a system 2100 for displaying a graphical user interface with a graphical representation. The graphical user interface can be used for applications related to test suites for detecting a potential failure of a complex system described herein and for other applications related to design or design of an experiment (e.g., covering array diagnostics for a design, analysis of response after a designed experiment, etc.).

The system 2100 includes a computing device 2102. In one or more embodiments, the computing device 2102 is the same or different from computing devices described herein (e.g., computing device 1302). In one or more embodiments, the system 1300 includes other devices (e.g., input device 1304 described herein) for receiving information related to the design of an experiment 2104 (e.g., a test suite with test cases as described herein). The system is configured to exchange information between devices in the system (e.g., via wired and/or wireless transmission) and devices in other systems described herein (e.g., system 1300). For example, a network (not shown) can connect one or more devices of system 2100 to one or more other devices of system 2100 or system 1300. In one or more embodiments, fewer, different, and additional components than shown can be incorporated into the system 2100 (e.g., components of system 1300).

The computing device 2102 has a computer-readable medium 2112 (e.g., computer-readable medium 1312) and a processor 2114 (e.g., processor 1314). For instance, computer-readable medium 2112 comprises one or more features of computer-readable medium 1312 or is computer-readable medium 1312. Additionally, or alternatively, processor 2114 comprises one or more features of processor 1314 or is processor 1314. For instance, in one or more embodiments computer-readable medium 2112 stores instructions for execution by processor 2114. For example, computer-readable medium 2112 comprises instructions for a generation application 2160 and a manipulation application 2164.

In one or more embodiments, the generation application 2160 determines or generates a graphical representation 2106 representing the design of an experiment (e.g., test cases of experiment or results of an experiment designed according to the design of an experiment). This is particularly useful for generating a graphical representation 2106 for a design of an experiment that comprises a plurality of test cases, where each element of a test case is a test condition for testing one of factors for an experiment A test condition comprises one of different levels representing different options for a given factor in the design (e.g., different options for components of a tested complex system described herein). For instance, as shown in FIG. 21, the computing device 2102 in one or more embodiments receives via input/output interface 2108 design of experiment information 2104 related to a plurality of factors 2120 (e.g., four factors 2120A-D) that each comprise at least two levels, a first level 2122 and a second level 2124 representing different options for a given factor in the design of an experiment. One of ordinary skill in the art will appreciate that the computing device can receive design of experiment information 2104 pertaining to more or less factors and that each factor could have more or less levels associated with the factor. In one or more embodiments, the generation application 2160 generates the graphical representation 2106 based on or otherwise responsive to receiving the design of experiment information 2104 (e.g., a number of patterns in a graphical representation is based on received design of experiment information 2104).

In one or more embodiments, the generation application 2160 plots data 2140 on the graphical representation 2106 corresponding to data assigned to one or more test cases of the plurality of test cases on the graphical representation. For instance, data 2140 could include the factors of the test cases, a test case number, a result of a test case, etc. such that the graphical representation provides a visual representation of information to a user of the graphical user interface 2110. In one or more embodiments, the informational value of data is derived or otherwise based on the proximity of data 2140 to one or more patterns of the graphical representation.

In one or more embodiments, the generation application 2160 generates a graphical representation 2106 that comprises a fractal-like representation. For instance, the graphical representation 2106 comprises a first pattern (e.g., first pattern 2134) and a second pattern (e.g., second pattern 2136) of a fractal sequence. For instance, a type of fractal sequence is a fractal in which a curve or geometric figure has a similar pattern recurring at progressively smaller scales. As shown in FIG. 21, the second pattern 2136 is geometrically similar to and proportionality smaller than the first pattern. Geometrically similar as used herein is given its meaning in the field of geometry (e.g., having structures of a same shape). For instance, structures (or geometric curves or figures) in the field of geometry having a same shape would include shapes with corresponding sides proportional and corresponding angles equal.

In the example shown in FIG. 21, the first pattern 2134 has three line segments: a main axis 2130 and secondary axes 2132A and 2132B. The second pattern 2136 has corresponding line segments (2137, 2138A and 2138B) of a shorter length. The angles at the attachment points 2131 of the line segments of the first pattern 2134 form approximately right angles (i.e. 90 degree angles). The second pattern 2136 has approximately similar angles at attachment points of its respective line segments. Fractal sequences with this particular shape or structure of patterns are referred to herein for simplicity as a tree fractal sequence with individual axes other than the main axis referred to as branches of the tree. The main axis and a display of this fractal sequence in a display or other viewer of a graphical user interface is referred to herein as a tree view.

In one or more embodiments, the generation application 2160 generates other shapes or selects a shape of a plurality of shape options for a fractal sequence as described in more detail with respect to other embodiments (e.g., a grid view).

In one or more embodiments, the graphical representation 2106 comprises a plurality of axes used in a fractal sequence for respective ones of factors received, indicated, or otherwise represented in the design of experiment information 2104. For instance, an axis (e.g., axis 2132A) of the plurality of axes has two points comprising a first point (i.e. endpoint 2133A) that corresponds to a first level (e.g., level 2112A) of a respective factor (e.g., factor 2120A) and a second point (endpoint 2133B) that corresponds to a second level (e.g., level 2124A) of the respective factor. In one or more embodiments, data 2140 labeling a factor assigned or otherwise corresponding to one or more axes is plotted in proximity to an axis assigned or otherwise corresponding to a particular factor received in the design of experiment information 2104. For instance, each free endpoint terminating one of the axis of the graphical representation 2106 corresponds to a potential test case. Data 2140A corresponds to one test case and data 2140B corresponds to another test case in an example where there are multiple different test cases. The location of the plotted data 2140A and 2140B relative to a free end point of the graphical representation is selected based on the factors and levels assigned to the test case represented by the axes of the graphical representation 2106. Endpoints that do not have plotted data, for instance, correspond to a potential test case that was not selected for an experiment design.

In one or more embodiments, the graphical representation 2106 comprises a tree fractal sequence comprising a first pattern 2134 and a second pattern 2136. The first pattern 2134 is generated by selecting a main axis (e.g., main axis 2130) of the plurality of axis and joining a secondary axis (e.g., secondary axis 2132) of the plurality of axes to the main axis forming the first pattern. In this case, the first pattern 2134 combines two secondary axes 2132A and 2132B to the main axis. The first pattern 2134 comprises at least four endpoints (2133A-2133D) that are endpoints of one or more axes of the first pattern 2134.

In one or more embodiments, the graphical representation 2106 comprises a set of second patterns 2136. Each pattern of the set of the second patterns 2136 is a structure geometrically similar to the first pattern 2134 and proportionally smaller than the first pattern 2134. The structure is formed from axes of the plurality of axes representing factors 2120 of the experiment. Each pattern of the set of the second patterns is joined to the first pattern at each of at least four endpoints 2133A-D of the first pattern. In one or more embodiments, data 2140 is plotted at locations according to a fractal sequence of the graphical representation 2106 as a function of factors and levels represented by the fractal sequence. For instance, as shown in FIG. 21, data 2140 is plotted at endpoints of second patterns 2136 of the fractal sequence.

In one or more embodiments, the manipulation application 2164 manipulates the graphical representation 2106 according to one or more manipulations. For instance, a manipulation may be generated by the computing device 2102. As explained, the computing device 2102 could change the designated main axis (e.g., in response to a changed prioritization based on results of an experiment using the factors). Additionally or alternatively, a manipulation is in response to user input 2166 by a user of the graphical user interface 2110. For instance, the user input 2166 could include a manipulation of the display of the graphical representation 2106 (e.g., by selection of one of different structure options for the fractal sequence). Alternatively, or additionally, the user input 2166 could include a manipulation of data represented by the graphical 2106 (e.g., a manipulation of a value corresponding to a level for a factor). The user input 2166 could be received via one or more input devices as described herein (e.g., input device 1304).

In one or more embodiments, the computing device displays or otherwise outputs to a graphical user interface 2110 a graphical representation 2106 of the design of an experiment (e.g., test cases of experiment or results of an experiment designed according to the design of an experiment). Alternatively, as shown in FIG. 13, a graphical user interface can be displayed on an output device (e.g., output device 1306) external to a computing device (e.g., computing device 2102) and information is exchanged between an output device via one or more interfaces with the computing device 2102 (e.g., via input/output interface 2108). One of ordinary skill in the art will appreciate that the computing device 2102 could display the graphical representation 2106 in other ways different from a graphical user interface 2110

(e.g., outputting a graphical representation 2106 to other output devices described herein (e.g., a display, printer or storage).

In one or more embodiments, the graphical user interface 2110 can also be referred to as an interactive graphical user interface that allows manipulation of the graphical representation 2106 (e.g., manipulation in response to changed input regarding the experiment or user input 2166 to the computing device 2102). In one or more embodiments, manipulation of an interactive graphical user interface provides advantages to a user of the interactive graphical user interface for improving the visualization of test cases or changing test conditions of test cases as will be described in more details herein.

Figure 22:
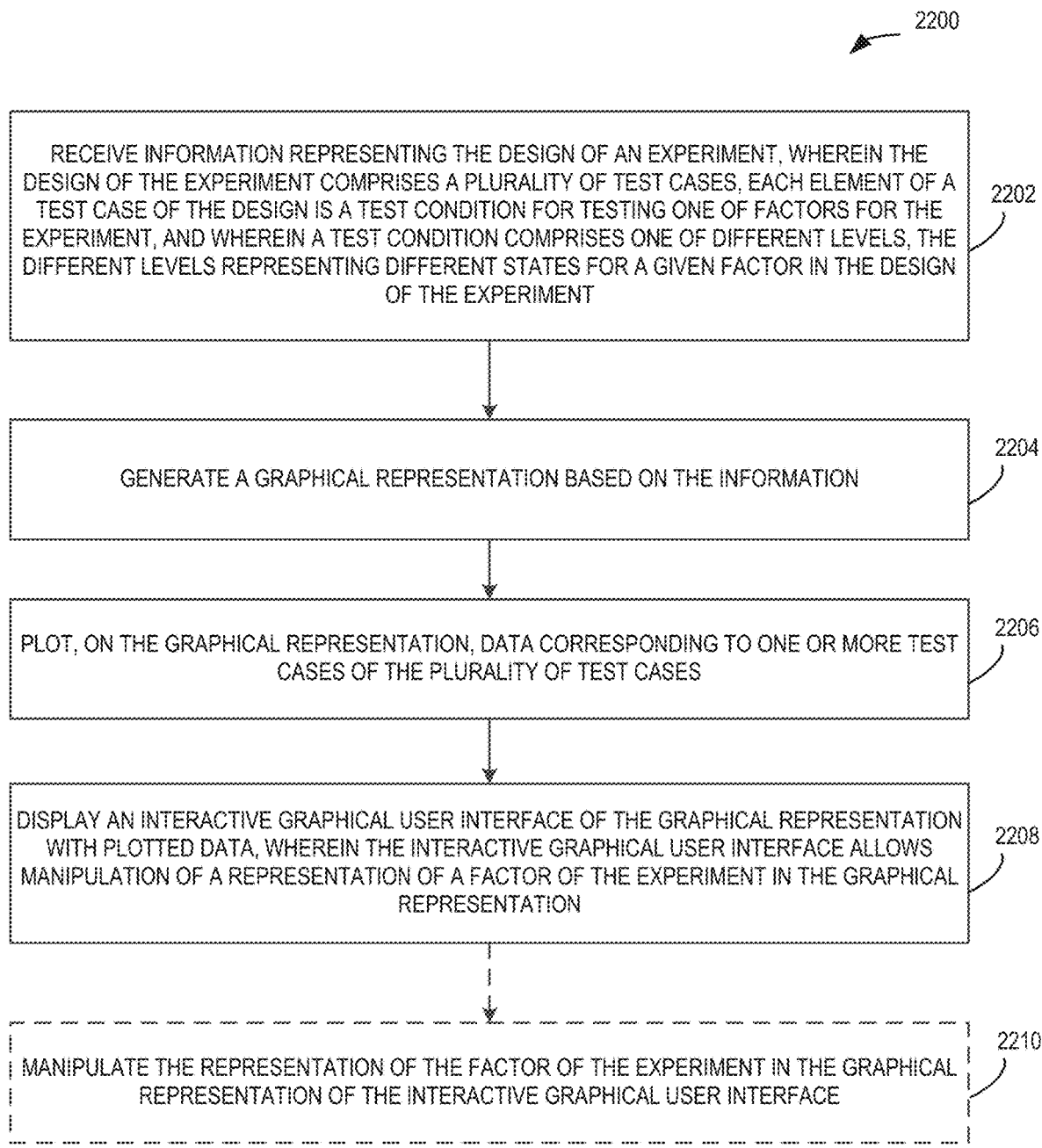
FIG. 22 illustrates an example flow diagram for displaying a graphical user interface with a graphical representation in at least one embodiment of the present technology.

FIG. 22 illustrates an example flow diagram for a computer-implemented method 2200 for displaying an interactive graphical user interface described herein. For instance, in one or more embodiments, the system 2100 implements the method 2200.

The method 2200 includes an operation 2202, that includes receiving information representing a design of an experiment (e.g., design of experiment information 2104). The design of the experiment comprises a plurality of test cases. Each element of a test case of the design is a test condition for testing one of factors for the experiment A test condition comprises one of different levels, the different levels representing different options for a given factor in the design of the experiment. For instance, in one or more embodiments, the information represents or indicates unique numbers assigned to each test case within the design of the experiment, the number of factors in the design and their corresponding levels, etc. Alternatively or additionally, in one or more embodiments the information represents or indicates results of an experiment according to the design of the experiment. For instance, the results could include values corresponding to a result of each of the test cases for the experiment according to the design.

The method 2200 includes an operation 2204 that includes generating a graphical representation (e.g., graphical representation 2106) based on the received information. For instance, in one or more embodiments, the graphical representation represents levels of factors of the design.

The method 2200 includes an operation 2206, that includes plotting, on the graphical representation, data (e.g., data 2140) corresponding to one or more test cases of the plurality of test cases of the design of the experiment. For instance, the data comprises factor information (e.g., received in the design of experiment information 2104). Additionally or alternatively, the data comprises a value representing a test case or results of an experiment conducted according to the design.

The method 2200 includes an operation 2208, that includes displaying an interactive graphical user interface (e.g., graphical user interface 2110) comprising the graphical representation. The interactive graphical user interface allows manipulation of a representation of a factor of the experiment in the graphical representation.

Optionally, the method 2200 includes an operation 2210, that includes manipulating the representation of a factor of the experiment in the graphical representation of the interactive graphical user interface. For instance, in one or more embodiments, the graphical representation is manipulated by changing a prioritization of the plurality of axes in the fractal sequence (e.g., for a user of the graphical user interface to observe plotted data more relevant to an experiment outcome).

Figure 23:
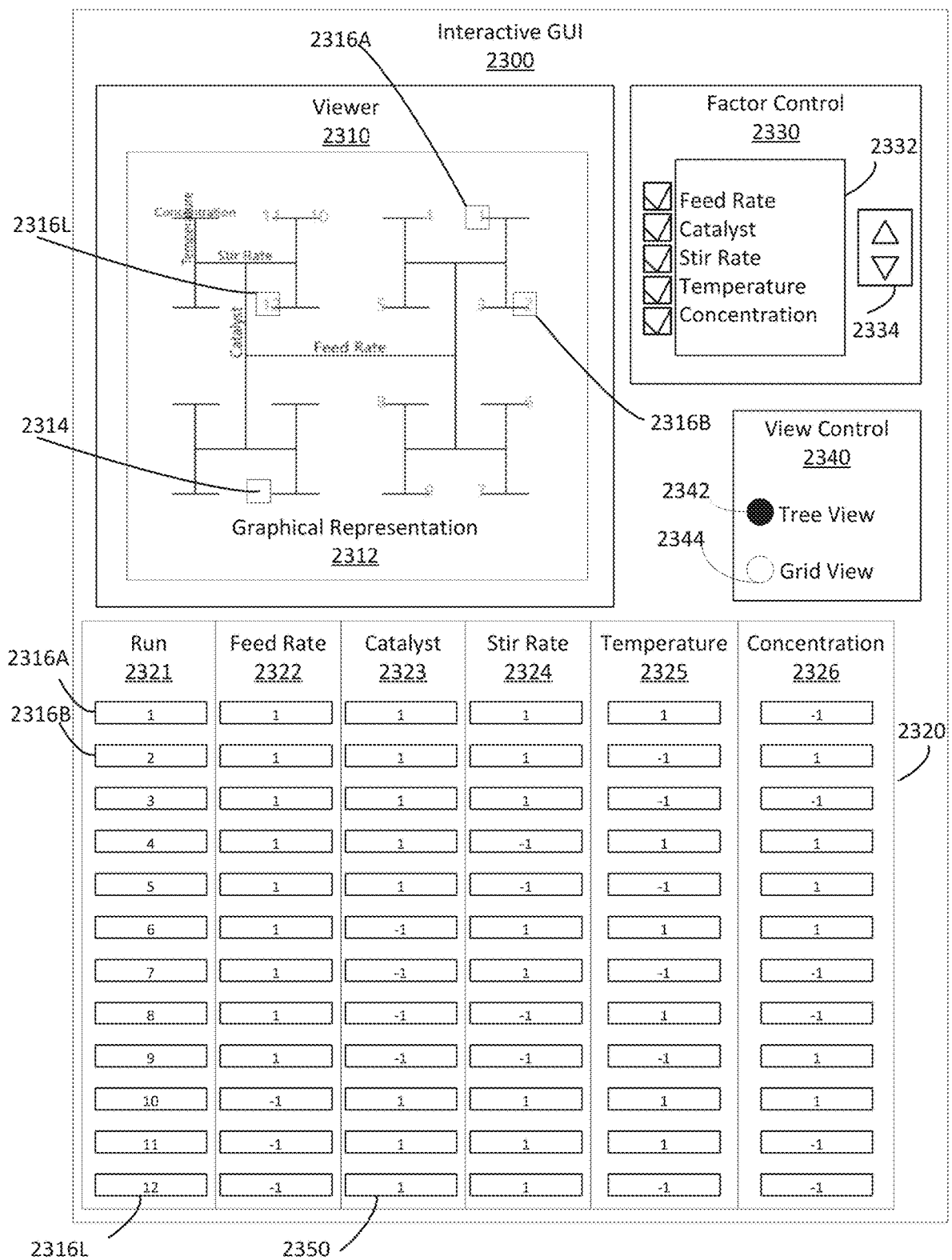
FIG. 23 illustrates an example interactive graphical user interface for controlling a graphical representation in at least one embodiment of the present technology.

FIG. 23 illustrates an example interactive graphical user interface 2300. The interactive graphical user interface 2300 has a viewer 2310 for viewing a displayed graphical representation 2312. An example of a viewer 2310 is a DESIGN FRACTAL GRAPH by SAS Institute Inc. of Cary, N.C. The viewer 2310 displays a graphical representation 2312 that represents five factors for an experiment. The viewer 2310 could be used for one or more different experiments with different numbers of factors and levels. The graphical representation 2312 is generated or otherwise determined using a tree fractal sequence as described herein. Other fractal sequences (e.g., a grid fractal sequence) could be used.

The example interactive graphical user interface 2300 displays a report involving mixing a catalyst into a chemical. In other words, the experiment tests a complex system of a chemical solution involving a catalyst and a chemical where different mechanisms of combining the catalyst and chemical solution provide different results for the resulting chemical solution. A first factor feed rate 2322 is related to how fast the catalyst is fed into the chemical. A second factor catalyst 2323 is related to the type of catalyst used. A third factor stir rate 2324 is related to how fast or how long the catalyst is stirred in the chemical once added. A fourth factor temperature 2325 is related to the temperature of the chemical when the catalyst is added or a reaction temperature. A fifth factor concentration 2326 is related to amount of catalyst per chemical solution. The scenario of the chemical solution is merely an example. The interactive graphical user interface 2300 could be used for the design of any experiment (e.g., for testing a complex system described herein).

The first pattern of the graphical representation 2312 has axes corresponding to feed rate 2322 (horizontal axis) and catalyst 2322 (vertical axes). The set of second patterns have axes corresponding to stir rate 2324 (horizontal axes) and temperature 2325 (vertical axes). The number of factors is an odd number, so the fractal sequence is terminated by axes corresponding to concentration 2326 (horizontal axes).

FIG. 23 illustrates a number of controls for a user of the graphical interface to manipulate the graphical representation 2312. A data control 2320 allows manipulation of plotted data (e.g., data 2136) displayed in the graphical representation 2312. An example of a data control 2320 is design exploration by SAS Institute Inc. of Cary, N.C. Data control 2320 in this case displays a matrix of each of the test cases of the experiment. A run column 2321 denotes the order of the test cases (e.g., indicated by received design of experiment information). Data in run column 2321 can then be plotted in a graphical representation (e.g., data 2136 plotted graphical representation 2312).

Each of the other columns in the data control 2320 denote a level assigned to the factor for each of the test cases. The levels are represented by a "1" and a "−1". These are merely symbolic representations of two options for a factor. For example, in the context of temperature 2325 factor, a "−1" could represent or otherwise indicate a temperature of 90 degrees and a "1" could represent or otherwise indicate a temperature of 100 degrees. The actual value assigned to a level could instead be displayed in the data control 2320 or other symbols could be used to represent different options (e.g., a "+" and a "−"). A value (e.g., either −1 or 1) is assigned to each test condition of a given test case of the test cases displayed in data control 2320.

In one or more embodiments, a computing device (e.g., computing device 2102) displays interactive graphical user interface (graphical user interface) by displaying the graphical representation 2312 in proximity to a data control 2320 displaying data values assigned to each test condition of the design of the experiment. The graphical representation displays plotted values corresponding to the values assigned to each test case of the design of the experiment in the run column 2321 (i.e., runs 1-12). In the tree view shown, up is positive for the vertical branches and right is positive for the horizontal branches. Following run 1 from the main axis corresponding to feed rate, the number "1" is displayed in proximity to almost the furthest endpoint up and to the right. However, the last factor concentration 2326 is given a "−1" so the "1" is plotted just to the left side of the branch. Other orientations for a tree view could be used. For example, the main axis could be vertical rather than horizontal. Alternatively or additionally, up could be negative and/or right could be negative.

In one or more embodiments, displaying the runs graphically in the viewer 2310 enables a designer of an experiment to consider their coverage of various factors. For example, as shown in the graphical representation 2312, there are no runs plotted in the pattern in the left bottom corner. This may encourage a designer to consider having test cases that would depict a run in that pattern in the left bottom corner.

In one or more embodiments, the graphical representation and matrix of the data control 2320 are interdependent such that changing a value displayed in the matrix changes a display of a plotted value in the graphical representation in the interactive graphical user interface, or changing the display of a plotted value in the graphical representation in the interactive graphical user interface changes a value displayed in the matrix. For instance, the numbers displayed in the matrix could be "buttons" that toggle the value assigned when clicked by a user of the graphical user interface 2300 (e.g., with a mouse 1340). Clicking on a button would then change the location of the plotted run to the opposite side of the graph along the axis determined by the column where that button was located. For instance, toggling data 2350, which currently has a value of "1", assigned to catalyst 2323 in run 12 to "−1" would move the data 2316L representing plotted run "12" to the opposite side of the catalyst axis to a region 2314. As another example, toggling the "1" for feed rate 2322 of run 7 would move the plotted "7" to the region 2314. If both changes were made, a value of "7" and "12" would both be displayed in the region 2314. Alternatively or additionally, a value displayed can be pulled to a different region of a graphical representation (e.g., using a mouse 1340), and the corresponding value displayed in the data control 2320 will change.

One of ordinary skill in the art will appreciate other ways to augment the values displayed in the data control 2320. For example, the "buttons" could instead be text boxes for typing a different level value. This would be more useful in situations where there are more than two possible levels for a given factor (e.g., in other examples described herein with multiple possible levels for a given factor). Further, the run values could be text boxes for assigning a run. Alternatively, the numbers in the run 2321 column are static and the user could move test cases corresponding to a displayed run to a different row assigned to a different run to change the value assigned to that test case (e.g., using a mouse or arrow buttons).

In one or more embodiments, the interactive graphical user interface 2300 displays a factor control 2330 with each of the factors for the experiment. In one or more embodiments, a computing device (e.g., computing device 2102) manipulates the graphical representation by reducing or increasing the factors displayed in the graphical representation. For example, the computing device could receive user input (e.g., by checking a box associated with factors displayed in the factor control 2330).

In this case all the factors are checked so all the factors are displayed in the graphical representation 2312. In other examples, one or more boxes are unchecked which allows the user to project across the corresponding factors to a design in fewer factors. This would be of special interest in a screening design or application in which key factors are identified that impacted or affected the outcome or response in an experiment. In a screening application, it is expected that not all factors are significant, and so the graphical user interface 2300 allows a user to assess a design of an experiment and the significance of a factor or certain subsets of the factors in the experiment.

Other methods could be used to indicate the display of a factor. For instance, a drop down box could be displayed in proximity to a factor with options to set a color for axes associated with a given factor or to exclude the factor from display.

In one or more embodiments, a computing device (e.g., computing device 2102) manipulates the graphical representation based on a changed prioritization of factors in the graphical representation. This could be accomplished by the user manipulating the factor control 2330, e.g., by selecting one or more factors in a plot hierarchy 2332 and using up and down arrows 2324 to move the factors in the plot hierarchy 2332. For instance, as shown feed rate 2322 is at the top of the list in the factor control, so it is depicted in the graphical representation 2312 as the main axis. In this case, the main axis is displayed as a central horizontal axis. Other techniques could be used to further emphasize a main axis (e.g., a pattern or color assigned to the main axis). Catalyst 2323 is next highest in the plot hierarchy 2332, so it is depicted in the graphical representation 2312 as a secondary axis of the first pattern of the fractal sequence. This can be useful for assessing how the experimental runs are distributed in different configurations of the current design without projecting across less factors or otherwise changing the current design.

In one or more embodiments, the computing device changes a prioritization of factors in the graphical representation by replacing the main axis with a different axis of the plurality of axes. For instance, if catalyst 2323 and feed rate 2322 where switched by the user in the plot hierarchy 2332, the main axis would represent catalyst 2323 and the secondary axes of the first pattern would represent feed rate 2322.

Alternatively or additionally, the computing device changes the prioritization or sets a default prioritization based on the values in the data control 2320. For instance, the computing device could arrange or rearrange the graphical representation to better display coverage holes or gaps. A coverage hole or gap would include a region of the graphical representation correlating with a possible test case that is without plotted data, which would indicate a lack of coverage of this test case in the design of an experiment.

In one or more embodiments, the interactive graphical user interface 2300 displays options for changing the design of a pattern of the fractal sequence. For example, view control 2340 displays two options for a view of the graphical representation. A tree view 2342 is currently selected, but in other embodiments a grid view 2344 is selected.

Figure 24:
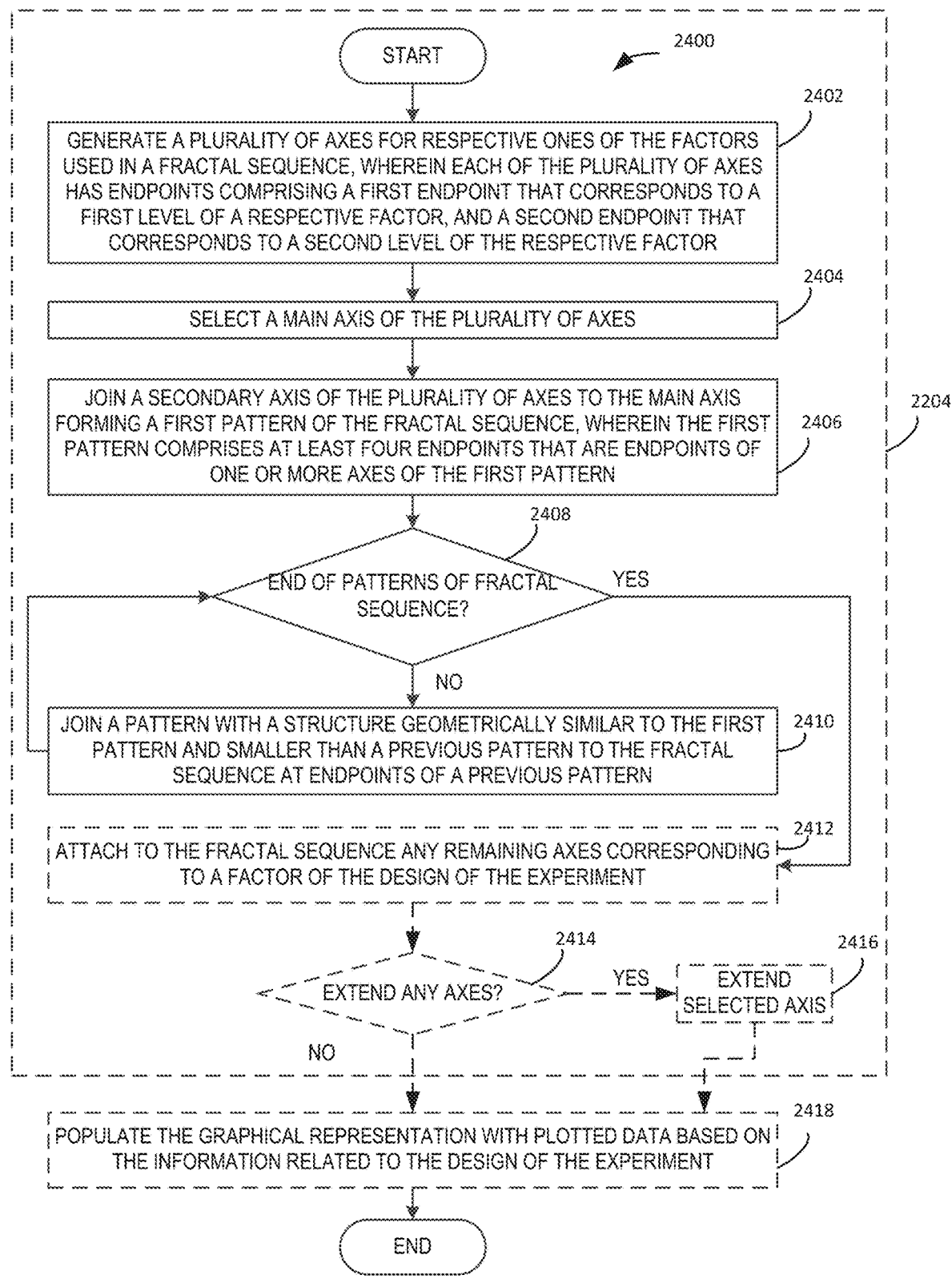
FIG. 24 illustrates an example flow diagram for generating a graphical representation in at least one embodiment of the present technology.
Figure 25A:
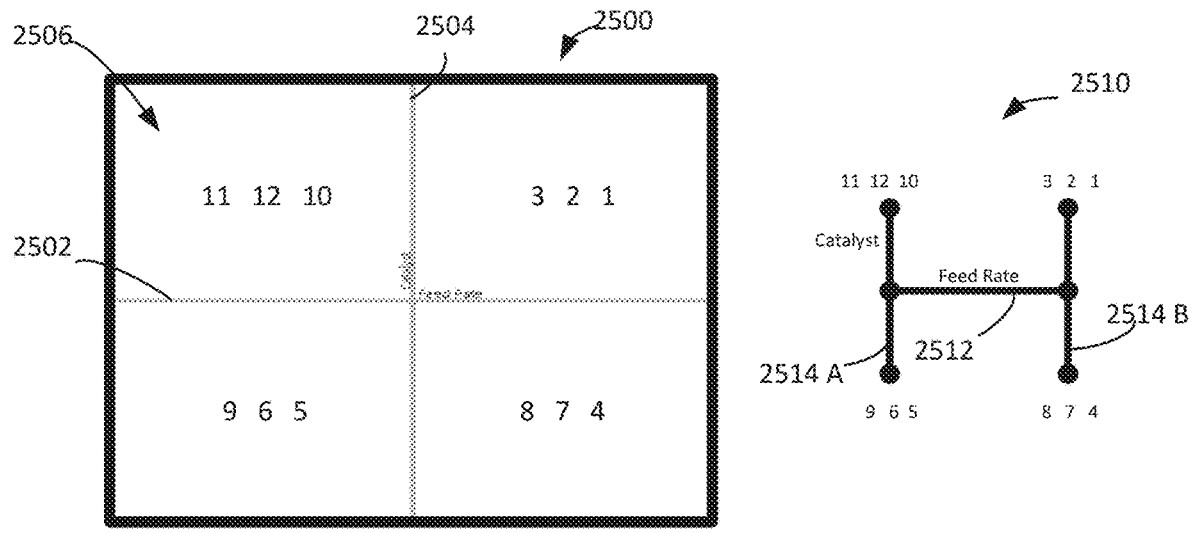
FIGS. 25A-25C illustrate example graphical representations involving multiple factors with each factor having two levels in at least one embodiment of the present technology.
Figure 25B:
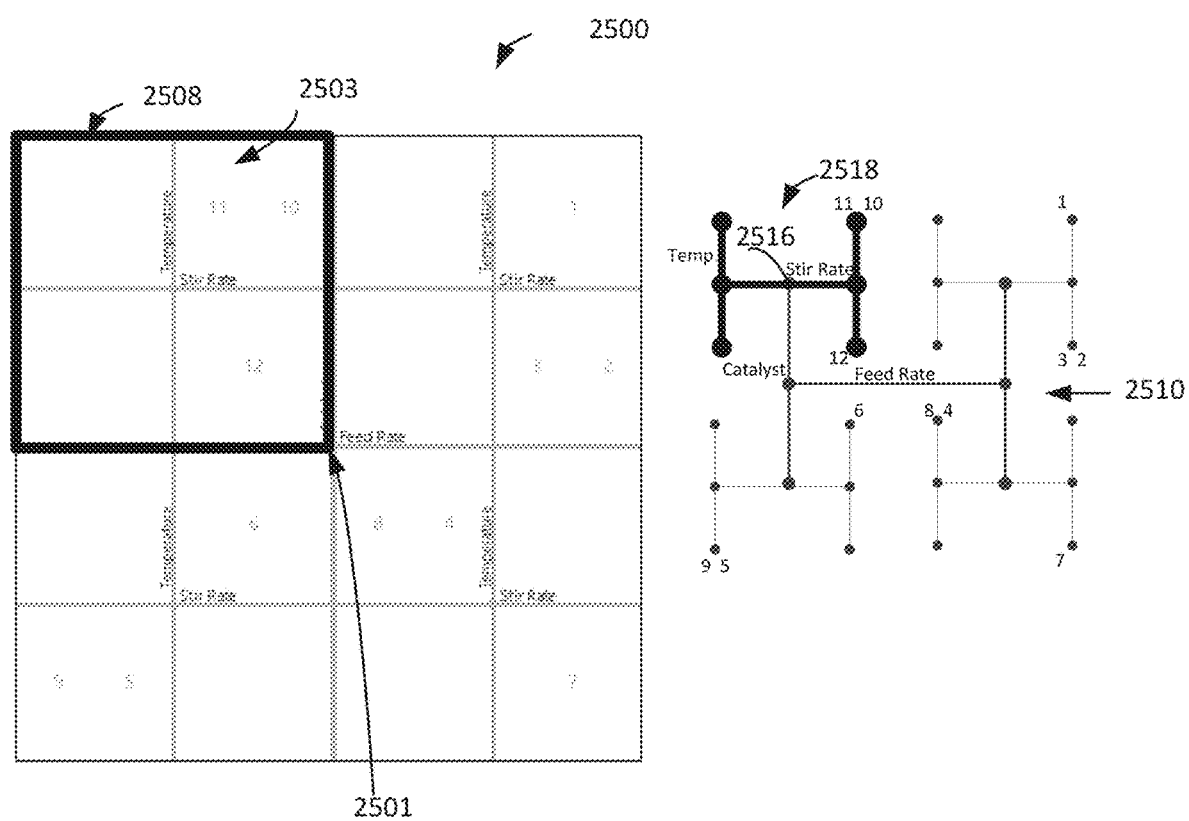
Figure 25C:
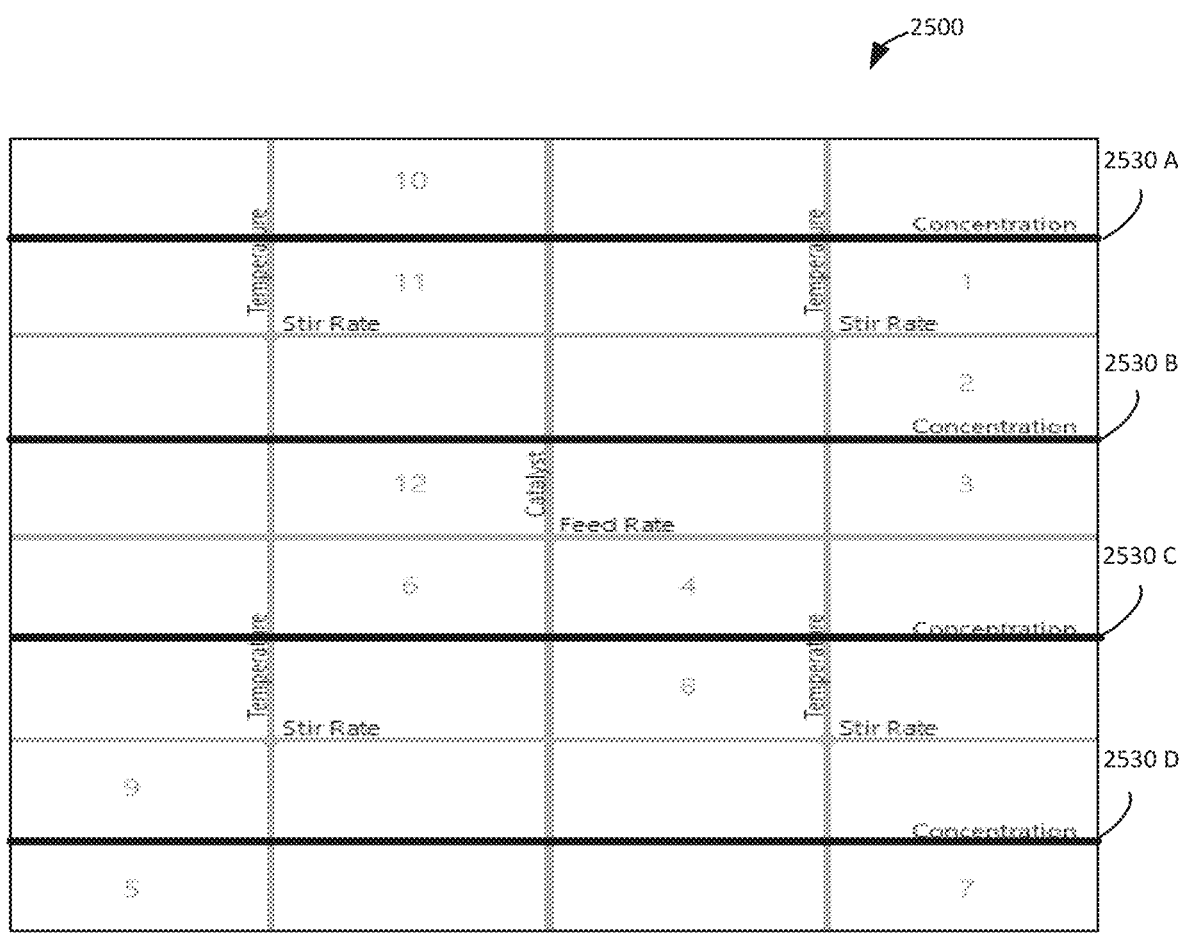

FIG. 24 illustrates an example flow diagram for a method 2400 for generating a graphical representation in at least one embodiment. In one or more embodiments, method 2400 is part of an operation 2204 of method 2200. FIGS. 25A-25C illustrate an example graphical representations (e.g., generated using the method 2400). These are merely examples; other graphical representations could be used.

The method 2400 comprises an operation 2402 that includes generating a plurality of axes for respective ones of the factors used in a fractal sequence. Each of the plurality of axes has endpoints comprising a first endpoint that corresponds to a first level of a respective factor, and a second endpoint that corresponds to a second level of the respective factor. In one or more embodiments, the operation 2402 comprises determining how many factors are to be represented by the graphical representation (e.g., based on user input selecting the factors). Method 2400 is used to show a method for generating a graphical representation of a plurality of factors. One of ordinary skill in the art will appreciate that the graphical representation could be used to represent only a single factor (e.g., in which only a single axis would be generated).

Operation 2402 can be completed prior to, contemporaneous with, or after other operations in the method 2400. For instance, the method 2400 comprises an operation 2404 that includes selecting a main axis of the plurality of axes. Operation 2402 could comprise generating a single axe=is of the plurality of axes for the main axis prior to, after or contemporaneous with selecting a main axis. Other axes of the plurality of axes could be generated prior to, after, or contemporaneous with other method steps. For instance, the method 2400 comprises an operation 2406 that includes joining a secondary axis of the plurality of axes to the main axis forming the first pattern. This operation could be done prior to or contemporaneous with generating an axis corresponding to the secondary axis.

FIG. 25A shows graphical representations each comprising a first pattern of a fractal sequence (i.e. grid pattern 2500 and tree pattern 2510) as described herein.

In one or more embodiments, a graphical representation (e.g., a tree fractal sequence or tree view) comprises a plurality of axes (e.g., axes 2512 and 2514). The structure of a first pattern (e.g., tree pattern 2510) comprises a first axis 2512 of the plurality of axes with a secondary axis 2514 of the plurality of axes. The secondary axis 1514 of the plurality of axes is perpendicular to the first axis 2512 of the plurality of axes and at an endpoint of the first axis 2512 of the plurality of axes. In the tree pattern 2510, there is a secondary axis 2514 at each endpoint of first axis 2512 (i.e. secondary axis 2514A and secondary axis 2514B). Each of the second axes can be considered a branch branching out from each endpoint of the main axes 2512, where each endpoint represents different levels of a factor represented by the main axis. A given branch off the main axis branches in opposite directions from the main axes (trunk) 2512 at an exposed endpoint to represent different levels of a given factor represented by the branch.

In one or more embodiments, the tree pattern 2510 is formed by generating two secondary axis (i.e. the branches) 2514. Each of the two secondary axes is perpendicular to the main axis (i.e. trunk) 2512 and comprises a respective middle point between the two endpoints of the respective one of the secondary axes 2514. The respective middle point is attached to each end point of the main axis 2512.

In other embodiments, a different graphical representation is used (e.g., a grid fractal sequence or grid view) comprises a plurality of axes. For instance, grid pattern 2500 also comprises a plurality of axes (e.g., axes 2502 and 2504). In this case the structure of grid pattern 2500 comprises perpendicular axes (i.e., axes 2502 and 2504) and a window 2506 defined by endpoints of the perpendicular axes 2502 and 2504. In this case there is a visual rectangle shown surrounding the perpendicular axes. However, in other embodiments a visual border of the window 2506 is not represented in the grid pattern 2500. Rather, it is merely the endpoints that define a rectangular edge of the window. In one or more embodiments, the window 2506 is a portion or all of a window of a viewer of a graphical user interface (e.g., viewer 2310 of graphical user interface 2300). Generating the window 2506 comprises defining a portion or all of a window of the viewer (e.g., by generating the perpendicular axes 2502 and 2504).

In one or more embodiments, the graphical representation only comprises a single axis or a single pattern. However, in other embodiments, the graphical representation is used to represent more than one or two factors.

Method 2400 comprises a step of determining whether to end the patterns of fractal sequence in an operation 2408. For instance, if there are only one, two, or three factors represented the method would proceed to operation 2412. However if there are more than three factors represented the method would proceed to operation 2410. In an operation 2410, the method comprises joining a pattern with a structure geometrically similar to the first pattern (e.g., grid pattern 2500 and tree pattern 2510) until an end of patterns of a fractal sequence. For instance, the determination of an end of a fractal sequence could be based on how many factors are selected for representation in the graphical representation.

FIG. 25B shows a graphical representation with a branch pattern 2518 joined to, within, or as apart of, tree pattern 2510. A branch pattern is made up of all branch axes off a branch axis of the tree pattern. Each branch pattern is joined at an end point of a branch axis. For instance, branch pattern 2518 is joined at an end point 2516 which also forms a midpoint of one of the branch axes (in this case, one corresponding to a factor of stir rate) of the branch pattern 2518.

Branch pattern 2518 and tree pattern 2510 form a fractal sequence (e.g., a tree fractal sequence) with a set of a tree pattern (with only one first pattern) and a set of branch patterns (with four second patterns). In one or more embodiments, the fractal sequence is an ordering of a plurality of sets of patterns, where each pattern of a given one of the plurality of sets of patterns is proportionally smaller than a given pattern of a previous set of patterns in the ordering and attached to one of free endpoints of the previous set of patterns in the ordering. For instance, if there was a third set of patterns in the fractal sequence added to branch patterns 2518, there could be up to 16 third patterns attached to the endpoints of the branch patterns 2518. As with any fractal sequence, theoretically there could be an infinite amount or number of patterns in the sequence that are progressively smaller. Practically, the tree view can handle designs with up to 12 factors and still provide good visual clarity to a user of the graphical user interface 2110. Most experiments do not typically involve more than 12 factors, so this visualization technique is useful in the majority of situations involving the design of an experiment.

FIG. 25B alternatively shows a grid fractal sequence with a small grid pattern 2508 joined to large grid pattern 2500. The large grid pattern 2500 comprises an intersection point 2501 that is the middle point between perpendicular axes. The axes 2504 and 2502 form four quadrants in the window 2506. A small grid pattern 2508 is in each of the quadrants. The generated axes of the small grid pattern 2508 define or otherwise generate a window 2503 that is a portion of the window 2506. The small grid pattern 2508 is joined to the large grid pattern 2500 such that a vertex of the window 2503 is at an endpoint of axis 2502 and/or an endpoint of axis 2504. In this case, a vertex of the window 2503 is also at the intersection point 2501. The same is true for small grid patterns in each of the other quadrants of large grid pattern.

In this fractal sequence for the grid view, the grid fractal sequence comprises an ordering of a plurality of sets of patterns as with the tree view where each pattern of a given one of the plurality of sets of patterns is proportionally smaller than a given pattern of a previous set of patterns in the ordering. With respect to the grid view, each pattern of the given one is within a quadrant formed by respective perpendicular axes in a respective window of a previous set of patterns in the ordering.

FIG. 25B shows an example where the number of factors represented in the graphical representation is even. In one or more embodiments, the graphical representation represents an odd number of factors as shown in FIG. 23 and FIG. 25C. In other words, there is an even-numbered set of factors used in the fractal sequence and a remaining single factor. In one or more embodiments, the generating a plurality of axis (e.g., in operation 2402 of method 2400) comprises generating remaining axes for the remaining single factor that terminates the fractal sequence.

In one or more embodiments, the method 2400 optionally comprises an operation 2412 that includes attaching any remaining axis corresponding to a factor of the design of the experiment to the fractal sequence (e.g., in cases where there are an odd number of factors). In one or more embodiments, attaching any remaining axes comprises determining if there are any remaining axes (e.g., by determining if there are an odd or even number of factors for representation in a graphical representation).

One example of a tree view with an odd number of factors is shown in FIG. 23. Each of the remaining axes comprises a respective middle point between the two endpoints of the respective remaining axes. Each of the remaining axes is attached at free endpoints of axes of the fractal sequence at the middle point.

Another example is a grid view with an odd number of factors as shown in FIG. 25C. In this case remaining axes 2530 corresponding to a factor of concentration intersects each of the vertical axes of the last set of patterns (i.e., axes corresponding to a factor of temperature). Based on the arrangement of the grid view, the remaining axes 2530 also cross the vertical axes corresponding to a factor of catalyst. One of ordinary skill in the art will appreciate that the remaining axes 2530 could have instead intersected each of the horizontal axes of the last set of patterns (here, axes corresponding to a factor of stir rate). Since there were only two level assigned to the factor of concentration, there is only one axes in each of the quadrants formed by the last set of patterns of the fractal sequence. However, if there were more levels, there could be more axes intersecting the vertical (or horizontal) axes of the last set of patterns. For instance, if there were k levels, there would be k−1 axes intersecting the vertical (or horizontal) axes of the last set of patterns.

In one or more embodiments, the method 2400 optionally comprises an operation 2410 that includes determining whether to extend any axes 2414. This is useful in embodiments in which the factors potentially have different numbers of levels assigned to each factor. For instance, a given factor may have more than two levels (or some other minimum number of levels assigned to a factor). In a scenario in which it is determined that an extension is useful to represent more levels, in an operation 2416, there is an extension of a selected axis.

Figure 26A:
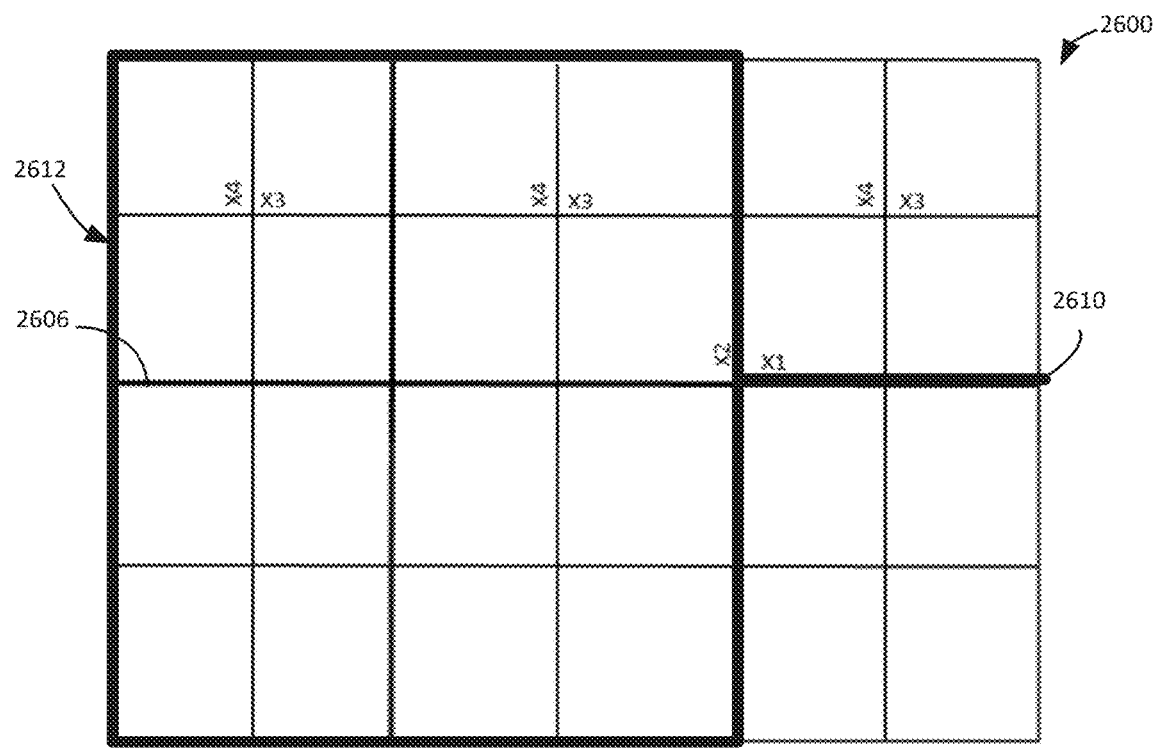
FIGS. 26A-26C illustrate example graphical representations involving multiple factors, with some factors having more than two levels according to a grid view in at least one embodiment of the present technology.
Figure 26B:
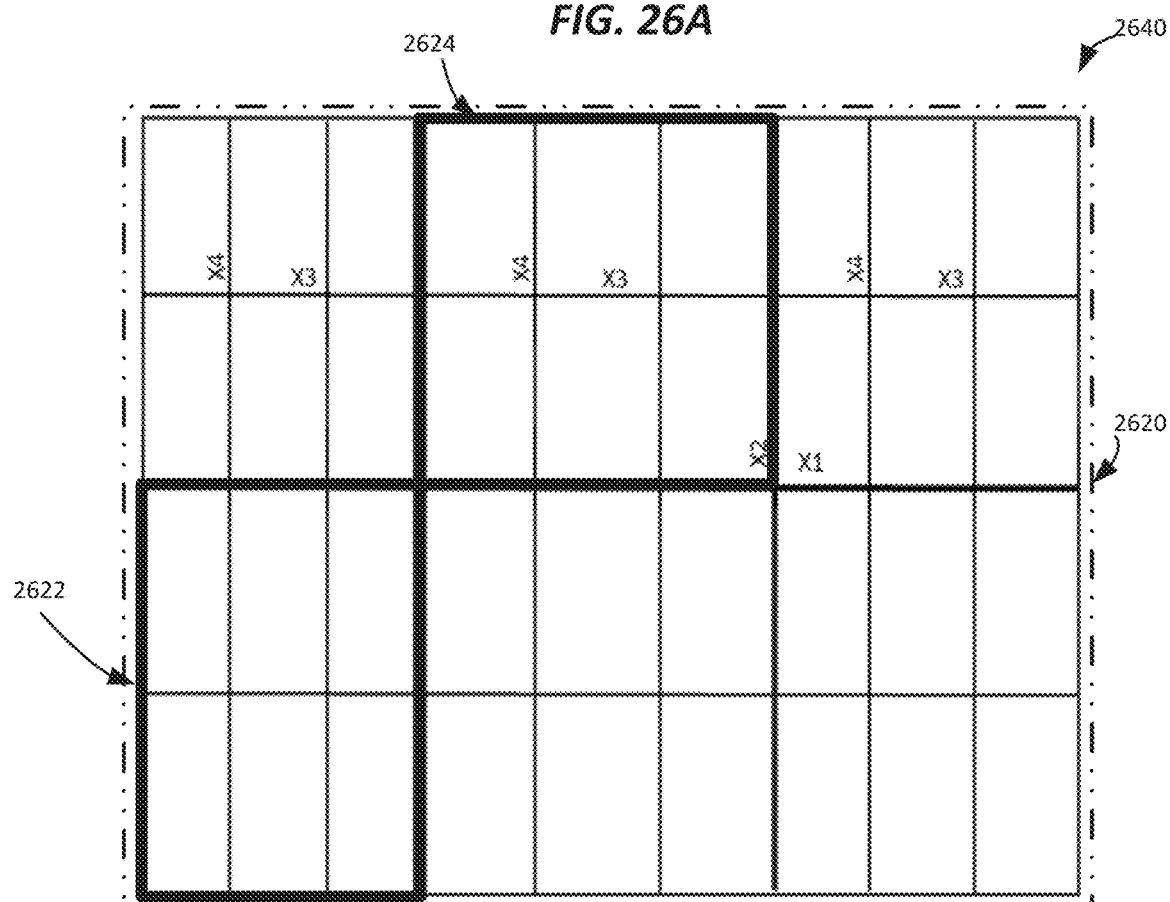
Figure 26C:
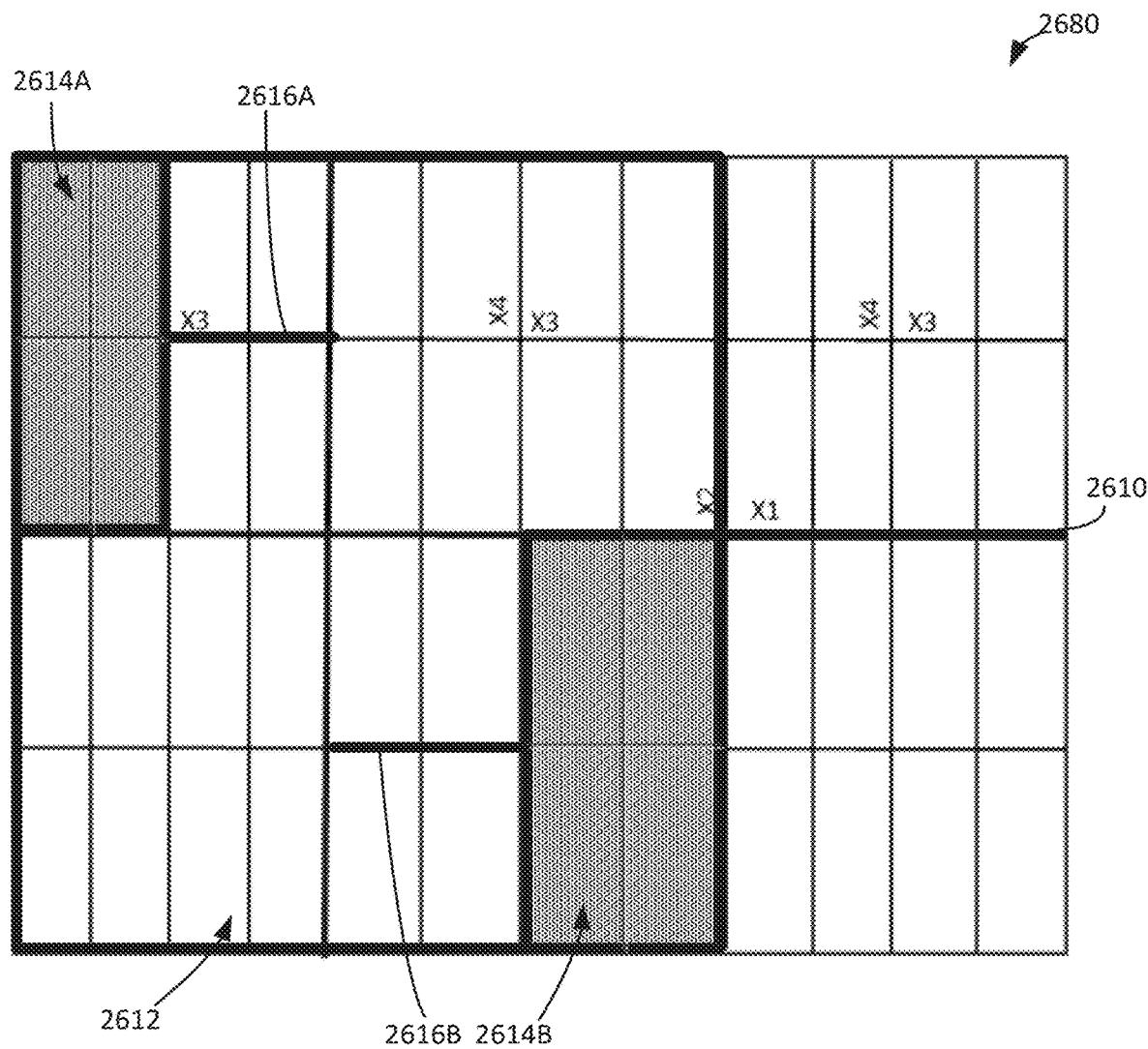

FIGS. 26A-26C illustrate example graphical representations involving multiple factors, with some factors having more than two levels according to a grid view where it may be necessary to extend one or more axes of a fractal sequence. For instance, in one or more embodiments (e.g., ones involving a grid view), a given pattern of the fractal sequence has a first axis of perpendicular axes of the given pattern corresponding to a first factor with k number of levels where k is more than two. The computing device generates the graphical representation with an extended axis from an endpoint of a second axis of the perpendicular axes perpendicular to the first axis with k−1 perpendicular axes spaced on the combined second axis and extended axis, the perpendicular axes corresponding to the first factor of the first axis.

In FIG. 26A-C there are factors X1-X4 displayed in a graphical representation 2600 according to a grid view as described herein. In FIG. 25A, X1, X3, and X4 have two levels allocated to each, and X2 has three levels allocated to it. The X1 axes has an extended axis component 2610 from an endpoint of the main axis 2606 of the first pattern 2612. The entire X1 axis is a combination of the main axis and the extend axis component 2610. Spaced on the X1 axis, are k−1 perpendicular axes where k is equal to the number of levels assigned to the X2 factor.

In FIG. 26B, X1 and X3 have two levels allocated to each, and X2 and X4 has three levels allocated to it. The factors are displayed in a graphical representation 2640 according to a grid view as described herein. Since, the patterns have a common factor for each of respective vertical and horizontal axes, the operation 2414 could involve determining that no extension is necessary. Rather the fractal pattern has a large grid pattern 2620 and a set of small grid patterns (e.g., small grid pattern 2622) joined to the first pattern at the four endpoints of the perpendicular axes of the large grid pattern 2620. There are also interior small grid patterns (e.g., interior small grid pattern 2624) joined to the large grid pattern 2620 at points corresponding to levels of the factors of the grid pattern. Alternatively, this graphical representation could be generated using an extension approach as described with respect to FIG. 26A and FIG. 26C if the pattern of the fractal sequence where different.

In FIG. 26C, X1 and X3 have two levels each; X2 has three levels; X4 has four levels. The factors are displayed in a graphical representation 2680 according to a grid view as described herein. Large grid pattern 2612 has been extended as described with respect to FIG. 26A. In this case small grid pattern 2614 is also extended. FIG. 26C shows two of the small grid patterns 2614A and 2614B with respective extension components 2616A and 2616B. As shown the extension of an extended axis can go in either direction. FIG. 26C shows extended axes 2616 going toward the perpendicular axes of the large grid pattern 2612. FIG. 26C also shows patterns that are proportionally similar in each of two dimensions of the graphical representation 2680. However, they are proportional by a different multiplication factor in individual dimensions.

One of ordinary skill in the art will appreciate a computing device may generate graphical representations with an extended self-similar fractal structures with operations completed in different orders than described in the method 2400 (e.g., for computational efficiency). For instance, the graphical representation in FIG. 26C, may generate a main axis and simply intersect that main axis with axis with k−1 axis where k is the number of levels of the next generated axis (i.e. X2) and the graphical representation may be built using a series of intersection to generate the same extended self-similar fractal structure of FIG. 26C according to an intersecting approach. Similarly, a graphical representation according to a tree approach can be generated according to a series of intersections of axes according to an intersecting approach. Further, the generating a graphical representation in one or more embodiments, comprises determining the graphical representation and the displayed graphical representation is done all at once based on a determined graphical representation.

Figure 27A:
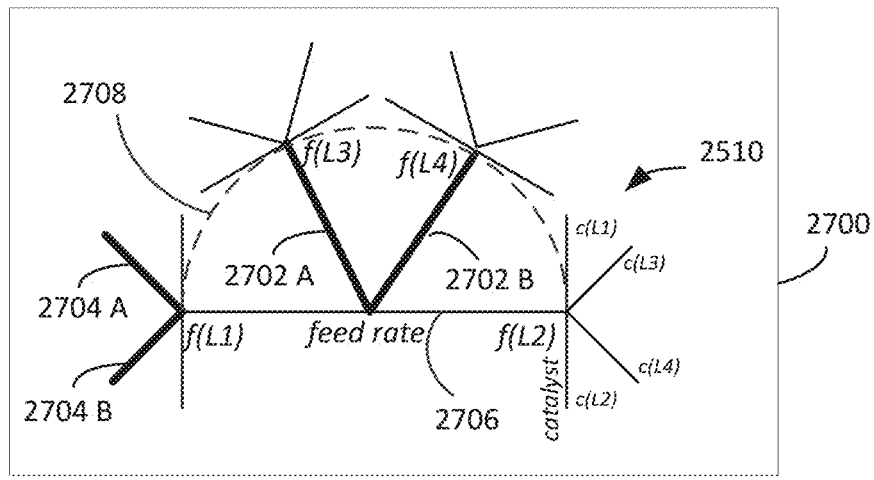
FIGS. 27A-27B illustrate example graphical representations involving multiple factors, with some factors having more than two levels according to a tree view in at least one embodiment of the present technology.
Figure 27B:
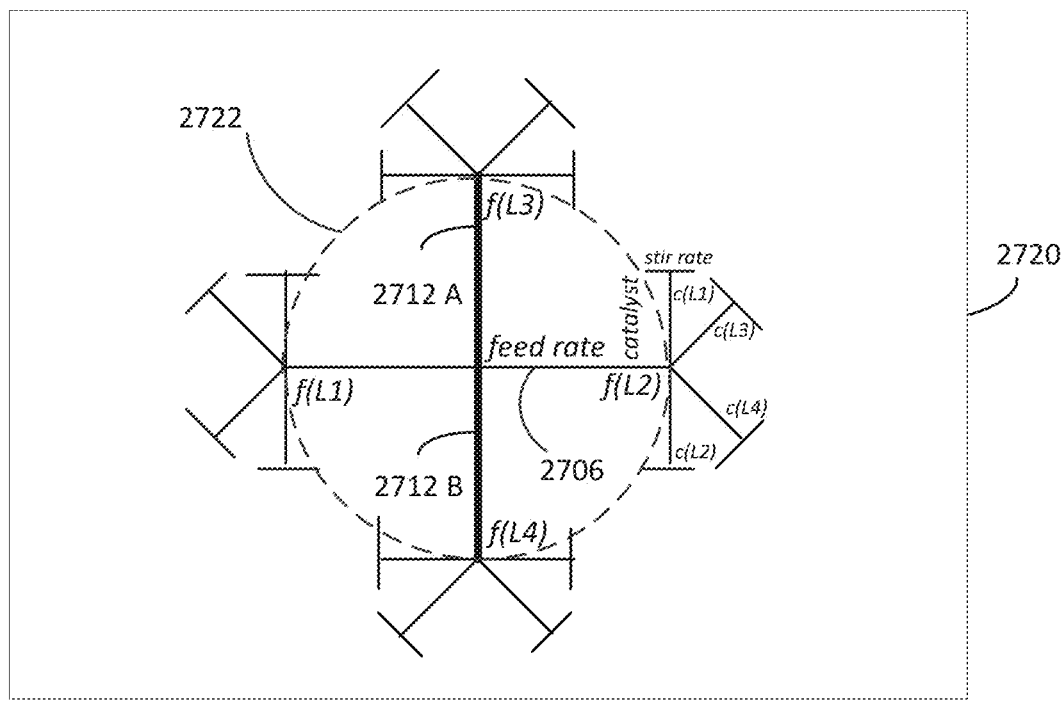

FIGS. 27A-27B illustrate example graphical representations involving multiple factors, with some factors having more than two levels according to a tree view with a design 2700. In this case, a region (e.g., a half-circle or circle) around the axes of the graphical representation (e.g., axes forming a fractal sequence) can be used to provide additional extension branches to represent additional levels for a given factor. In FIG. 27A, the first pattern 2510 has extension axes 2702 branching off an approximately middle point of the main axis. In this case, a factor represented by the main axis has four levels assigned (e.g., a feed rate factor with four possible different feed rates). In the design of 2700, the main axis 2706 forms an upper angle of 180 degrees, and the location of the extension axes 2702 in a half-circle region 2708 above the main axis 2706 are determined in that half-circle region 2708 based on a division of the 180 degrees to provide the maximum region between axes branching off the main axis 2706. This provides better visual clarity between factors. In this case, a factor assigned to the branches of the main axis also has four levels. A similar approach of dividing an upper angle (i.e. upper determined relative to proximity to a main axis) of 180 degrees is used for providing extension branches 2704 off the branches of the first pattern and extension axes 2702 (e.g., for a catalyst factor with four possible catalyst types). Other locations could be selected for extension axes 2702 and extension branches 2704. For instance, axes could be placed closer together to demonstrate a relationship between them (e.g., a relationship between the factors corresponding to the axes). Alternatively, extension axes 2702 could be added in the lower angle below the main axis 2706.

FIG. 27B has an alternative design 2720 in which an entire 360 degrees is used surrounding the main axis 2706 for placing extension axes 2712 in a circle region 2722 surrounding the main axis 2706. As shown this provides better visualization for more factors. The design 2720 also shows an example where there are three factors with the last factor having two levels (e.g. stir rate factor). Subsequent axes can be added differently (e.g., using only 180 degrees).

FIGS. 26A-C and FIGS. 27A-B gave examples of extension of a fractal sequence. Those of ordinary skill in the art could appreciate reductions of a fractal sequence (e.g. not branching in both directions from a main axis for only one level assigned to a factor) or removing axes in response to selecting fewer factors.

In one or more embodiments, the graphical representation represents data correlated with the design of the experiment. For instance in one or more embodiments, the method 2400 comprises an operation 2418 that includes populating the graphical representation with the plotted data (e.g., data 2140) based on information related to the design of the experiment.

As an example, the information related to the design of the experiment could be unique numbers assigned to test cases within the design of the experiment FIG. 23 shows an example graphical representation 2312 populated with plotted unique numbers of the test cases. The run numbers are displayed at end points of the graphical representation based on the test conditions of that experiment as described herein. In one or more embodiments, a computing device displays an interactive graphical user interface (e.g., interactive graphical user interface 2300) with the graphical representation 2312 comprising the unique numbers.

FIGS. 25-25C show examples of run placement in a grid view in which the run numbers are placed within quadrants of a window of the fractal sequence. As shown in FIG. 25A, since the graphical representation with large grid 2500 is collapsed down to only two factors multiple runs are placed within a given quadrant. Similarly, large tree pattern 2510 has multiple run numbers placed at endpoints of the tree pattern.

One or more embodiments described herein, presents a technical improvement over prior art techniques by providing a two-dimensional representation to a user of a graphical interface of a design having more than three factors and/or more than two levels assigned to the different factors.

FIG. 28 shows a prior art technique in which a three-dimensional representation is computed to show three factors in more than two levels and each of the factors only has two levels assigned (a "+" level and a "−" level). A single cube could not be used by itself to show more than three factors. Thus, claimed embodiments, provide an advantage of this computing technique by providing a two-dimensional representation of three or more factors. One or more embodiments herein could also be represented three-dimensionally (e.g., using a three dimensional fractal pattern or having extension axis that extended out from a plane formed by a two-dimensional pattern).

One or more embodiments described herein present other technical improvements in specific application that will be described in more detail below. Each of these different examples below are applicable to multi-factor, multi-level applications as described herein. For simplicity examples are described with respect to multiple factor applications, where each factor has two levels.

For instance, one or more embodiments provide an improvement for determining the quality of a design. For instance, a computing device displays in proximity to the graphical representation an indication of a holistic score for the design of the experiment (e.g., a design efficiency).

FIGS. 29A and 29B show an example interactive graphical user interface 2300 including a design metrics section 2900 to display one or more holistic scores for evaluating a design of an experiment. For clarity other components of data control 2320 are omitted from FIGS. 29A and 29B. Other control components of interactive graphical user interface 2300 may or may not be present in the example provided with respect to FIGS. 29A and 29B.

In the design metrics section 2900, there are three columns: Current Design 2920, Saved Design 2922, and Original Design 2924. The Current Design 2920 column shows the metrics for the design currently being displayed. In one or more embodiments, manipulating a representation of the factor of the experiment changes the holistic score for the design. For example, a value in the Current Design 2920 column will update in response to a change to the displayed design.

Two popular design metrics for assessing experimental designs are Determinant-efficiency (D-efficiency) 2932 and Average-efficiency (A-efficiency) 2934. As the user changes the factor levels in the particular run, efficiency values will change accordingly to reflect the metrics for the current design. For example, as shown in FIG. 29A, the test condition 2910 is "1" and in FIG. 29B the test condition 2910 is changed to "−1". Accordingly, the D-Efficiency values and A-Efficiency values of the Current Design 2920 have changed.

D-Efficiency is the efficiency of the design to that of an ideal or hypothetical orthogonal design in terms of the D-optimality criterion. A design is D-optimal if it minimizes the volume of the joint confidence region for the vector of regression coefficients according to equation (12):

$$D-\text{Efficiency} = 100\left(\frac{1}{n}|X'X|^{\frac{1}{p}}\right) \quad (12)$$

where X is the model matrix, n is the number of runs in the design and p is the number of terms, including the intercept, in the model.

A-Efficiency is the efficiency of the design to that of an ideal orthogonal design in terms of the A-optimality criterion. A design is A-optimal if it minimizes the sum of the variances of the regression coefficients according to equation (13):

$$A-\text{efficiency} = 100p/n\text{Trace}(X'X)^{-1})) \quad (13)$$

where X is the model matrix, n is the number of runs in the design and p is the number of terms, including the intercept, in the model.

Other evaluations could be made (e.g., G-efficiency, average variance of prediction, design creation time, etc.). Design creation time is useful in environments in which it may take greater computational time to compute a given experiment outcome based on levels selected for an individual test cases.

Saved Design 2922 column represents visually a storage of the values for a design saved by the user and will update when the user of the graphical user interface 2300 indicates to do so (e.g., by clicking the Save Current Design button 2940) or the user changes the graphical representation (e.g., to project over more or less factors). The values in the Saved Design 2922 column will then change to those shown in the Current Design 2920 column. Original Design 2924 column represents visually a storage of the values for the original design used to generate the initial design and will change only for projection changes. Values in the Saved Design 2922 column and Original Design 2924 column provide the user of the graphical user interface 2300 with a standard for comparing different designs.

As shown in FIG. 29B, changing the Feed Rate 2322 test condition 2910 increased the D-Efficiency 2932 and A-Efficiency 2934 which is a desirable improvement, and the user most likely would save this design. However, if the efficiency had not approved as desired, the user of the graphical user interface 2300 could instead use controls such as the Revert to Saved Design button 2944 or Revert to Original Design button to revert to a better design. Additionally or alternatively, even though the efficiency score may be objectively worse, the user may still save the design if the design achieves other goals (e.g., filling in coverage holes). For instance, a user of the graphical user interface 2300 can evaluate the difference in an efficiency score in conjunction with the visual representation to determine a trade-off with loss of efficiency versus filing in coverage holes.

In one or more embodiments, the user of the graphical user interface 2300 can project down to fewer factors (e.g., unchecking boxes shown in factor control 2330 of FIG. 23) to make improvements in efficiency in that projection and then return back to the original design to see how their changes affected the overall design. For instance, there may be improvements at a lower projection, but result in a slightly worse overall design. The user can then decide whether to accept this loss in efficiency or stick with the original saved design.

In one or more embodiments, the computing device generates the experiment (e.g., a computer simulation experiment) in response to user input. For instance, the user can click the Make Design button 2942 to indicate to the computing device to generate and run an experiment.

One or more embodiments described herein present technical improvement for applications involving conducted experiments according to a design. For instance, in one or more embodiments, a computing device receives results of the experiment according to the design of the experiment. Results can be provided by user input or from a computing device or system performing the testing (e.g., if the computing device is performing the testing). This is also useful for screening to identify key factors that affect responses in an experiment.

The computing device receiving the results can populate the graphical representation with values. Each of the values corresponds to a result of each of the test cases for the experiment according to the design. An example of a viewer that provides analysis of response data is the analysis fractal by SAS Institute Inc. of Cary, N.C. The computing device displays the interactive graphical user interface of the graphical representation comprising the values.

FIGS. 30A-30D illustrate an example graphical representation depicting representations of results of an experiment conducted according to the catalyst experiment as described herein (e.g., in a viewer 2310 in graphical user interface 2300). Instead of row numbers for test cases as shown in FIG. 23 for the catalyst experiment, the value of the results (i.e. a response) of the experiment can be plotted. With the interactivity, a user can see if there are particular regions of interest for the response related to just a few factors. Fitting a model would already give an indication to large effects, which would provide a natural ordering. The plotted values in FIG. 30A where values given for the response (percent rated). The goal of the catalyst experiment is to maximize the response, so higher values are more desirable.

Figures 30A, 30B:
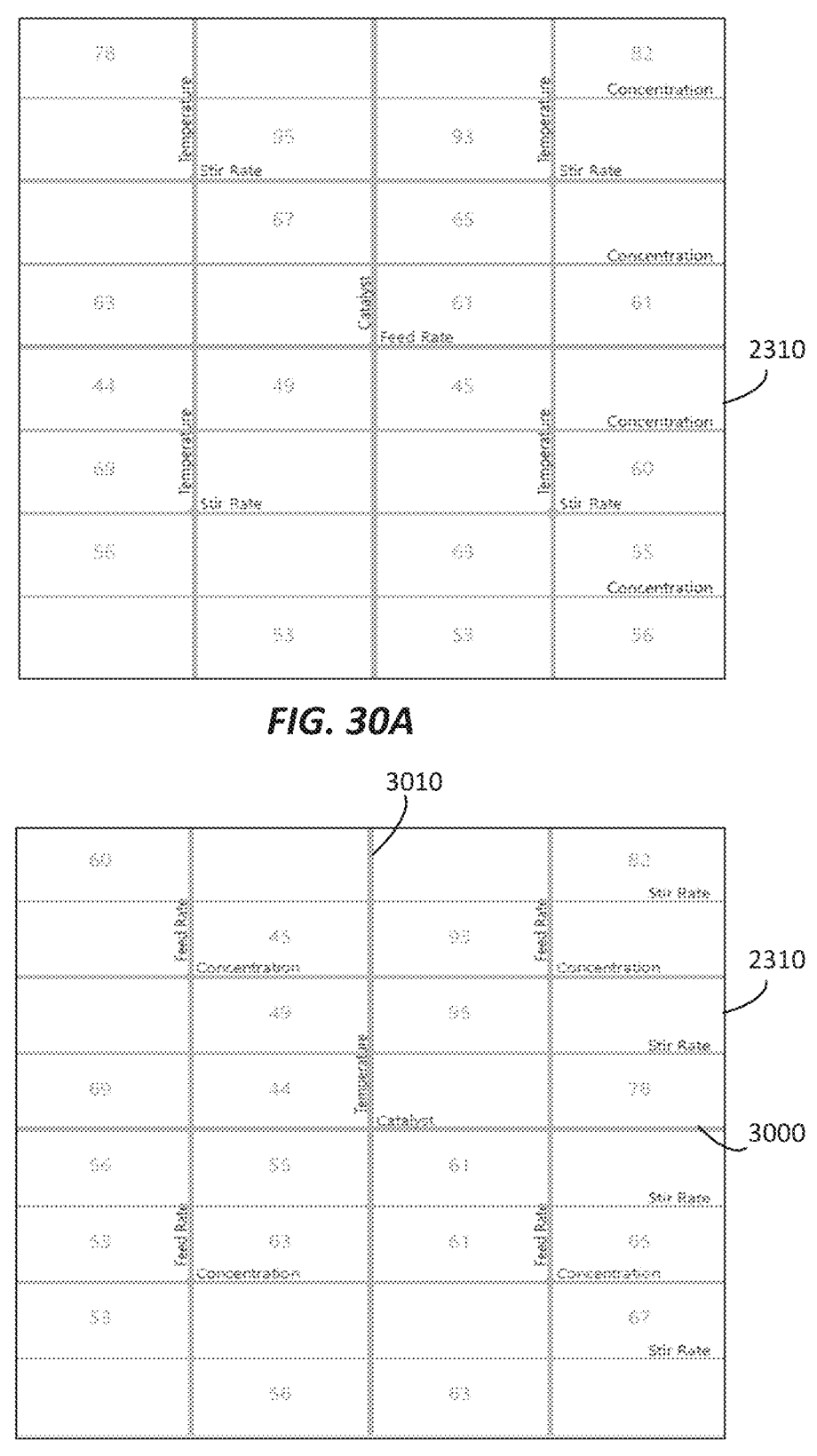

In one or more embodiments, where the computing device receives information comprising results of the experiment according to the design of the experiment, the computing device can select a prioritization of the plurality of axes in the fractal sequence based on the results of the experiment (e.g., in response to testing result or user input). For instance, FIG. 30B illustrates a graphical representation in viewer 2310 depicting results of an experiment with the priority of all the factors (i.e., catalyst, temperature, concentration, feed rate, and stir rate) reordered based on analysis performed by the computing device. In particular, the computing device performed a regression analysis and reducing the model (not shown) suggests the significant terms are the main effects for Catalyst, Temperature, and Concentration, and the interactions Catalyst*Temperature and Temperature*Concentration. Then the graphical representation in the viewer 2310, although still showing all the factors, has catalyst, temperature and concentration shown more prominently. For instance, a catalyst factor is correlated with a main axis 3000 instead of a feed rate factor. A temperature factor is correlated with an axis 3010 that intersects main axis 3000 as part of a first pattern. Alternatively, a user could manually select particular factors to find the most significant factors using, e.g., the factor control 2330 of FIG. 23.

Figure 30C:
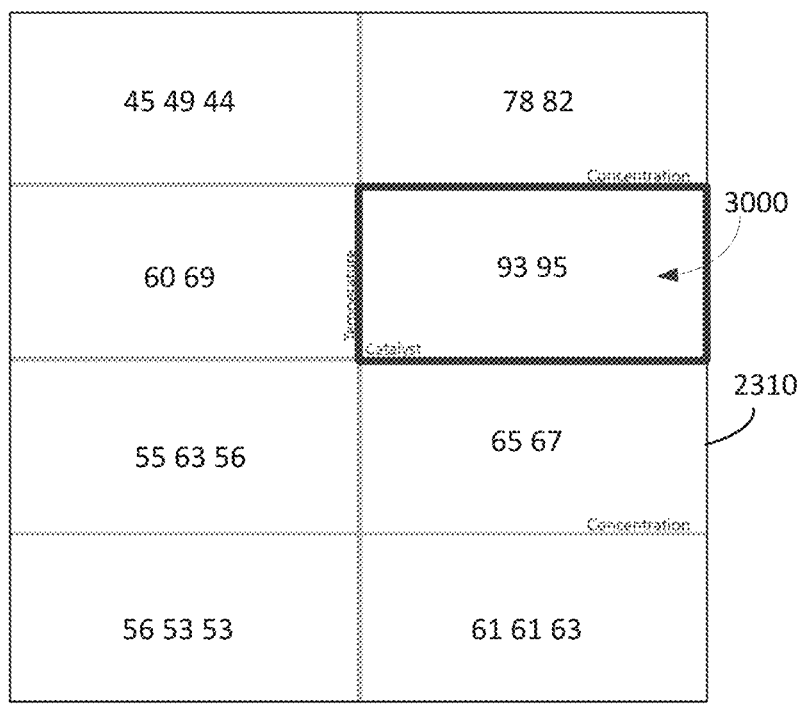

FIG. 30B shows the graphical representation after reordering the plot hierarchy. FIG. 30C is the reordered plot hierarchy, but with the factors Feed Rate and Stir Rate projected over. By examining either of these figures, one can see Catalyst at the high level, Temperature at the high level, and Concentration at the low level provide noticeably larger responses as shown in region 3000 of the viewer 2310.

The plot could also be useful for residual checking by investigating a few potentially significant interactions (based on the given model) that were not originally included. If one sees a pattern in the graphical representation, it can suggest the model is missing one or more terms. For example, consider the reactor data if main effects for Catalyst, Temperature, and Concentration, and the interactions Catalyst*Temperature were included in the model, but Temperature*Concentration was not.

As shown in FIGS. 30A-30C, in one or more embodiments, the results of the experiment are an observed result after conducting the experiment Another way to look for patterns is to plot predicted results, e.g. to determine the design of the experiment.

Figure 30D:

Another way to look for patterns in data is to plot residuals where a residual is the difference between an observed result and a predicted result FIG. 30D shows a graphical representation plotting the residuals (rounded to 1 decimal place) for the experiment shown in FIGS. 30A-30C. Not only does the graphical representation suggest the residuals have issues with independence, it even points to which term is missing based on the pattern of the residuals.

Figures 31A, 31B:
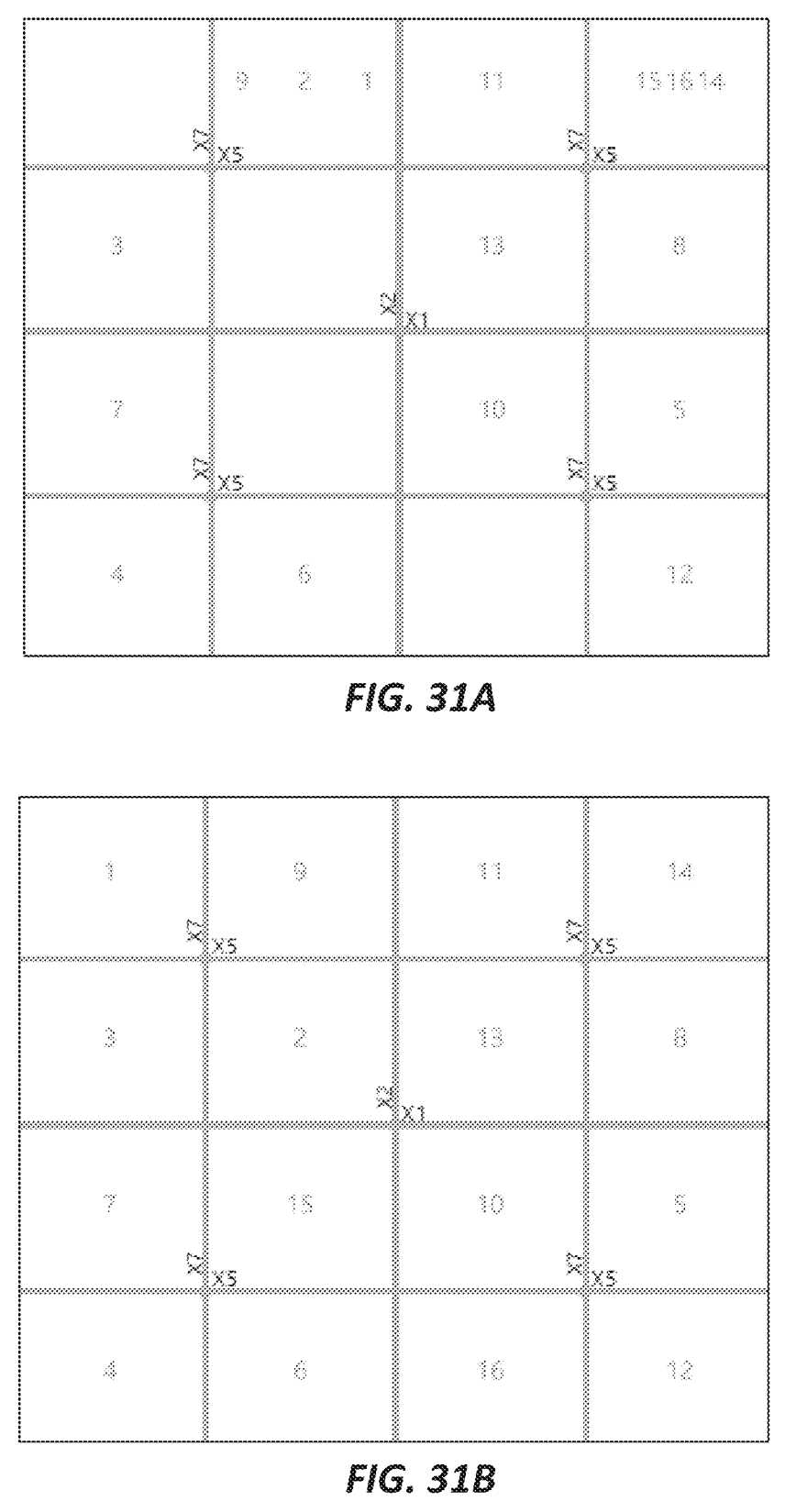

One or more embodiments described herein present technical improvement for applications involving designing or otherwise diagnosing a designed experiment with a particular strength for a combinatorial test design as described herein. In particular, one or more embodiments, provide a tool to investigate particular projections of interest such as how well factors are covered and what needs to be done to make a projection of interest have full coverage. FIGS. 31A-31B illustrates graphical representations for diagnosing covering arrays in at least one embodiment.

Consider a strength 2 or 3 covering array as described herein, with a graphical representation showing four factors of seven factors (i.e., investigating projections into 4 dimensions). FIG. 31A shows a strength 3 binary covering array (that is, any three-factor projection contains every level combination at least once) in 16 runs representing factors X1, X2, X5, and X7. FIG. 31A presents a covering array of a binary case (i.e. 2 level inputs for each factor). However, this same technique could be used for mixed-level covering arrays or covering arrays with more than two levels for one or more factors. FIG. 31A shows four gaps in coverage.

One or more embodiments include a graphical user interface (e.g., graphical user interface 2300) that allows a user to manually adjust the graphical representation or data plotted by the graphical representation as described herein to fill in gaps for the particular projection. In this case runs 1, 2, 15, and 16 can be adjusted to fill in the gaps. That is, (X1, X2, X5, X7) should be (−1, 1, −1, 1), (−1, 1, 1, −1), (−1, −1, 1, 1) and (1, −1, −1, −1). FIG. 31B shows an adjusted design to provide better coverage in the particular projection of interest for factors X1, X2, X5 and X7.

One or more embodiments herein are useful in conjunction with manipulating free cells (also known as "do not care" cells). These are cells in a strength t covering array that do not contribute to the t-Coverage of the covering array. This means that they can be changed to any value from the range of values for the factor without affecting the t-Coverage of the covering array.

FIG. 31A shows a data control 3200 in a graphical user interface 3230 (e.g., graphical user interface 2300) for a design of an experiment comprising seven factors (X1-X7). In one or more embodiments, the computing device displays a representation that test conditions include free cells (e.g., in response to a user marking them as free cells or the computing device allocating certain cells as free cells). Data control 3200 optionally has a Do Not Care 3210 column for toggling each cell in an entire run or row as a free row of do not care cells (i.e. runs 2, 14, 15 and 16). Alternatively or additionally, individual cells could be marked in a particular factor column indicating that the cells may be changed without impacting the coverage of the covering array. This is particularly useful in applications where only some of the cells in a row are free cells. A check mark is shown as an indicator that a cell is a free cell, but any symbol could be used (e.g., a green dot enclosing a check mark). In this example, rows 2, 14, 15, and 16 contain all free cells for each test condition of a row, so these rows could be completely eliminated without affecting 3-Coverage.

One or more embodiments enable manipulation of the free cells to improve a holistic score for the design of the experiment that is a score related to a strength of a combinatorial test design. FIG. 32B shows graphical user interface 3230 comprising a design metrics section 3240 with a holistic score for indicating 3-Coverage 3242 and a holistic score for indicating 4-Coverage 3244. The runs 2, 14, 15, and 16 have been augmented without changing other rows (e.g., run 1), so the 3-Coverage remained at 1. The 4-Coverage in the original design 3245 was only 0.7125 and is now in the current design 3241 improved to 0.78929.

Figure 32C:
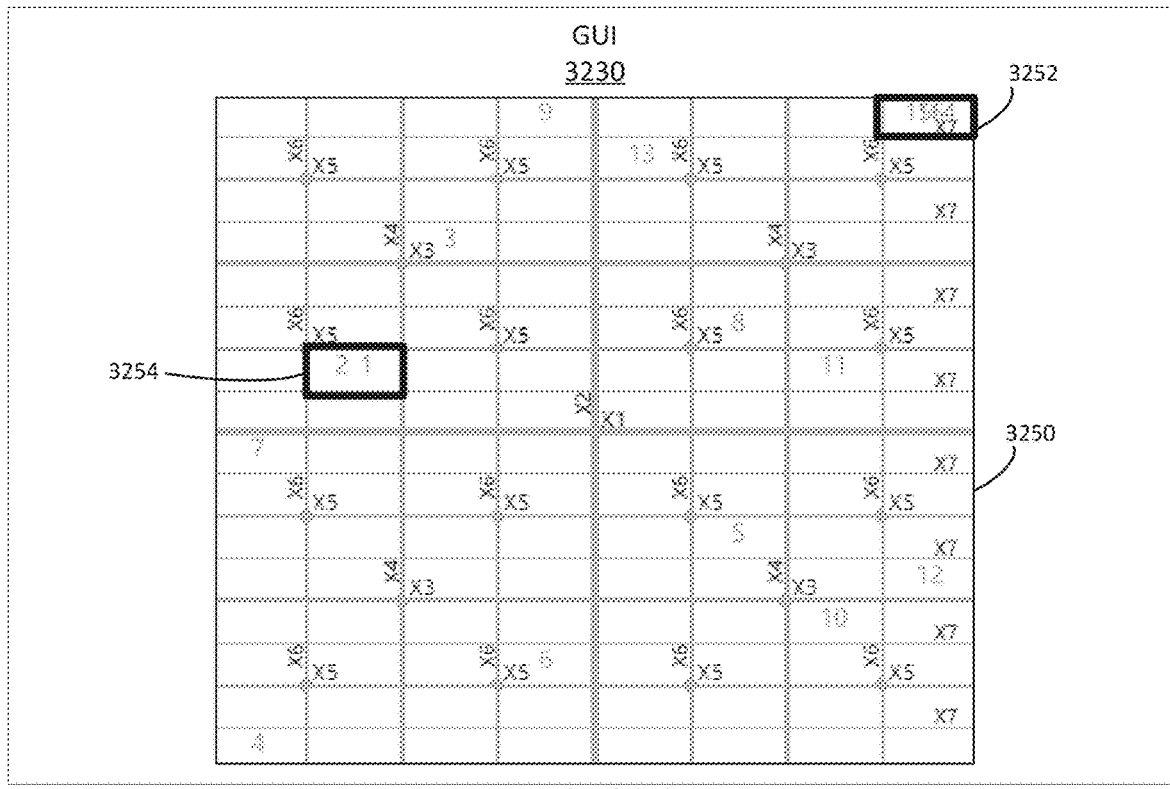
Figure 32D:
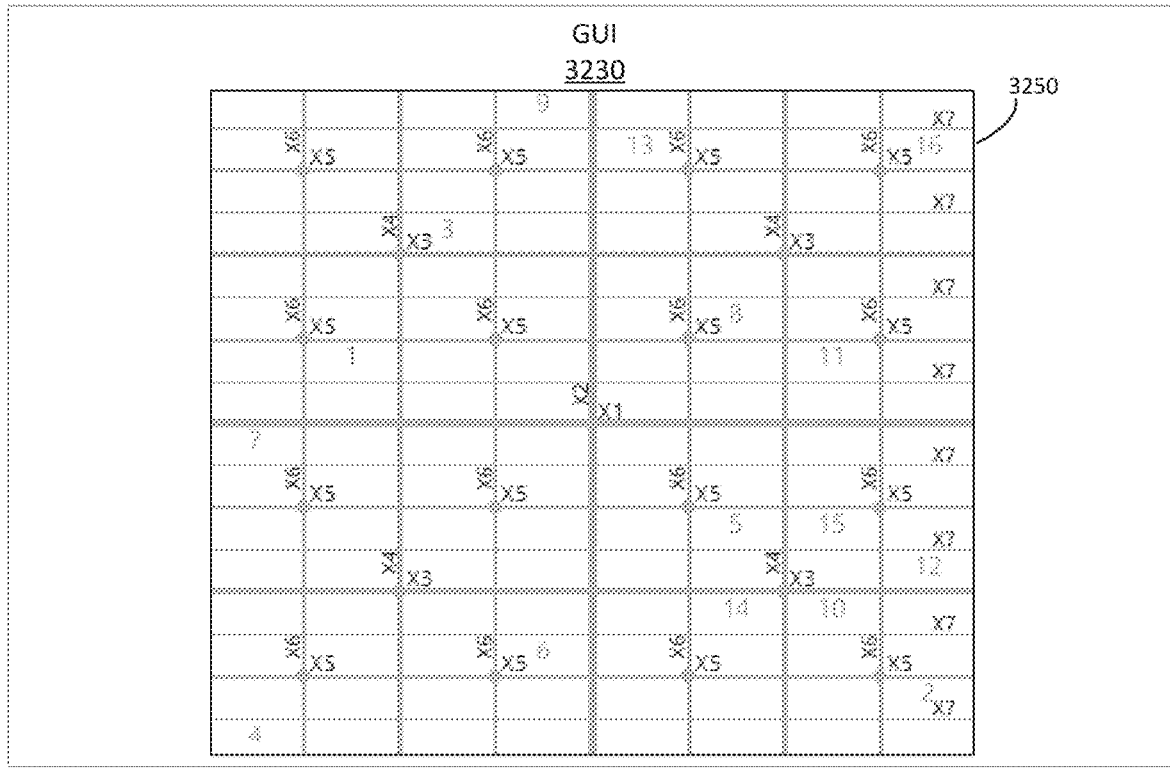

FIG. 32D shows the corresponding graphical representation in a viewer 3250 showing how the design has been optimized to improve coverage from the original design in FIG. 32C. As explained herein, the levels assigned in the data control 3200 could have also been augmented by interaction with the graphical representation. In particular, the viewer 3250 shows that there was duplicate coverage in the original design of FIG. 32C in portions 3254 and 3252 of the viewer 3250. One or more of these test cases could have been manually moved to other portions of the viewer 3250. The new optimized design does not suffer from that same duplication of test cases and is an improved design for an experiment.

One or more embodiments are useful for determining an optimal design for an experiment (e.g., an optimal screening design). For instance, one or more embodiments, are particularly useful in scenarios when the number of factors of an experiment or test runs is too numerous to computationally or visually determine an optimal design for an experiment given time or processing constraints, or in scenarios when there are no known preexisting designs for an experiment given a quantity of requested factors and test cases for an experiment.

Figure 33:
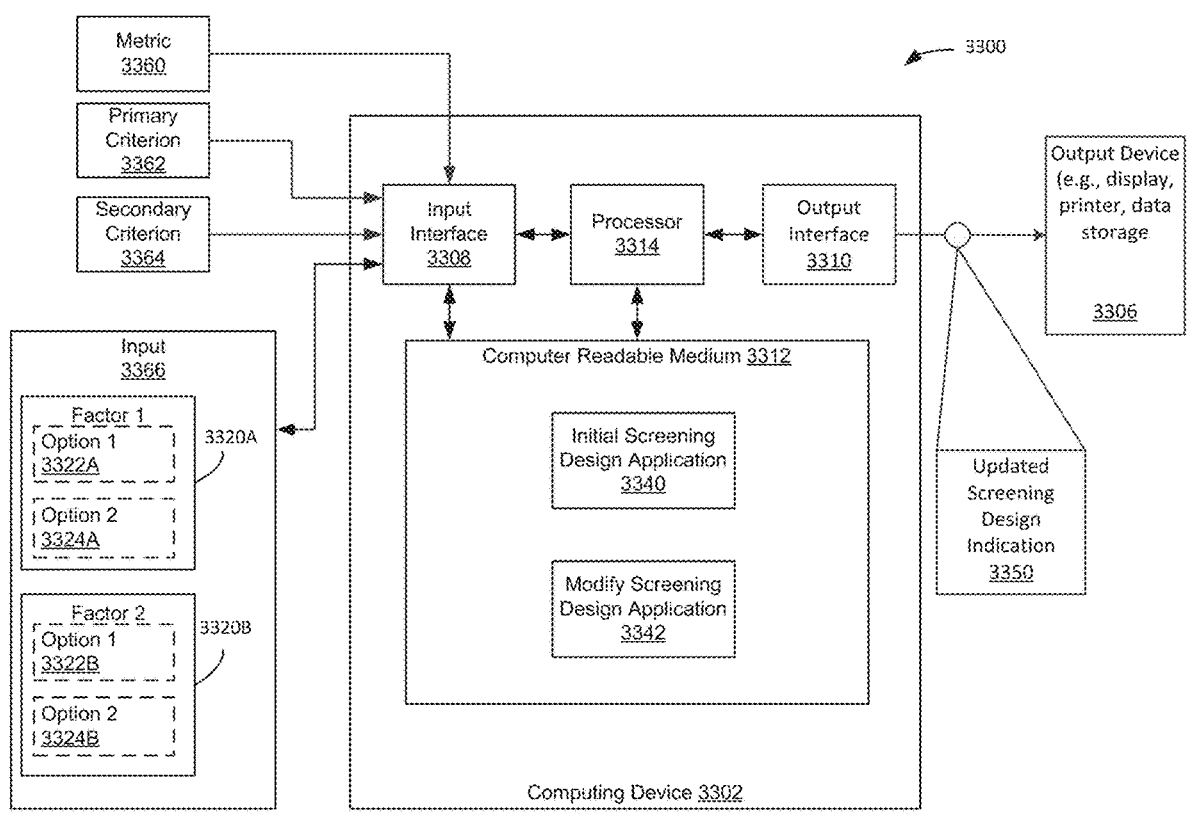
FIG. 33 illustrates an example block diagram of a system for outputting a screening design for an experiment in one or more embodiments.

FIG. 33 illustrates an example block diagram of a system 3300 for outputting a design (e.g., an optimal screening design) for an experiment in one or more embodiments. The system 3300 includes a computing device 3302 useful for outputting a design for an experiment. In one or more embodiments, the computing device 3302 is the same or different from computing devices described herein (e.g., computing device 2102 or computing device 1302).

The system 3300 is configured to exchange information relevant to an output for a design for an experiment between devices (e.g., output device 3306) in the system (e.g., via wired and/or wireless transmission) and/or devices in other systems described herein (e.g., system 1300 and system 2100). For example, a network (not shown) can connect one or more devices of system 3300 to one or more other devices of system 3300, system 2100, or system 1300. In one or more embodiments, fewer, different, and/or additional components than shown can be incorporated into the system 3300 (e.g., components of system 2100 or system 1300).

In one or more embodiments, the computing device 3302 obtains information related to outputting a design of an experiment via an input interface 3308. In one or more embodiments, the input interface 3308 comprises one or more features of an input interface described herein or is an input interface described herein (e.g., input interface 1308). In one or more embodiments, the computing device 3302 obtains metric information (e.g., metric 3360). The metric information includes, for example, a metric indicating a quantity of test cases for an output design of an experiment Quantity is also sometimes referred to as a number or amount (e.g., a number of test cases or amount of test cases). The information may be obtained by the computing device 3302 by receiving the information (e.g., entered from a user of the computing device 3302). A metric could be entered or selected by a user from a qualitative label that represents or indicates a metric N As for example, a user could select a qualitative label of a high number of runs to represent a metric of 300 or more test cases. In one or more embodiments, the system 3300 includes (e.g., input or output devices described herein) for receiving information related to the design of an experiment and providing it to the computing device 3302 (e.g., sending or transmitting over input interface 3308). Alternatively, the information is obtained from one or more default values stored in the computing device 3302 (e.g., in computer readable medium 3312).

In one or more embodiments, the computing device 3302 obtains other information relating to a design of an experiment. For instance, the computing device may receive input 3366 indicating multiple factors for the output design. For instance, the input 3366 could be metric information indicating a number of factors (e.g., factors 3320) and options for those factors (e.g., options 3322). Additionally or alternatively, input 3366 could be labels for the particular factors and labels for the options associated with the experiment. For instance, if the experiment were an experiment for a chemical process, the input 3366 could be labels received from a user for factors relevant to the chemical process (e.g., catalysts used, temperature of the solution, stir rate, etc.). The option labels assigned to each factor could be discrete (e.g., different catalyst types) or continuous (e.g., a range of possible temperatures or stir rates). Alternatively, or additionally, the computing device 3302 could have a default number of factors or options (e.g., a default option of 2 for factors that do not specify particular options).

In one or more embodiments, the computing device 3302 obtains one or more criterion for scoring or otherwise evaluating the output design. For instance, the computing device 3302 obtains a primary criterion 3362 and a different secondary criterion 3364 (e.g., criteria that an optimal design would satisfy). The one or more criterion may be input by the user of the computing device 3302 (e.g., by selecting amongst different options for the design). In one or more embodiments, the computing device 3302 displays a graphical user interface (e.g., on an output device 3306) indicating multiple criterion for the primary criterion and/or the secondary criterion for user selection. The computing device 3302 receives user input indicating a selected one or multiple ones of each of a primary criterion or secondary criterion. Additionally or alternatively, the one or more criteria are default values for determining an optimal design.

In one or more embodiments, the computing device 3302 is useful for determining an optimal screening design for an experiment. A screening design is used for identifying one or more active factors of the experiment each of which independently effect an outcome of a given test case of the experiment A common goal of screening designs is to screen through only those inputs that have the greatest effect on the output. Based on the principle of sparsity of effects, a system is usually dominated by only a few factors or low level interactions between factors. Other potential effects, such as interactions between factors and curvature effects, are typically of less importance at the screening design stage.

In one or more embodiments, the primary criterion is used as a measure of design quality for the effectiveness of a screening design. For instance, the primary criterion is related to scoring an efficiency of a screening design at identifying the one or more active factors of an experiment each of which independently effect an outcome of a given test case of the experiment.

In one or more embodiments, the designer of the experiment has additional goals beyond determining an optimal screening design for an experiment. For instance, there may be multiple optimal screening designs and a user of the computing device 3302 can consider other criteria for the screening design different from the primary criterion.

In one or more embodiments, the computing device 3302 has a computer-readable medium 3312 (e.g., computer-readable medium 2112 or 1312) and a processor 3314 (e.g., processor 2114 and/or processor 1314). For instance, computer-readable medium 3312 comprises one or more features of one or more computer-readable mediums described herein or is one of computer-readable mediums described herein (e.g., computer-readable medium 1312 or computer-readable medium 2112). Additionally, or alternatively, processor 3314 comprises one or more features of one or more processors described herein or is one of processors described herein (e.g., processor 1314 or processor 2114). For instance, in one or more embodiments, computer-readable medium 3312 stores instructions for execution by processor 3314. For example, computer-readable medium 3312 comprises instructions for determining a design of an experiment, evaluating or scoring a design of an experiment, and generating an updated design of an experiment.

In one or more embodiments, the initial screening design application 3340 determines whether there are stored instructions (e.g., stored in a computer-readable medium described herein) for generating an initial screening design for the experiment. The initial screening design is for identifying one or more active factors of the experiment each of which independently affect an outcome of a given test case of the experiment Another words, in one or more embodiments, the initial screening design application 3340 determines whether there is a preexisting stored design (e.g., a known or preexisting design generated from stored instructions) for an initial screening design for the experiment. The preexisting stored design can preexist or is known before any particular obtained input or metrics for an experiment. For instance, the application may have a search or query function for searching, based on possible quantities of factors and test runs for an experiment, stored design instructions for constructing a known or preexisting design. Alternatively or additionally the stored instructions could be related to fetching stored design data or tables correlated with possible quantities of factors and test runs for an experiment (e.g. simple or commonly selected designs may be stored in an electronic library of complete designs). Responsive to determining that there are stored instructions for generating the initial screening design for the experiment, the initial screening design application 3340 selects, using the stored instructions, the initial screening design for the experiment.

In some cases, the initial screening design application 3340 can use stored instructions for an initial screening design to directly construct an output design. For instance, the initial screening design application 3340 determines whether there are stored instructions for generating a test suite correlated with one or more of a possible metric 3360, input 3366 and factors 3320. In some cases, the computing device determines that there are stored instructions and generates, using the stored instructions, an initial screening design for the experiment. In other case, the computing device determines that there are not stored instructions but determines that one or more of the stored instructions can be used to create one or more candidate designs for the experiment. In this case, the initial screening design application 3340, selects one of the candidate designs as the initial screening design. In yet other cases, the computing device determines that there are not stored instructions for the initial screening design for the experiment (e.g., there are not known designs or candidate designs for the experiment), and no selection is performed for an initial screening design for the experiment.

In one or more embodiments, the computer readable medium 3312 comprises stored instructions for generating an initial screening design that is a preexisting design correlated with possible metric 3360, input 3366 and/or factors 3320. In this case, the computing device 3302 can select the initial screening design by executing stored instructions to directly generate, responsive to a given metric indicating an amount of test cases and a given number of factors, one or more candidate initial screening designs. Additionally or alternatively, the computer readable medium 3312 comprises an electronic library of initial screening device correlated with possible metric 3360, input 3366 and/or factors 3320. In this case, the computing device 3302 can select the initial screening design by executing stored instructions for retrieving one or more candidate initial screening designs from memory (e.g., stored in an electronic library).

In one or more embodiments, the initial screening design application 3340 evaluates the initial screening design (e.g., it evaluates a quality of the initial screening design or other criteria for the initial screening design). For instance, the initial screening design application 3340 computes an initial score for a primary criterion for the initial screening design. In one example, the primary criterion is related to a quality of the initial screening design and the initial score indicates an efficiency of the initial screening design at identifying one or more active factors.

In one or more embodiments, the computer readable medium comprises additional applications for refining the initial screening design (e.g., a modify screening design application 3342). The modify screening design application 3342 is shown as a separate application from the initial screening design application 3340 merely as an example. In other examples, functionality described herein for these applications are implemented by a single application or are distributed across different applications. In one or more embodiments, the computing device 3302 comprises a modify screening design application 3342 for determining whether to modify the initial screening design based on modification criteria. For instance, the modification criteria may comprise the secondary criterion in a case where the output design will satisfy or optimize both the first criterion and the secondary criterion. Alternatively or additionally, the modification criteria comprises a quantity of test cases, and indicated factors for the experiment. For instance, the selected initial design may be merely a candidate design as a starting point and modifications are need to ensure an output design has a certain quantity of test cases or factors.

In one or more embodiments, the modify screening design application 3342 responsive to determining, based on the modification criteria, to modify the initial screening design, generates an updated screening design for the initial screening design. For instance, the modify screening design application 3342 generates one or more modified screening designs that each has at least one option for a corresponding test case different from the initial screening design. The modify screening design application 3342 evaluates the one or more modified screening designs by computing a respective score for the primary criterion for each of the one or more modified screening designs. The modify screening design application 3342 determines that each of the one or more modified screening designs satisfies the primary criterion by respectively comparing the respective score for the primary criterion to the initial score for the primary criterion or a threshold score for the primary criterion. The modify screening design application 3342 computes a score for the secondary criterion for a given design of the one or more modified screening designs. The modify screening design application 3342 selects, based on the score for the secondary criterion, a given design of the one or more modified screening designs as the updated screening design.

In one or more embodiments, the modify screening design application 3342 outputs information to output device 3306 via output interface 3310. Output interface 3310 provides an interface for outputting information (e.g., related to a design of an experiment) for review by a user and/or for use by another application or device or multiple applications or devices (e.g., a display, printer, data storage). In one or more embodiments, output device 3306 is a device or is one of devices for displaying information relevant to the experiment (e.g., user selection criteria, design scores, or a design for an experiment).

In one or more embodiments, the computing device 3302 outputs an indication of the updated screening design for the output design of the experiment. For instance, the indication could be the output design itself. As an example, computing device could display, via a graphical user interface, an array for the output design. Each row of the array represents one of the test cases of the experiment and each column of the array represents one of the factors of indicated factors. Alternatively, the updated screening design indication could indicate differences or the presence of differences from a preexisting design (e.g., generated from stored instructions). For instance, the indication could indicate changes in options or a changed evaluation of a design. Output interface 3310 and output device 3306 could be one of or comprise features of output interfaces (e.g., output interface 1310) and output devices (e.g., output device 1306) described herein.

In one or more embodiments, the system 3300 implements a method as described herein (e.g., a method shown in FIGS. 34A and 34B and FIG. 40) for outputting a design for an experiment.

Figure 34A:
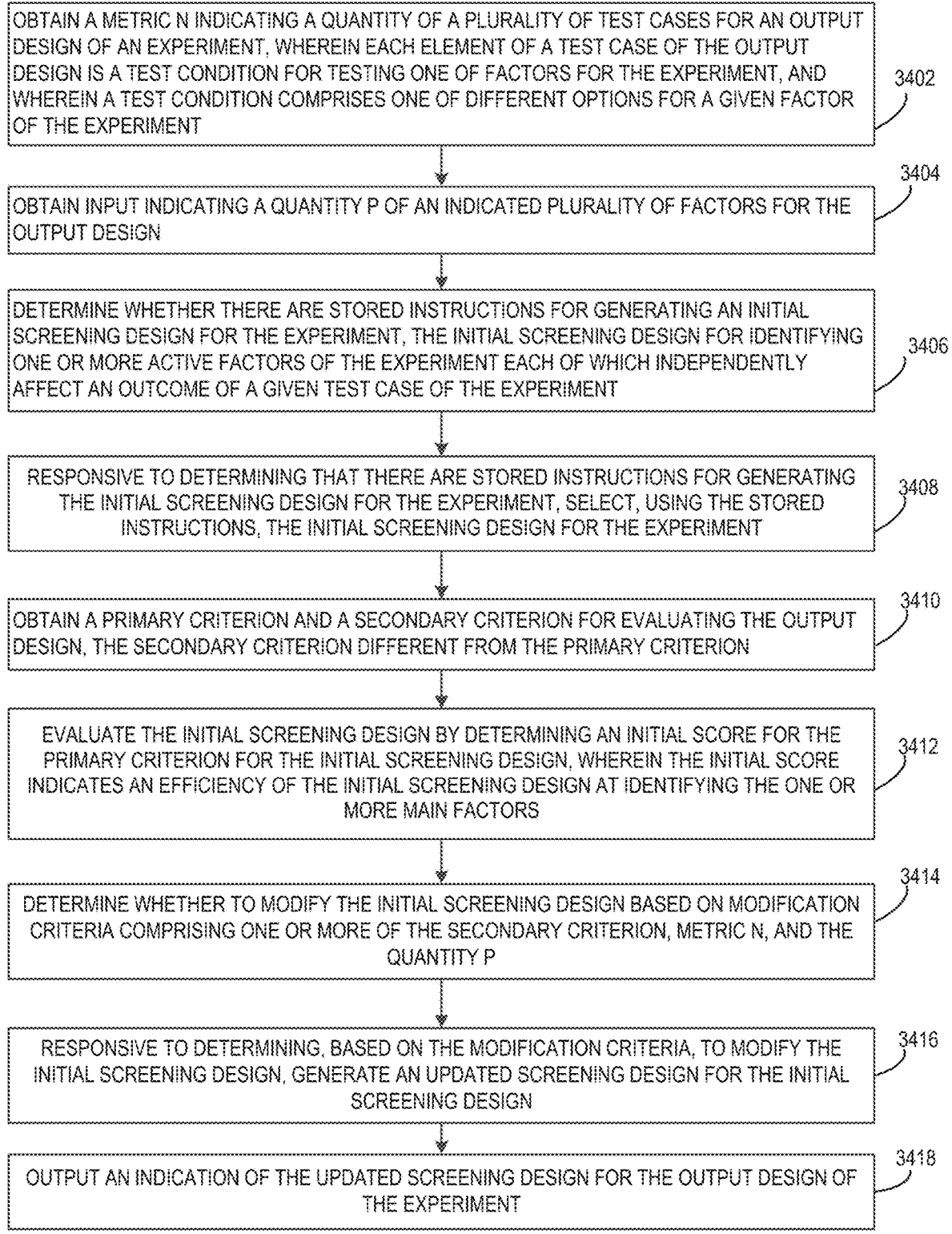
FIGS. 34A and 34B illustrate an example flow diagram for outputting a screening design for an experiment in one or more embodiments.
Figure 34B:
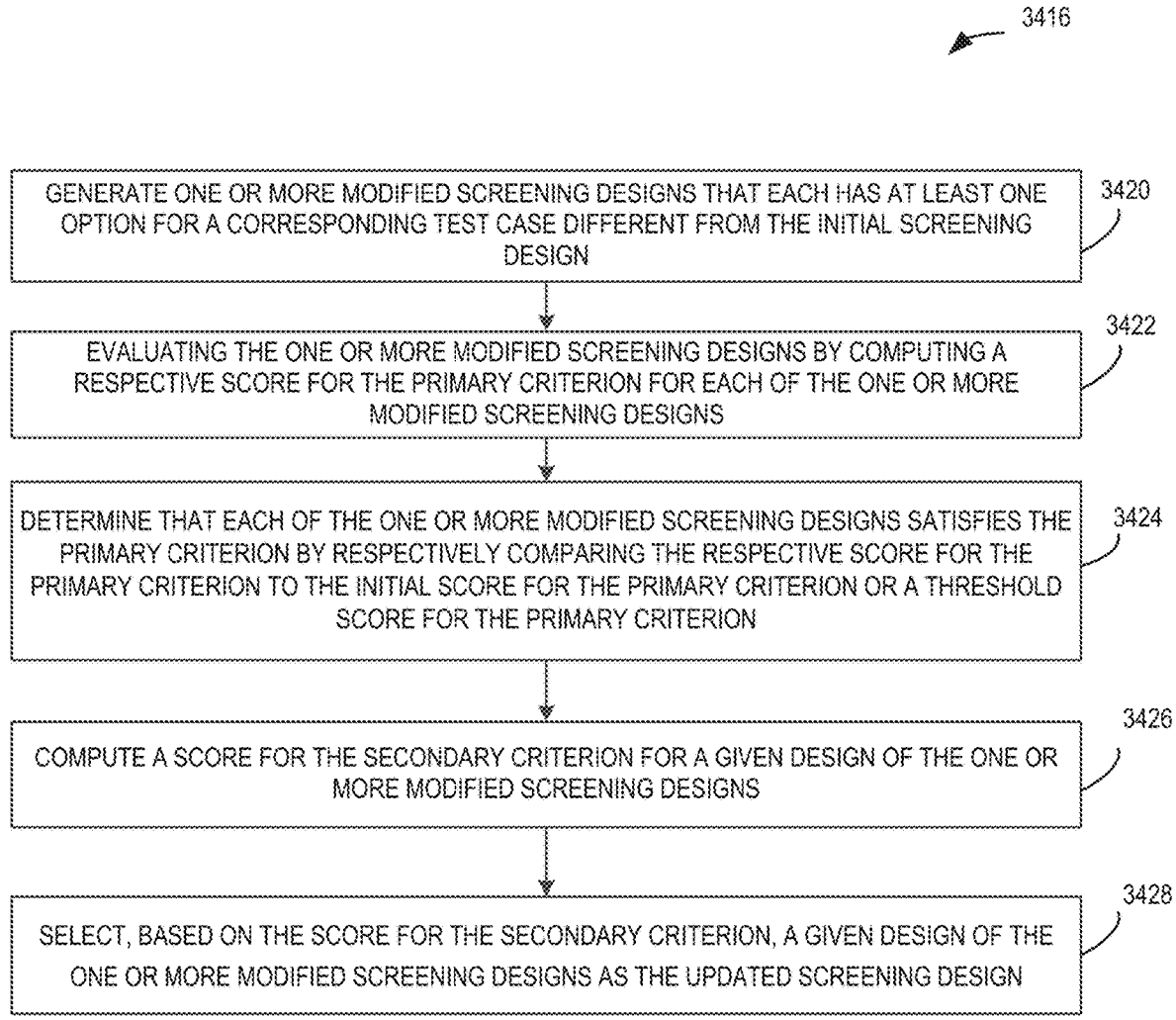

FIGS. 34A and 34B illustrate an example flow diagram for outputting a screening design for an experiment in one or more embodiments.

The method 3400 illustrates an operation 3402 for obtaining a metric N The metric N indicates a quantity of test cases for an output design of an experiment. Test cases is also sometimes referred to in the art as runs in an experiment Each element of a test case of the output design is a test condition for testing one of factors for the experiment A test condition comprises one of different options for a given factor of the experiment. In one or more embodiments, the operation comprises receiving the metric N. For example, a designer of an experiment may be limited in the amount of test cases for the design. The designer can input the metric N or select a default value for metric N, which may be predefined and stored.

The method 3400 illustrates an operation 3404 for obtaining input indicating a quantity p of indicated factors for the output design. Obtaining could comprise receiving a user selection of a total number of factors with a default level of options (e.g., two options for each factor of the design). Additionally or alternatively, receiving includes receiving from a user specific labels for different types of indicated factors. For example, if the design is an experiment for the operation of a computer, the different labels could include software factors (e.g., an internet browser used) or hardware factors (e.g., a RAM speed). The number of received labels indicates a quantity p of indicated factors for the output design.

The method 3400 illustrates an operation 3406 for determining whether there are stored instructions for generating an initial screening design for the experiment (e.g., a construction procedure for a preexisting design or instructions for fetching data of a preexisting design). The initial screening design is for identifying one or more active factors of the experiment each of which independently effect an outcome of a given test case of the experiment.

The preexisting designs, are for example, based on stored instructions for generating designs known to be optimal in some sense for screening designs with the same number of factors p and runs N. For instance, orthogonality is a desirable characteristic of a designed experiment Orthogonal designs provide independent estimates of the active effects, which means that removing an effect from the model will not change the estimates of the other effects. For screening designs with every factor at two-levels, orthogonal designs are G, D, A, and I-optimal. A G-optimal design minimizes the maximum prediction variance for a given model. A D-optimal design minimizes the volume of a confidence ellipsoid about the parameter estimates. An A-optimal design minimizes the average variance of the main effects. An I-optimal design minimizes the average variance of prediction.

In developing screening experiments for two-level factors, regular fractional factorial designs, which are orthogonal and globally D-optimal (i.e. 100% D-efficient), exist if N is a power of two. In addition, non-regular D-optimal orthogonal designs can be generated for almost any N a multiple of four. However, if resource constraints dictate that N is not a multiple of four, an orthogonal design for two-level factors does not exist, although a D-optimal design may still be possible using computer instructions to directly construct an optimal design (e.g., a D-optimal design). For instance, the preexisting design may be one of multiple preexisting designs (e.g., a preexisting design constructed from a Hadamard matrix or a symmetric circulant block matrix). These types of constructions are discussed in more detail with respect to FIG. 40.

In one or more embodiments, one or more known techniques are used to create instructions for fetching data and/or fetching instructions associated with a preexisting design.

The method 3400 illustrates an operation 3408 for, responsive to determining that there are stored instructions for generating the initial screening design for the experiment, selecting, using the stored instructions, the initial screening design for the experiment. For instance, the operation 3408 could comprise selecting, using the obtained given number of test case N and indicated factors p, one or more instructions for constructing or fetching a preexisting design. This can be considered a direct construction method. The direct construction method may be employed responsive to determining there is a preexisting design (e.g., generated from stored instructions or from an electronic library) for directly generating the initial screening design for the experiment that has N test cases for an experiment of p factors (e.g., during operation 3406). In this case, the operation 3408 could comprise selecting, using stored instructions, as the initial screening design a given one of any preexisting designs that have N test cases for an experiment of p factors, responsive to determining there are stored instructions for directly generating the initial screening design for the experiment that has N test cases for an experiment of p factors.

Alternatively, it is possible that there is no known or stored instructions for generating a design for the obtained given number of test case N and indicated factors p, but a preexisting design is selected as a starting place for determining an optimal design or a candidate construction method. One or more embodiments, using the candidate construction method improve computation time over techniques such as coordinate-exchange algorithms when no known technique exists for directly constructing a design of a given number of test case N and indicated factors p.

The candidate construction method may be employed responsive to determining there is not a preexisting design for directly generating the initial screening design for the experiment that has N test cases for an experiment of p factors. In this case, the operation 3408 could comprise selecting, using the preexisting design, as the initial screening design a candidate screening design that does not have N test cases or does not have p factors. The selection of the initial screening design may be responsive to determining there is not a preexisting design for directly generating the initial screening design for the experiment that has N test cases for an experiment of p factors.

In one example of a direct construction method, the selecting of a preexisting design comprises retrieving stored instructions for directly generating, responsive to a given metric indicating a quantity of test cases and a given quantity of factors, one or more candidate initial screening designs. The stored instructions may comprises at least one set of instructions, correlated with both a given metric indicating a quantity of test cases and a given quantity of factors, to directly generate a screening design. Alternatively or additionally, preexisting designs could be stored in the form of an electronic library.

In another example of a candidate construction method, the selecting comprises determining that the initial screening design that satisfies the metric N and the obtained input with factors p cannot be directly generated from stored instructions. The method comprises selecting one or more candidate screening designs that can be directly generated from the stored instructions.

The method 3400 illustrates an operation 3410 for obtaining a primary criterion and a secondary criterion for evaluating the output design, the secondary criterion different from the primary criterion. For instance, a primary criterion could be used to determine how optimal a design is for screening purposes (e.g., an efficiency at identifying one or more active factors each of which independently effect an outcome of a given test case of the experiment). As an example in an experiment for a baking process for an optimal cookie, a factor could be the temperature of an oven. In the experiment, regardless of the ingredients in the cookie, how long the cookie is mixed, etc., at certain temperatures the cookie will burn. Thus, the temperature of the oven could be considered an active factor in an experiment for active factors in a baking process. A screening design that efficiently determines the importance of the temperature factor would be a better design for this experiment.

There could be multiple types of primary criterion. For example, in one or more embodiments, the operation 3410 comprises displaying a graphical user interface indicating one or more options for selecting, from multiple primary criterion, the primary criterion. As explained above there are known computations for evaluating the optimality of a screening design (e.g., Alias-efficiency, D-efficiency, the G-efficiency, the A-efficiency, and the I-efficiency). Each of the multiple primary criterion could indicate one of different efficiency computations (e.g., computations for computing an Alias-efficiency, D-efficiency, G-efficiency, A-efficiency, and I-efficiency). The operation 3410 may include receiving a user selection of the primary criterion of the multiple primary criterion.

However, a designer may have other goals for the experiment which could be classified as one or more secondary criteria. Consideration of secondary criteria is particularly useful when there are multiple possible candidate designs that would satisfy the primary criterion. For instance, in a non-deterministic system, experiment outcomes for a test case could differ, resulting in error between the outcome dictated from an estimated model and the experimental outcome. The designer of the experiment may then be interested in an error rate for the test cases (i.e., test cases that had different results given the same selected options for factors in the design of the experiment). The secondary criterion could then be a secondary criterion for determining an error rate for outcomes of the experiment according to the output design.

In another example, while the primary criterion is related to the main effects or active factors that independently affect an outcome, a designer may also be interested in an interaction between multiple factors. In this case, the secondary criterion could be a secondary criterion for evaluating an effect of an interaction between multiple factors on outcomes of the experiment according to the output design. For instance, the secondary criterion is a secondary criterion related to minimizing a bias on estimates of the main effects due to multi-factor interactions (e.g., aliasing or a correlation for multiple factors). With correlating factors, there is some biasing effect on the outcome of an experiment for one factor given an option selected for another factor. The method may comprise computing respective model matrices where each represents modeled predicted effects on the outcomes of testing according to a given screening design for computations related to minimizing this bias as described in the context of specific examples below.

The method 3400 illustrates an operation 3412 for evaluating the initial screening design by determining an initial score for the primary criterion for the initial screening design. The initial score indicates an efficiency of the initial screening design at identifying the one or more active factors. For instance, in one or more embodiments, the initial score indicates an Alias-efficiency, D-efficiency, a G-efficiency, an A-efficiency, or an I-efficiency for the primary criterion compared to a respective efficiency of an orthogonal design (e.g., a score out of 100).

The method 3400 illustrates an operation 3414 for determining whether to modify the initial screening design based on modification criteria. For instance, a modification could be used to provide a design with the requested test cases described by metric N, and indicated factors p. Therefore, the modification criteria could include one or more of the metric N, and indicated factors p. Additionally or alternatively, a design could already satisfy the requested test cases described by metric N, and indicated factors p (e.g., if it was directly constructed or a candidate design modified to arrive at the requested test cases). In this case, the design can be refined by consideration of one or more secondary criteria for the design of the experiment. In this case the modification criteria comprises one or more of the secondary criteria.

The method 3400 illustrates an operation 3416 for, responsive to determining, based on the modification criteria, to modify the initial screening design, generating an updated screening design for the initial screening design. In some cases (e.g., when an initial screening design is selected that has N test cases for experiment with p factors), the modification criteria could comprises only the secondary criterion. In this case, the updated screening design is a refinement of the design to consider the secondary criterion. In other cases (e.g., when an initial screening design is selected that does not have N test cases for experiment or does not have p factors for the experiment), the modification criteria may comprise the secondary criterion, the metric N, and the indicated factors p. For instance, the modification criteria may be used to update the initial screening design to satisfy the obtained metric N and the indicated factors p. An initial design may already satisfy N or p. In this case, the modification criterion may comprise only one of these factors. In some cases, additionally (e.g., at the same time or separately), modification criteria is used to refine the initial screening design to consider the secondary criterion. One of ordinary skill in the art will appreciate that in embodiments described herein, the secondary criterion could be multiple different secondary criteria different from the primary criterion.

As one example of generating an updated screening design, the method includes modifying an initial screening design by adjusting a given candidate screening design to have an adjusted screening design with N test cases. For instance, the adjusting could comprise generating a test case and adding the test case to the given candidate screening design. This is particular useful when a candidate screening design does not have sufficient test cases. Additionally or alternatively, the adjusting could include selecting a test case from the given candidate screening design and removing the test case from the given candidate screening design. This is particular useful when a candidate screening design has too many test cases. Additionally or alternatively, a modification could include combining multiple candidate screening designs.

As another example of generating an updated screening design, the operation 3416 comprises generating multiple candidate updated screening designs by modifying one or more options of the adjusted screening design. The operation 3416 comprises computing a respective score for the primary criterion for each of the multiple candidate updated screening designs. The operation 3416 comprises selecting one of the candidate updated screening designs as the generated updated screening design based on the respective score. This is particularly useful when there might be multiple designs that satisfy the primary criterion and the secondary criterion.

The method 3400 illustrates an operation 3418 for outputting an indication of the updated screening design for the output design of the experiment. For instance, the method could comprise displaying, via a graphical user interface, an array for the output design. In one type of array, each row of the array represents one of the test cases of the experiment and each column of the array represents one of the factors of the indicated factors. Of course the orientation of the array could be changed to have test cases represented by the columns and factors represented by the rows. Alternatively or additionally, the updated screening design indication could indicate differences or the presence of differences from a preexisting design (e.g., a changed option for a factor or changed score for the design).

One of ordinary skill in the art will appreciate that the method 3400 could be conducted in different orders then shown in method 3400. For instance, the obtained information in operations 3402, 3404, and 3410 could be obtained in any order or simultaneously. Further, multiple operations could be processed in a single operation or a single operation could comprise multiple operations. For instance, FIG. 34B illustrates example operations for operation 3416.

In one or more embodiments, operation 3416 comprises an operation 3420 for generating one or more modified screening designs that each has at least one option for a corresponding test case different from the initial screening design.

For example, in a case where the secondary criterion is a secondary criterion for determining a model-fitting error rate or pure-error for outcomes of the experiment according to the output design, generating one or more modified screening designs that each has at least one option different from the initial screening design could comprise generating a first modified screening design that has more test cases that are assigned the same options for each factor of a respective test case than the initial screening design. In this way there would be increased test cases that have the same options for respective factors, so that the outcome of these test cases can be observed. For example, it may be useful to measure and account for wide variation in responses with runs with the same setting. In another example, where the secondary criterion is a secondary criterion for determining a prediction error rate, it may be useful to instead generate modified screening designs that have greater diversity in test case scenarios to better explore a design space.

In one or more embodiments, operation 3416 comprises one or more operations useful for ensuring that the modified screening designs still satisfies the primary criterion despite changes. For instance, operation 3416 comprises an operation 3422 for evaluating the one or more modified screening designs by computing a respective score for the primary criterion for each of the one or more modified screening designs.

In one or more embodiments, operation 3416 comprises an operation 3424 for determining that each of the one or more modified screening designs satisfies the primary criterion by respectively comparing the respective score for the primary criterion to the initial score for the primary criterion or a threshold score for the primary criterion. This is useful for ensuring that the modified screening designs still satisfy the primary criterion despite changes (either because one or more of the modified screening designs are better than the initial screening design at satisfying the primary criterion or they satisfy, for instance, a predetermined threshold for the primary criterion).

In one or more embodiments, operation 3416 comprises one or more operations for considering a secondary criterion. For instance, operation 3416 comprises an operation 3426 for computing a score for the secondary criterion for a given design of the one or more modified screening designs. In one or more embodiments, operation 3416 comprises an operation 3428 for selecting, based on the score for the secondary criterion, a given design of the one or more modified screening designs as the updated screening design. For instance, a design can be selected that has a maximum score for the secondary criterion. Alternatively, the scores from the primary criterion and secondary criterion could be weighted or averaged to select a design that has a relatively high score for both criterion.

Figure 35A:
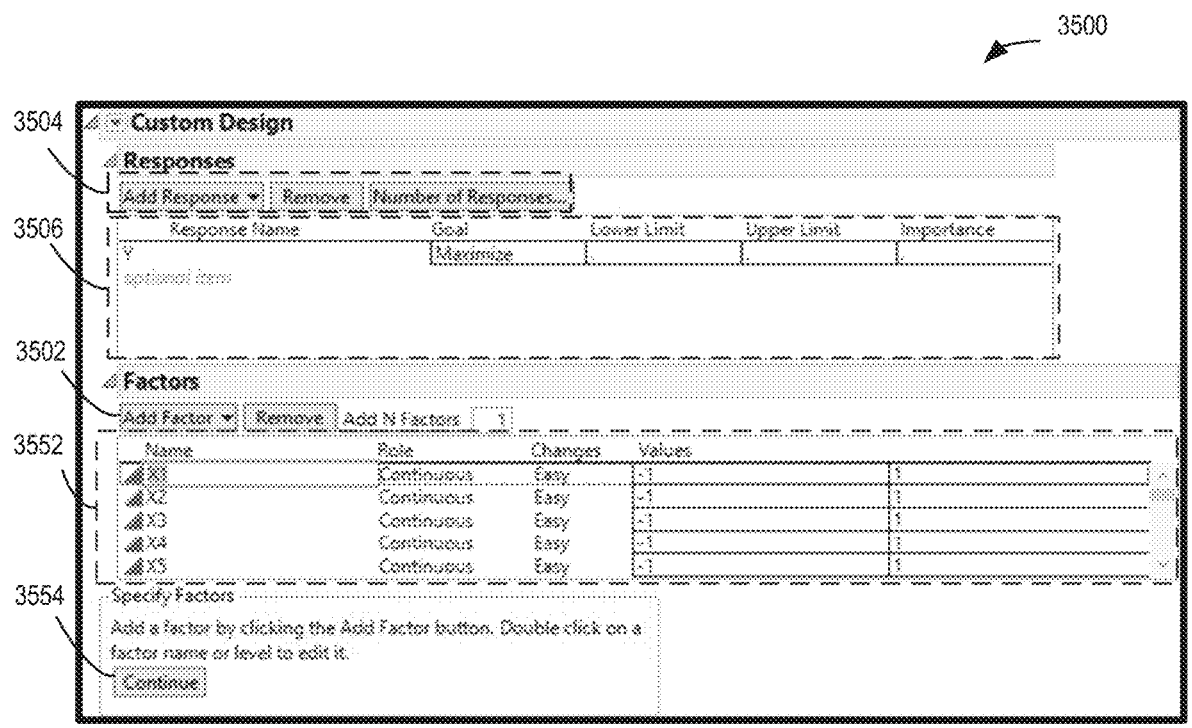
FIGS. 35A and 35B illustrate an example graphical user interface for obtaining factors for an experiment in one or more embodiments.

FIG. 35A illustrate an example graphical user interface 3500 with a dialog window for obtaining factors for an experiment in one or more embodiments.

Figure 35B:
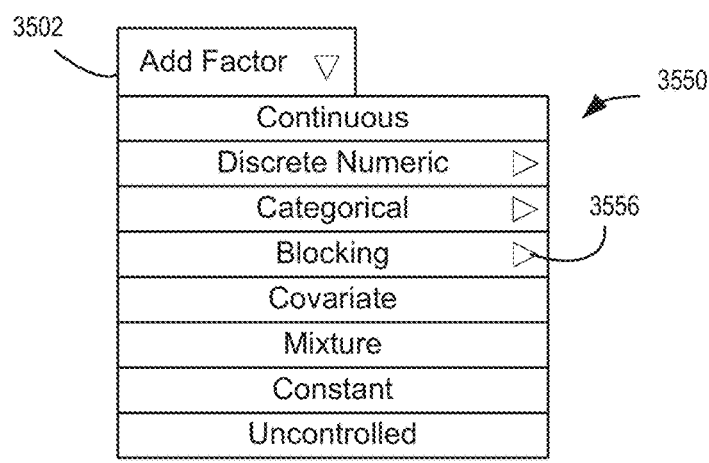

As shown in FIG. 35A, graphical user interface 3500 indicates a user option 3502 for adding factors of different optional types. For instance as shown in FIG. 35B a drop-down menu 3550 may be used to specify one of various types (e.g., continuous, discrete numeric, categorical, blocking, covariate, mixture, constant, and uncontrolled). A user can select in the graphical user interface 3500 a given type of the drop down menu 3550. An indication of type is received for at least one of the indicated factors. The different types shown are merely an example; more or less factor types are possible.

As shown in FIG. 35B, there are possible factor types of a continuous, discrete numeric, and categorical types. A factor of a continuous type indicates that the factor has a range of possible options in the experiment (e.g., within a time period for implementing a test condition). A continuous factor can be set to any value between a lower and upper limit supplied (e.g., set based on the limitations of a process or measurement system). A factor of a discrete numeric type indicates that the factor is continuous in nature, but has set discrete, numeric possible options in the experiment (e.g., 1, 2, or 4 drops of a solution in a chemical experiment). A factor of a categorical type indicates that the factor has set discrete, non-numeric possible options in the experiment (e.g., in an experiment for a computer system the options for an input device factor might be a mouse, track ball or joy stick).

As shown in FIG. 35B, there are also possible factor types of a covariate and blocking type. A covariate factor type indicates the factor affects the experiment outcome but is not controlled like the other factors. Instead, it co-varies with the change in the factor options from one treatment to the next. A blocking factor is a factor type that has an effect on an experimental outcome, but cannot be directly controlled and manipulated by the designer of the experiment in the same way as other factors. In this case, some variables are indicative of a treatment or predictive value by the designer of the experiment of a given factor on outcomes of testing according to the output design of the experiment.

As shown in FIG. 35B, there are also factor types of a mixture, constant and uncontrolled type. A mixture type is a type for a factor that has a relationship with other factors. For example, in a chemical process, a chemical might be composed of two different liquid components. If one factor is related to options for the first liquid component of the chemical and another factor is related to options for the second liquid component of the chemical, indicating the first and second liquid component factors are of a type mixture indicates that together the components must sum to a particular percent of the total mixture. A constant type is a type for a factor that is treated as having a single option. An uncontrolled type is a type for a factor not observed until performing the experiment. This type indicates the options for this factor will be missing in the design of the experiment.

The drop-down menu 3550 could have other drop-down menus to specify other constraints relevant to the factor types (e.g. by clicking an arrow 3556 to display more constraints).

As shown in FIG. 35A, the factors selected could all be of the same type. Alternatively, they could be of different types. FIG. 35A shows an optional window 3552 for selecting a factor to edit the label (e.g. to specify the particular type or options for a factor).

As shown in FIG. 35A, the graphical user interface 3500 may comprise other optional controls or fields for obtaining information relevant to the design of an experiment beyond factors. For instance, a user of the graphical user interface 3500 may want to specify one or more responses for an experiment using optional response controls 3504. As an example, the user may want to have each test case performed more than one time to observe responses or results of the experiment. For instance, the response controls 3504 may comprise the ability to add, remove, or set the number of responses.

Within a given response window 3506, the user of the graphical user interface 3500 may want to set specific goals for an outcome of the experiment (or response) or the importance of that response. For instance, the user may specify for a given response a goal of maximize, match target, minimize, or none. A goal of maximize indicates that the best value is the largest possible. If there are natural lower or upper bounds, these can be specified using the lower limit or upper limit fields of response window 3506. A goal of minimize indicates that the best value is the smallest possible. If there are natural lower or upper bounds, these can be specified using the lower limit or upper limit fields of response window 3506. A goal of match target indicates that the best value is a specific target value. This can be explicitly indicated or can be assumed to be midway between the lower limit and upper limit fields of response window 3506.

The importance field of response window 3506 allows responses to be weighted (e.g., based on the importance of a goal for that response) when there are multiple responses.

The graphical user interface 3500 may have an indication (e.g., continue button 3554) for indicating that the user has specified the response and factors.

Figure 36:
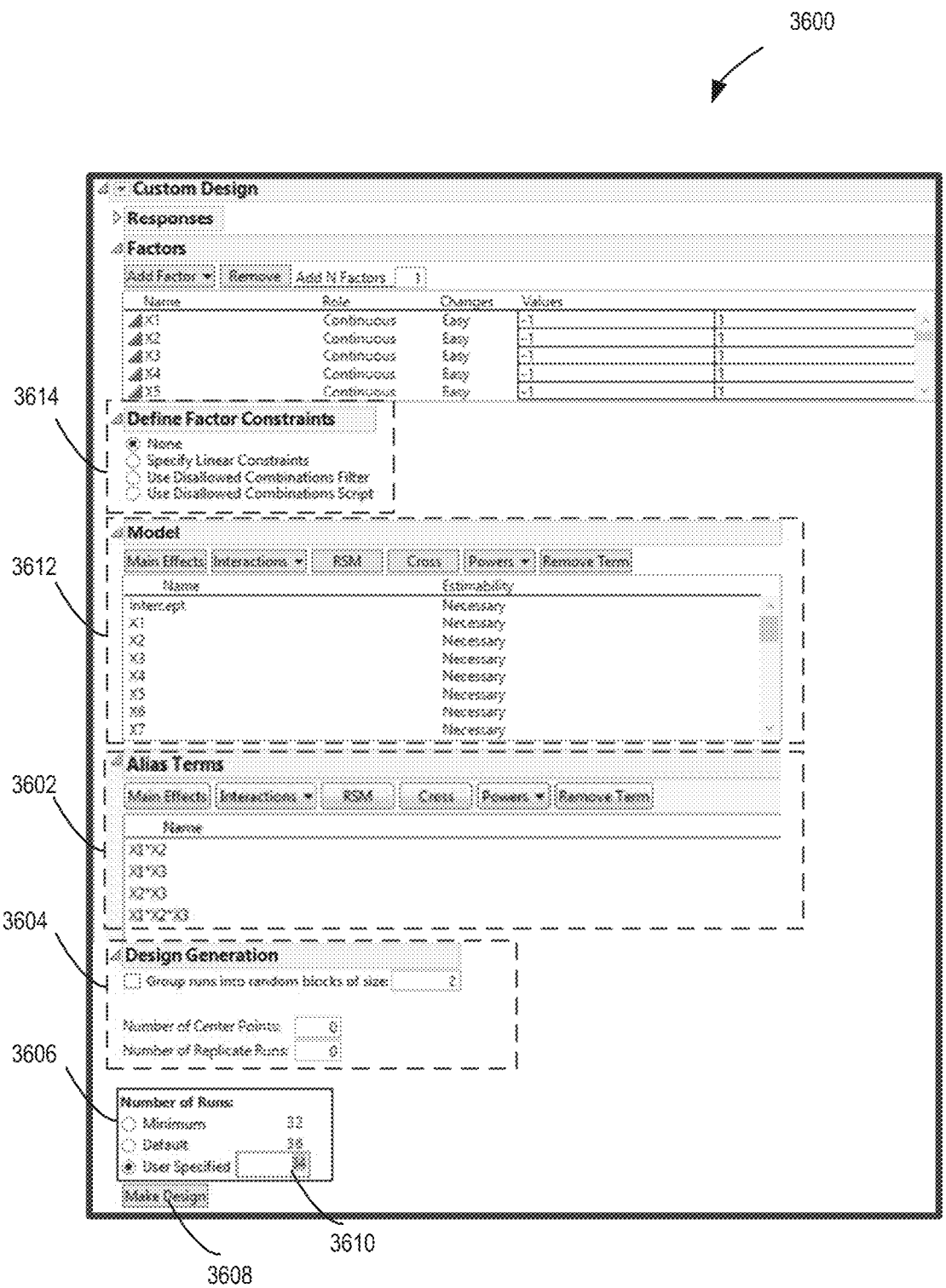
FIG. 36 illustrates an example graphical user interface for obtaining a metric indicating a quantity of test cases of an experiment in one or more embodiments.

FIG. 36 illustrates an example graphical user interface 3600 for obtaining a metric N indicating a quantity of test cases of an experiment in one or more embodiments. The graphical user interface 3600 may have different windows or controls for specifying constraints on the factors, the terms and type of assumed model using to describe the process or experiment being investigated, and the number of experimental runs as well as any additional runs or constraints on those runs.

In particular, as shown in number of runs window 3606, graphical user interface 3600 may optionally allow a user to select a minimum level of runs and/or a default level of runs. A minimum level of runs may allow more additional runs (e.g., to satisfy secondary criteria). The values for the minimum level of runs or defaults may be static values or variable based on, for instance, the number of factors of the experiment. Additionally or alternatively, the runs window 3606 allows a user to specify a particular number for the runs (e.g., in a run field 3610). Embodiments herein are useful even if the user selects a number of runs in which there are no preexisting designs that could satisfy the requested design (e.g., there are no stored instructions for generating a preexisting design).

Additional constraints for the design may be input. For example in an optional design generation window 3604, a user may select options to group runs, to set center points or replicate runs. For instance, a center point is useful to set a run such that for each continuous factor of the run, the value of a continuous factor of the run is set midway between the high and low settings. In an optional alias term window 3602, the user may enter alias or correlation properties between factors (e.g., a two-way or three-way interaction between specified factors).

In an optional model window 3612 the user can select constraints on the model. In an optional factor constraints window 3614, the user can select factor constraints. For instance, the user may wish to restrict values for individual factors using a disallowed combinations filter.

Once the user is satisfied with their inputs, the user can select a control to generate a design (e.g., by selecting the Make Design button 3608) and start the process of creating the optimal design that maximizes one or more criteria (e.g., a specified efficiency measure) under the constraints provided by the user (in this case, a specified number of runs in run field 3610).

Figure 37:
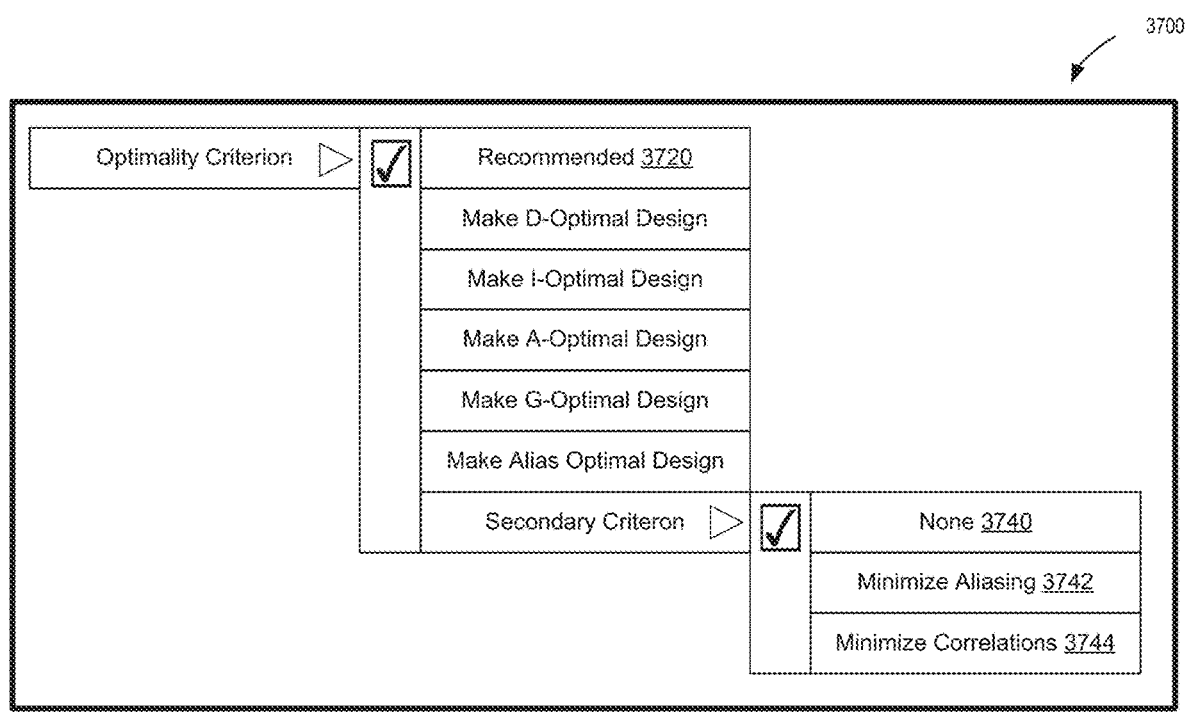
FIG. 37 illustrates an example graphical user interface for obtaining a primary criterion and a secondary criterion in one or more embodiments.

FIG. 37 illustrates an example graphical user interface 3700 for obtaining a primary criterion and a secondary criterion in one or more embodiments. The graphical user interface 3700 gives as an example different options for user selection of a primary criterion for evaluating a design of the experiment as optimal (e.g., an optimal screening design). The user may also be able to set more than one primary criterion (e.g., by selecting one or more of the optimality criterion). The graphical user interface 3700 also gives an option to select a recommended option 3720. The recommended option 3720 may be set to one of the options or may be some weighting between different available options (e.g., a design that satisfies all or certain ones of the criteria).

The user can also optionally set a secondary criterion (e.g., a criterion related to interactions between factors). In the example shown in FIG. 37, the secondary criterion include a minimize aliasing option 3742 and minimize correlations option 3744. With aliased terms, it is indistinguishable which or both of the terms is having an effect on an outcome of an experiment A sample example is shown below in Table 1 for 3 factors with possible different options denoted 1 and 0 in different test cases. The interaction of factors $X_1$ and $X_2$ ($X_{12}$) gives the same options as factor $X_3$. Therefore, factor $X_3$ and interaction factor $X_{12}$ are considered aliased because it is unknown whether factor $X_3$ or interaction factor $X_{12}$ are an active factor in the outcome. With correlation, there is some ability to distinguish between terms, but how well the terms can be distinguished depends on the level of correlation. A lower correlation corresponds to a better ability to distinguish.

TABLE 1

| Factors | $X_1$ | $X_2$ | $X_3$ | $X_{12}$ |
| --- | --- | --- | --- | --- |
| Test Case 1 | 1 | 1 | 1 | 1 |
| Test Case 2 | 1 | 0 | 0 | 0 |

TABLE 1-continued

| Factors | $X_1$ | $X_2$ | $X_3$ | $X_{12}$ |
|---|---|---|---|---|
| Test Case 3 | 0 | 1 | 0 | 0 |
| Test Case 4 | 0 | 0 | 1 | 1 |

Selecting the minimize aliasing option 3742 versus selecting minimize correlations option 3744 can allow a designer control over selection between different possible design options. For example, a first design could have a large number of factors uncorrelated with one another at the cost of a few factors being aliased. A second design could have some level of correlation among all the factors. If the minimize correlations option 3744 is selected, the first design may be selected as having the lowest overall correlations. However, this results in a few factors aliased and so not estimable. If instead the minimize aliasing option 3742 is selected, the second design may be selected as having the lowest aliasing. This might be desirable to spread the correlation around so that every factor has some ability to be estimated.

Selecting the None option 3740 in the graphical user interface 3700 as shown in FIG. 37, means the system will directly construct the optimal design and not spend any additional processing time optimizing a secondary criterion. If the Minimize Aliasing option 3742 is instead chosen, and there are multiple designs that attain the optimal form (either different construction methods, or if only a subset of factors are needed), an aliasing matrix is minimized. That is, denoting $X_1$ to be the model matrix for the main effects model, and $X_2$ the model matrix for the two-factor interactions, then to minimize the bias on the estimates of the main effects due to two-factor interactions, a computer algorithm picks a subset of columns or designs that minimizes trace (A' A), where:

$$A = (X_1^T X_1)^{-1} X_1^T X_2.$$

If the minimize correlations option 3744 is chosen, a subset of columns or designs is chosen to minimize the average of the absolute entries of $X_1^T X_1$, to minimize the correlations between the main effects model terms.

Another possible criterion not shown in FIG. 37 are possible to allow a designer greater control over the output design. For example an option may be provided to maximize the estimation capacity which relates to the ability to estimate the interactions from subsets of factors. Alternatively, a user option might seek a generalized minimum aberration design that can help minimize the contamination of non-negligible interactions on the estimates of the main effects. Another example could be used to examine if it is possible to have an optimal design that also has some replicated runs for the estimation of pure error. Other secondary criteria not shown in FIG. 37 are possible as described herein.

FIG. 38 illustrates an example initial screening design 3801 and modified screening designs 3802 and 3803 in one or more embodiments. It is possible that there are multiple candidate initial screening designs correlated with N respective test cases each with p factors. In one or more embodiments, one or more of the multiple candidate initial screening designs is selected by determining a maximum of respective computed scores for the primary criterion for each of the multiple candidate initial screening designs. Alternatively, one or more of multiple candidate initial screening designs is selected by comparing a primary criterion for each of the multiple candidate initial screening designs to a threshold score for the primary criterion.

In the example shown in FIG. 38, the initial screening design 3801 associated or otherwise represented by a matrix of options for factors minimizes the average correlation among the main effects with minimal confounding among the aliased terms. A possible modified candidate initial screening design 3803 improves a primary criterion for the initial screening design 3801 (e.g., by minimizing predictive uncertainty and improving an A-optimal computation), but at the cost of a secondary criterion by having more confounding among aliased terms. A possible modified candidate initial screening design 3802 minimizes the average correlation between the main effects and aliased terms with minimal confounding among the aliased terms. It is selected as the updated screening design or as an intermediate design to an updated screening design because it is still considered an optimal screening design based on a primary criterion and improves a secondary criterion related to aliased terms unlike possible modified candidate initial screening design 3803.

Figure 39:
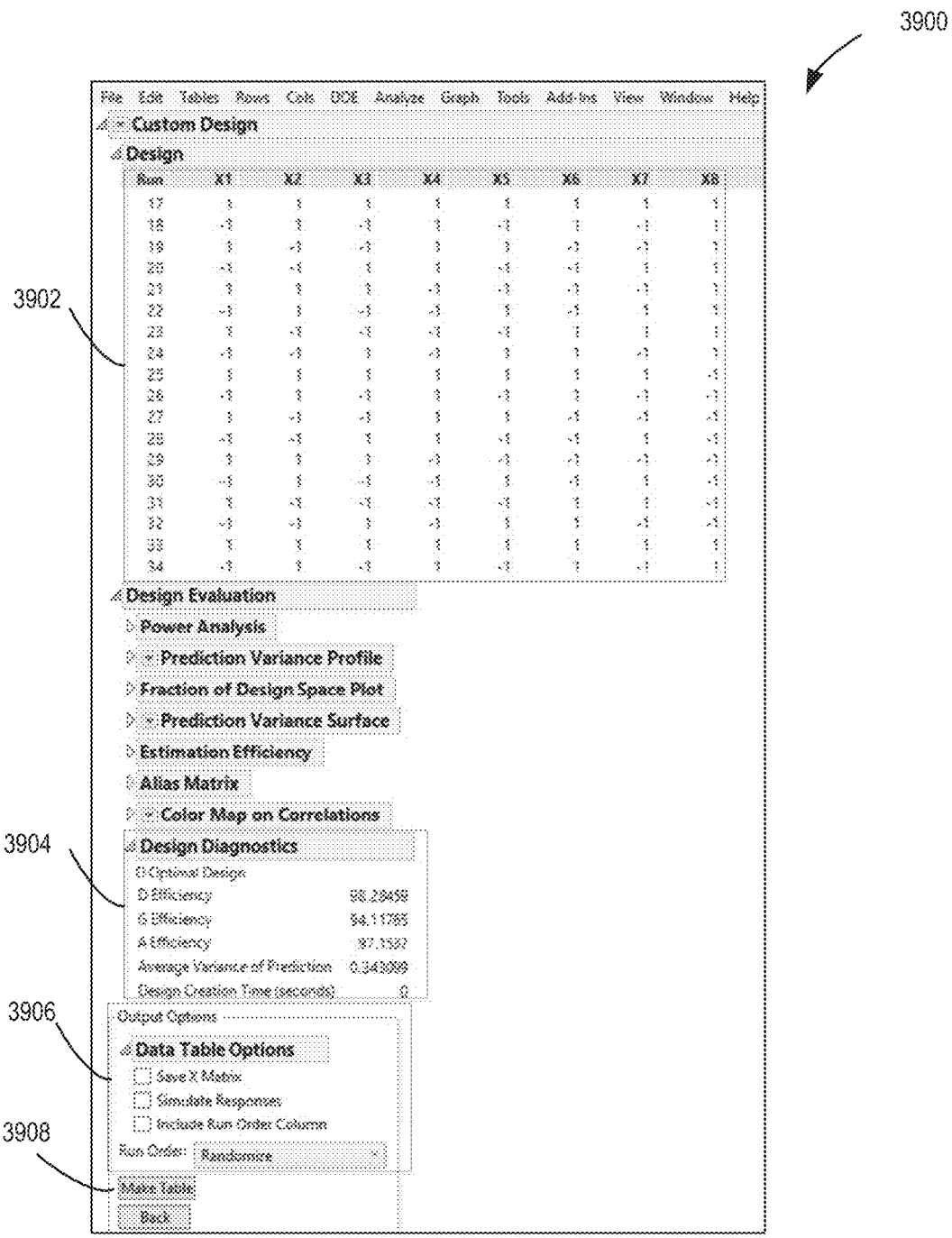
FIG. 39 illustrates an example graphical user interface for outputting an indication of a screening design in one or more embodiments.

FIG. 39 illustrates an example graphical user interface for outputting an indication of a screening design in one or more embodiments. In one or more embodiments, once a design has been constructed as described herein, a window appears in a graphical user interface 3900 showing the resulting design 3902. Here test runs 17-34 are shown as an array representation for an experiment with 8 factors (X1-X8) and 34 runs. Each row specifies one of two different options for the factors for a test case. A scroll may be provided to show the entire design. Alternatively other controls may be provided to export a table of the generated options (e.g., make table button 3908). In this example, output option controls 3906 is provided for further manipulation or use of the design (e.g., to simulate responses, include run order column, randomize run order, etc.)

In this example, several diagnostics 3904 are provided to the user for evaluating the design. The designation "D Optimal Design" indicates that the design was constructed to maximize the D Efficiency measure (100 is best). Alternative efficiency measures are also provided for convenience (100 is best for each). In addition to the efficiency measures, the average variance of prediction is provided which is a measure of uncertainty in predicted responses based on a model estimated from the design. It is better to have a lower average variance of prediction. The design creation time is also provided. It is better to have a lower design creation time.

Figure 40:
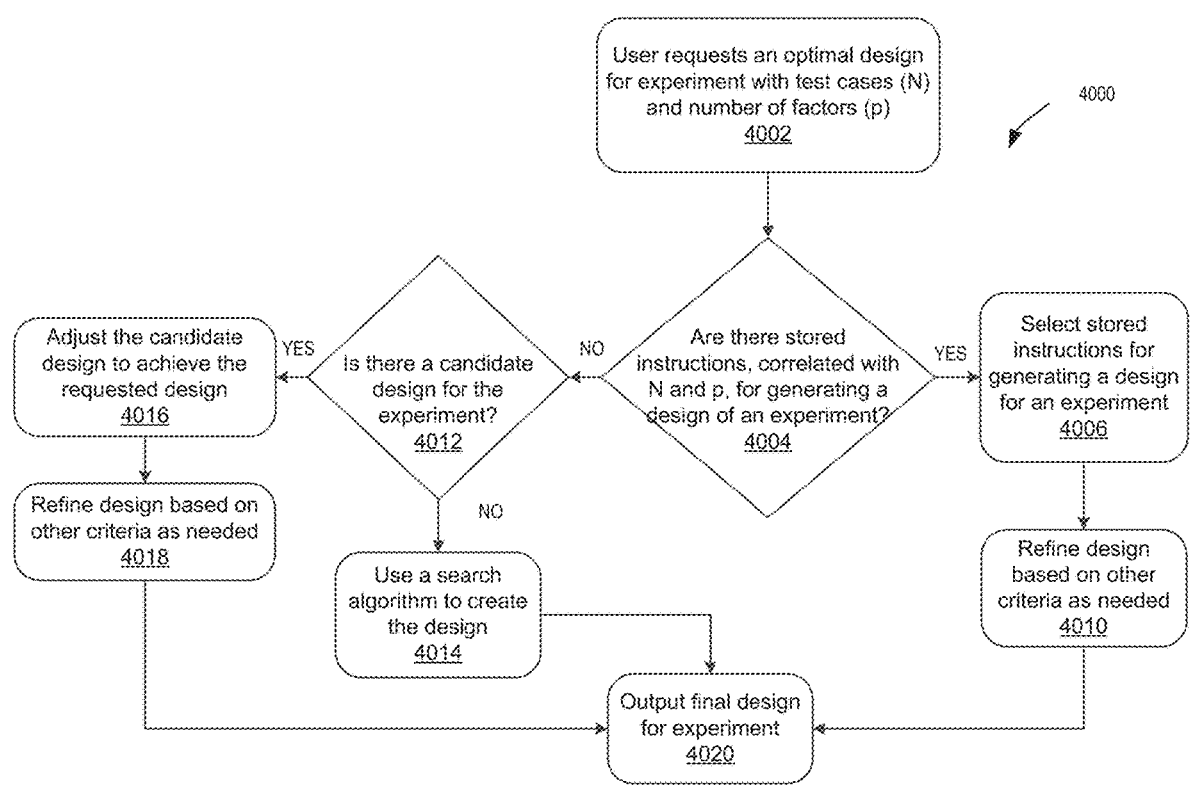
FIG. 40 illustrates an example flow diagram for outputting a screening design for an experiment in one or more embodiments.

FIG. 40 illustrates an example flow diagram 4000 for outputting a outputting a screening design for an experiment in one or more embodiments.

In a first operation 4002, the user requests an optimal design for an experiment with test cases of a quantity N and factors for each test case of a quantity p. For instance, the request can be made via a graphical user interface to input or select defaults for N and p and other information relevant to the design. If the user proceeds to make a design, the method determines in an operation 4004 whether there are stored instructions, correlated with N and p, for generating a design of an experiment. In other words, once the input has been provided, the initial inquiry is to determine whether the design can be directly constructed using known methods (e.g., in preexisting designs). If so, then it remains to determine what method to use for the given inputs in an operation 4006.

If the user input does not match any known case where a design can be directly constructed, rather than start from scratch (e.g., using a search algorithm), it may be more beneficial to use a known direct construction method to build a candidate starting design from which to generate the optimal design through additions to or manipulations of that candidate starting design, and the method proceeds to an operation 4012.

For instance, there are known design catalogs, which can be used as preexisting designs for direct construction, especially for designs not generated using one of general construction procedures below. For example, a table of D-optimal design matrices can be found at this website: http://www.indiana.edu/~maxdet/fullPage.shtml#tableTop.

There are certain known methods, which can be used to create preexisting designs for constructing D-optimal designs for different numbers of runs in some of the following cases:

N is a multiple of 4 (or N≡0 mod 4). This is the case where orthogonal designs are
D-optimal.

N is odd and one more than a multiple of 4 (or N≡1 mod 4)

N is even, but not a multiple of 4 (or N≡2 mod 4); and

N is odd and three more than a multiple of 4 (or N≡3 mod 4)

In the case of N≡0 mod 4, a D-optimal design for two level factors may be constructed by generating a Hadamard matrix. There are multiple different construction methods sufficient for generating all the Hadamard matrices up to and including N=300 for Hadamard matrices, N=p. When N>p, any subset of the columns of the Hadamard matrix of order N excluding the first column for the intercept yields an orthogonal (and globally D-optimal) design. For example, one example construction methods for Hadamard matrices is the Sylvester construction method discussed in more detail below as an example.

For the case of N≡1 mod 4, if a Hadamard matrix of order N−1 exists, only the case where N=p requires additional effort for construction. For N>p construction starts by generating a Hadamard matrix of order N−1 and adding a row of ones for simplicity. Again, any subset of columns can be removed to obtain a design with the desired number of factors.

For the case of N≡2 mod 4, for N−1>p, construction starts by generating a Hadamard matrix of order N−2 and adding two orthogonal rows (or near orthogonal if p is odd). For the case N=p, a general construction procedure can use block circulant matrices. The case of N−1=p can easily be derived from a design with N=p by deleting any row.

The case of N≡3 mod 4, is the most computationally difficult except when p(N+5)/2. For these values of p, construction starts with generating a Hadamard matrix with N+1 rows and columns. Then, removing the first row and choosing an appropriate subset of columns yields the globally D-optimal design. When p>(N+5)/2 constructions are known for special cases.

Since many of the cases are derived from a Hadamard matrix this is discussed in more detail below. Assuming the standard linear model Y=Xβ+ε, where X represents an N×p design matrix consisting of N runs with each run associated with a combination of levels in p−1 factors (p unknown parameters, including an intercept), Y represents the vector of responses that will be collected during the experiment, β represents the vector of unknown parameters to be estimated from the experimental data, and E represents the vector of errors between the collected responses and the assumed true underlying mean model Xβ. Technically, X is associated with a particular design D and so is often depicted as X(D), but for the sake of simplifying notation, superscripts and subscripts are used instead to specify a specific design matrix.

The focus here is on generating optimal designs, which give layouts of factor levels per run that optimize a specified criterion of interest for a given total number of runs. Often, this criteria, is related to the information matrix of the design, which is computed as M=X'X, where X' is the transpose of X. Considered as designs with two-level factors and assuming that the two levels have been coded −1 and 1 for each factor.

There are a wide variety of optimal design criteria. D-optimality is given as an example since it is the most commonly used criterion in practice. A design is D-optimal if it maximizes the determinant of M or, equivalently, minimizes the determinant of $M^{-1}$. Maximizing the determinant of M minimizes the volume of the confidence region around the estimates of β for a fixed confidence level. For example, for a simple linear model (β={$\beta_0,\beta_1$}'), this would be equivalent to minimizing the 2-dimensional confidence region around {$\hat{\beta}_0,\hat{\beta}_1$}. Thus, D-optimal designs minimize an omnibus measure of the uncertainty about the parameter estimates. Embodiments described herein are applicable for other optimality criteria.

As an example, of generating an initial starting design from known methods, the case where N≡0 mod 4 is discussed. The optimal form of M for this case is $$M_0^* = \begin{bmatrix} N & 0 & 0 & \ldots & 0 \\ 0 & N & 0 & \ldots & 0 \\ 0 & 0 & N & \ldots & 0 \\ \vdots & \vdots & \vdots & \ddots & \vdots \\ 0 & 0 & 0 & \ldots & N \end{bmatrix}$$

Its determinant is $$\det(M_0^*) = N^p.$$

The design matrix $X_0^*$ that achieves this form is a member of the Hadamard class of matrices, often simply referred to as Hadamard matrices. Typically, these matrices must be standardized so that the first column is all 1's (corresponding to the intercept term). The name of this class of matrices acknowledges the work of Jacques Hadamard. See e.g., Hadamard, J. (1893). Resolution d'une question relative aux determinants. *Bulletin des Sciences Mathematiques* 17, 240-246. This work proved that the determinant of $X_0^*$ is the largest determinant among all matrices with binary (−1 or 1) entries and so, as a corollary, showed that $M_0^*$ has the largest determinant among all M matrices created from binary matrices.

One application of construction of a design using a Hadamard matrices is the Sylvester Construction, with a construction:

1. Define $H_1 = [1]$

2. $H_{2^k} = \begin{bmatrix} H_{2^{k-1}} & H_{2^{k-1}} \\ H_{2^{k-1}} & -H_{2^{k-1}} \end{bmatrix}$ for $k = 1, 2, \ldots$

Example $H_1 = [1]$ $$H_2 = \begin{bmatrix} [r]1 & 1 \\ 1 & -1 \end{bmatrix}$$

$$H_4 = \begin{bmatrix} [r]1 & 1 & 1 & 1 \\ 1 & -1 & 1 & -1 \\ 1 & 1 & -1 & -1 \\ 1 & -1 & -1 & 1 \end{bmatrix}$$

The Sylvester construction can generate Hadamard matrices with run sizes that are powers of 2. Another example construction method is the Williamson construction for Hadamard matrices. Let $$W = \begin{bmatrix} A & B & C & D \\ -B & A & -D & C \\ -C & D & A & -B \\ -D & -C & B & A \end{bmatrix},$$

where A, B, C, and D are symmetric, circulant matrices of order n with entries ±1 that satisfy $XY' = YX'$, for $X \neq Y \in \{A,B,C,D\}$ as well as $AA' + BB' + CC' + DD' = 4nI_n$ If these conditions are satisfied, then W is a Hadamard matrix of order 4n.

Circulant Matrices are Matrices of the Form $$P = \begin{bmatrix} p_1 & p_2 & p_3 & \cdots & p_N \\ p_N & p_1 & p_2 & \cdots & p_{N-1} \\ p_{N-1} & p_N & p_1 & \cdots & p_{N-2} \\ \vdots & \vdots & \vdots & \ddots & \vdots \\ p_2 & p_3 & p_4 & \cdots & p_1 \end{bmatrix}.$$

so they can be specified by their first row. The Williamson construction requires that the circulant matrices have the additional property of being symmetric.

The matrices A, B, C, and D are often referred to as Williamson-type "plug-in" matrices. Notice that when $A=B=C=D=[1]$ then $W=H_4$. As an example, let:

$$A = \begin{bmatrix} 1 & 1 & 1 \\ 1 & 1 & 1 \\ 1 & 1 & 1 \end{bmatrix}, \text{ and } B = C = D = \begin{bmatrix} 1 & -1 & -1 \\ -1 & 1 & -1 \\ -1 & -1 & 1 \end{bmatrix}.$$

Note that A, B, C, and D are ±1 square matrices of order 3 and since $$AA' = \begin{bmatrix} 3 & 3 & 3 \\ 3 & 3 & 3 \\ 3 & 3 & 3 \end{bmatrix}, \text{ and } BB' = CC' = DD' = \begin{bmatrix} 3 & -1 & -1 \\ -1 & 3 & -1 \\ -1 & -1 & 3 \end{bmatrix}.$$

They also satisfy $AA' + BB' + CC' + DD' = 12I_3$. Furthermore, since $$AB' = \begin{bmatrix} -1 & -1 & -1 \\ -1 & -1 & -1 \\ -1 & -1 & -1 \\ -1 & -1 & -1 \end{bmatrix} = BA' \text{ and } B = C = D,$$

it follows that $AB' = BA'; AC' = CA'; AD' = DA'; BC' = CB'; BD' = DB'; CD' = DC'.$ Since the required conditions are satisfied, we can use A, B, C, and D to construct $H_{12}$ as follows:

$$H_{12} = \begin{bmatrix} 1 & 1 & 1 & 1 & -1 & -1 & 1 & -1 & -1 & 1 & -1 & -1 \\ 1 & 1 & 1 & -1 & 1 & -1 & -1 & 1 & -1 & -1 & 1 & -1 \\ 1 & 1 & 1 & -1 & -1 & 1 & -1 & -1 & 1 & -1 & -1 & 1 \\ -1 & 1 & 1 & 1 & 1 & 1 & -1 & 1 & 1 & 1 & -1 & -1 \\ 1 & -1 & 1 & 1 & 1 & 1 & 1 & -1 & 1 & -1 & 1 & -1 \\ 1 & 1 & -1 & 1 & 1 & 1 & 1 & 1 & -1 & -1 & -1 & 1 \\ -1 & 1 & 1 & 1 & -1 & -1 & 1 & 1 & 1 & -1 & 1 & 1 \\ 1 & -1 & 1 & -1 & 1 & -1 & 1 & 1 & 1 & 1 & -1 & 1 \\ 1 & 1 & -1 & -1 & -1 & 1 & 1 & 1 & 1 & 1 & 1 & -1 \\ -1 & 1 & 1 & -1 & 1 & 1 & 1 & -1 & -1 & 1 & 1 & 1 \\ 1 & -1 & 1 & 1 & -1 & 1 & -1 & 1 & -1 & 1 & 1 & 1 \\ 1 & 1 & -1 & 1 & 1 & -1 & -1 & -1 & 1 & 1 & 1 & 1 \end{bmatrix}$$

Other preexisting designs can be defined by other construction methods not specifically described herein (e.g., other preexisting designs constructed from a Hadamard matrix or a circulant block matrix).

Operation 4006 specifies to select stored instructions for generating a design for an experiment. Any which of these construction methods could be used to specify or derive stored instructions for generating a design. However, previously these type of construction methods solely focused on generating a design that maximizes a particular measure of efficiency. That is, once a design is generated, the task is complete; there is no further consideration of additional properties of the design. This often results in undefined or incomplete steps within the construction method (e.g. add an additional run with any combination of factor level inputs). These past approaches did not contemplate refining the design for any sort of secondary criteria. In some cases, there are multiple designs that maximize a particular efficiency, and so these designs are simply catalogued with no other consideration for any further distinctions among them.

Statisticians are interested in other criteria to evaluate a design beyond a measure of efficiency. There are multiple other secondary criteria that can be considered as well. In an operation 4010, these other criteria can be considered by refining the design based on other criteria as needed. For example, if a construction method simply requires adding an additional experimental run to a known design with no specification as to what that run should look, the default might be to make the new run be different from all the other runs before it, resulting in a design that more completely explores the space of possible factor inputs into the process being investigated (e.g., to consider a prediction error rate). A user could optionally select the new run be a repeat of a previous run, which would result in a design that better estimates "pure error" (pure uncertainty within the process untainted by uncertainty introduced in varying factor inputs), which could help yield better estimates of the factor effects. One or more embodiments, improve existing direct construction methods by providing default settings and/or user options representing statistical principles that goes above and beyond the construction methods.

In the case of multiple designs that satisfy an optimal criteria, user options could provide ways to investigate secondary properties of these designs to determine which may be best suited as a default for users. For example, one design might have better predictive properties than another design (reduced uncertainty in predicted responses), but at the cost of making some effects explicitly present in the assumed underlying model completely indistinguishable from effects that, while not explicitly in the assumed model, may actually be present in the true underlying model (this is referred to as "confounding" or "aliasing"). In this case, the user may choose to go with an alternative design based on the default assumption that confounding of effects is much less desirable, while also building in user options to choose the original design should predictive properties be of greater interest. As described with respect to FIG. 37 these secondary criteria can be selected by providing user options. Operation 4020 concludes with outputting a final design for the experiment after refinement.

In the case where there were not stored instructions for generating a design of an experiment to satisfy N and p, the flow diagram 4000 proceeds with an operation 4012 to consider whether there are candidate designs for the experiment. If there are candidate designs, an operation 4016 provides for adjusting the candidate design to achieve the request described (e.g., by methods described herein, such as adding or removing a test case from a candidate design or combining candidate designs). The choice of a starting design may impact the quality of the design further refined using coordinate-exchange. For example, in the case of N≡3 mod 4, where there is less availability in constructions guaranteeing optimality, one can quickly generate a reasonable starting design for p (N+5)/2. Similarly, for the saturated cases where a direct construction is not known, one can start by generating a design having the maximal number of columns for the unsaturated case. Then a highly D-efficient design can be obtained by adding columns using some algorithmic optimization approach.

One such algorithmic approach related to adding one or more additional columns, involves adding one element at a time to a column, and choosing the value that maximizes $\det(X_1^T X_1)$, or adding random column(s), and using coordinate exchange on that column(s) only, rather than having to iterate over the whole design. This approach improves computational processing over approaches that use coordinate exchange across a whole design from a random starting point. In an operation 4018, the design can be refined based on other criteria described herein.

If there is not a candidate design, an operation 4014 a search algorithm is used to create the design. A search algorithm is the approach taken in other statistical software to generate a design (e.g., one or more software tools offered by SAS Institute Inc. of Cary, N.C., USA such as WPC)). Once the user provided input, a candidate design would be generated at random and then an algorithm would be used to refine the entries of this design to maximize a user-selected measure of the design's efficiency (how well the design minimizes a measure of uncertainty regarding estimates of the factor effects on the response). The user can specify how many random designs to start with. The more starts, the more likely the best design will be found, but at a cost of more computation time.

In one or more embodiments described herein, a search algorithm is now implemented as a last resort for those cases where a design cannot be directly constructed, or a constructible/known design does not exist.

Here, the improvement in design diagnostics brought about by the new flow diagram 4000 are clearly displayed in Tables 2 and 3. Table 2 shows design diagnostics for existing commercially available JMP® version 14. Table 3 shows improvement in design diagnostic using methods described herein.

TABLE 2

| Example | Runs | Factors | D-Efficiency | G-Efficiency | A-Efficiency | Avg Variance of Prediction | Time (sec) |
|---|---|---|---|---|---|---|---|
| 1 | 32 | 31 | 92.61564 | 53.94075 | 85.46805 | 0.413325 | 22.83333 |
| 2 | 33 | 31 | 94.21147 | 61.08052 | 88.52126 | 0.387371 | 16.38333 |
| 3 | 34 | 31 | 94.43427 | 67.74718 | 89.05693 | 0.373821 | 21.71667 |
| 4 | 1059 | 531 | 98.50556 | 96.54483 | 97.02068 | 0.173249 | 206.7833 |

TABLE 3

| Example | Runs | Factors | D-Efficiency | G-Efficiency | A-Efficiency | Avg Variance of Prediction | Time (sec) |
|---|---|---|---|---|---|---|---|
| 1 | 32 | 31 | 100 | 100 | 100 | 0.354167 | 0.18333 |
| 2 | 33 | 31 | 99.09306 | 97.15946 | 98.5089 | 0.348633 | 0 |
| 3 | 34 | 31 | 98.28459 | 94.11765 | 97.1537 | 0.343099 | 0 |
| 4 | 1059 | 531 | 99.96339 | 97.40897 | 99.90521 | 0.168243 | 2.65 |

As shown in Table 3 compared to Table 2, the design time is significantly reduced to nearly instantaneous in some cases. (The true time is not 0; rather, it is simply so small that it has dropped below the display threshold). The time savings are particularly significant in situations such as Example 4 where the number of runs and factors is large (1059 runs and 531 factors). In all of the examples, having stored instructions for generating an initial screening design improved processing time. In Example 1 (32 runs), a Hadamard matrix was used as an initial screening design because the number of runs was a multiple of 4. In Example 2 (33 runs), a Hadamard matrix was used as the initial screening design, and the initial screening design was modified to add a run to the Hadamard matrix to achieve a design with 33 runs. In Example 3 (34 runs), a Hadamard matrix was used as the initial screening design, and the initial screening design was modified to add two orthogonal runs to the Hadamard matrix. In Example 4 (1059 runs and 531 factors), a Hadamard matrix with 1060 rows was used as the initial screening design, and the initial screening design was modified to remove a row of the Hadamard matrix and reduce to 531 columns.

Further, the optimization is improved in each of the examples. It should be noted here that the D Efficiency displayed in Table 3 for Example 3 (34 runs and 31 factors) is the highest efficiency that can be achieved for this number of runs and number of factors. Accordingly, embodiments herein are useful for reducing design time while improving measures of optimization. Further, embodiments herein are useful for optimizing designs to consider secondary criteria beyond an optimization criteria.

What is claimed is:

1. A computer-program product tangibly embodied in a non-transitory machine-readable storage medium, the computer-program product including instructions operable to cause a computing device to:
  obtain a metric N indicating a quantity of a plurality of test cases for an output design of an experiment, wherein each element of a test case of the output design is a test condition for testing one of factors for the experiment, and wherein a test condition comprises one of different options for a given factor of the experiment;
  obtain input indicating a quantity p of an indicated plurality of factors for the output design;
  determine whether there are stored instructions for generating an initial screening design for the experiment, the initial screening design for identifying one or more active factors of the experiment each of which independently affect an outcome of a given test case of the experiment;
  responsive to determining that there are stored instructions for generating the initial screening design for the experiment, select, using the stored instructions, the initial screening design for the experiment;
  obtain a primary criterion and a secondary criterion for scoring the output design, the secondary criterion different from the primary criterion;
  evaluate the initial screening design by determining an initial score for the primary criterion for the initial screening design, wherein the initial score indicates an efficiency of the initial screening design at identifying the one or more active factors;
  determine whether to modify the initial screening design based on modification criteria comprising one or more of the secondary criterion, the metric N, and the quantity p;
  responsive to determining, based on the modification criteria, to modify the initial screening design, generate an updated screening design for the initial screening design by:
    generating one or more modified screening designs that each has at least one option for a corresponding test case different from the initial screening design;
    evaluating the one or more modified screening designs by computing a respective score for the primary criterion for each of the one or more modified screening designs;
    determining that each of the one or more modified screening designs satisfies the primary criterion by respectively comparing the respective score for the primary criterion to the initial score for the primary criterion or a threshold score for the primary criterion;
    computing a score for the secondary criterion for a given design of the one or more modified screening designs; and
    selecting, based on the score for the secondary criterion, a given design of the one or more modified screening designs as the updated screening design; and
  output an indication of the updated screening design for the output design of the experiment.

2. The computer-program product of claim 1,
wherein the instructions are operable to cause the computing device to select, using the stored instructions, as the initial screening design a given one of any preexisting designs that have N plurality of test cases for an experiment of p factors, responsive to the determining there are stored instructions for directly generating the initial screening design for the experiment that has N plurality of test cases for an experiment of p factors; and
wherein the modification criteria comprises only the secondary criterion.

3. The computer-program product of claim 1,
wherein the instructions are operable to cause the computing device to select, using the stored instructions, as the initial screening design a candidate screening design that does not have N plurality of test cases or does not have p factors, responsive to the determining there are not stored instructions for directly generating the initial screening design for the experiment that has N plurality of test cases for an experiment of p factors; and
wherein the modification criteria comprises the secondary criterion, the metric N, and the quantity p.

4. The computer-program product of claim 1,
wherein the secondary criterion is a secondary criterion for determining an error rate for outcomes of the experiment according to the output design;
wherein the modification criteria comprises the secondary criterion; and
wherein the generating one or more modified screening designs that each has at least one option different from the initial screening design comprises generating a first modified screening design that has more test cases that are assigned the same options for each factor of a respective test case than the initial screening design.

5. The computer-program product of claim 1, wherein the secondary criterion is a secondary criterion for evaluating an effect of an interaction between multiple factors on outcomes of the experiment according to the output design.

6. The computer-program product of claim 5, wherein the secondary criterion is a secondary criterion related to minimizing an aliasing or a correlation for the multiple factors.

7. The computer-program product of claim 5, wherein the instructions are operable to cause the computing device to:
  generate the updated screening design by computing respective model matrices, each representing modeled predicted effects of the one or more factors on the outcomes of testing according to respective ones of multiples ones of the one or more modified screening designs; and
  the instructions are operable to cause the computing device to generate the updated screening design for the output design by selecting one of the multiple ones based on the respective model matrices.

8. The computer-program product of claim 1, wherein the instructions are operable to cause the computing device to select the initial screening design by executing the stored instructions to:
  directly generate, responsive to the obtained metric N and the obtained input indicating a quantity p of an indicated plurality of factors for the output design, one or more candidate initial screening designs; or
  retrieve one or more candidate initial screening designs from memory.

9. The computer-program product of claim 1,
  wherein the instructions are operable to cause the computing device to determine that a given screening design that satisfies the metric N and the quantity p cannot be directly generated from the stored instructions;
  wherein the modification criteria comprises metric N and the quantity p; and
  wherein the stored instructions comprises at least one set of instructions, correlated with both a given metric indicating an amount of a plurality of test cases and a given number of factors, to directly generate a screening design.

10. The computer-program product of claim 9, wherein the instructions are operable to cause the computing device to:
  select one or more candidate screening designs that can be directly generated from the stored instructions; and
  adjust a given candidate screening design to have an adjusted screening design with N test cases.

11. The computer-program product of claim 10, wherein the instructions are operable to cause the computing device to adjust the given candidate screening design by one or more of:
  generating a test case and adding it to the given candidate screening design;
  selecting a test case from the given candidate screening design and removing it from the given candidate screening design; and
  combining multiple candidate screening designs.

12. The computer-program product of claim 10, wherein the instructions are operable to cause the computing device to generate the updated screening design by:
  generating multiple candidate updated screening designs by modifying one or more options of the adjusted screening design;
  computing a respective score for the primary criterion for each of the multiple candidate updated screening designs; and
  selecting one of the candidate updated screening designs as the generated updated screening design based on the respective score.

13. The computer-program product of claim 1,
  wherein the experiment comprises at least one continuous factor and at least one categorical factor; and
  wherein continuous factors have a range of options available for implementing in the experiment, and categorical factors have a set of discrete options available for implementing in testing the experiment.

14. The computer-program product of claim 1, wherein the stored instructions for generating the initial screening design are stored instructions derived from a construction method for a preexisting design that is one of multiple preexisting designs, wherein the multiple preexisting designs comprise one or more of:
  a preexisting design constructed from a Hadamard matrix; and
  a preexisting design constructed from a circulant block matrix.

15. The computer-program product of claim 1,
  wherein the instructions are operable to cause a computing device to:
    display a graphical user interface indicating a plurality of user options for indicating different types for factors of the experiment; and
    receive, via the graphical user interface, an indication of type for at least one of the indicated plurality of factors indicated by the obtained input; and
  wherein the different types include a type indicative of a predictive value of a given factor on outcomes of testing according to the output design of the experiment.

16. The computer-program product of claim 1, wherein the instructions are operable to cause a computing device to obtain the secondary criterion for the output design by:
  displaying a graphical user interface indicating a plurality of secondary criterion for user selection of the secondary criterion for the output design of the experiment; and
  receiving user input indicating a selected one of the plurality of secondary criterion.

17. The computer-program product of claim 1,
  wherein the initial score indicates an Alias-efficiency, a D-efficiency, a G-efficiency, an A-efficiency, or an I-efficiency for the primary criterion compared to a respective efficiency of an orthogonal design; and
  wherein the instructions are operable to cause the computing device to:
    display a graphical user interface indicating a plurality of options for selecting, from multiple primary criterion, the primary criterion, wherein each of the multiple primary criterion indicate one of different efficiency computations, the different efficiency computations comprising one or more of computations for computing the Alias-efficiency, the D-efficiency, the G-efficiency, the A-efficiency, and the I-efficiency; and
    receive a user selection of the primary criterion of the multiple primary criterion.

18. The computer-program product of claim 1, wherein the instructions are operable to cause a computing device to output an indication of the updated screening design by displaying, via a graphical user interface, an array for the output design, wherein each row of the array represents one of the test cases of the experiment and each column of the array represents one of the factors of the indicated plurality of factors.

19. The computer-program product of claim 1, wherein the instructions are operable to cause a computing device to select an initial screening design by:
  identifying multiple candidate initial screening designs correlated with N respective test cases each with p factors; and
  selecting one of the multiple candidate initial screening designs by:
    determining a maximum of respective computed scores for the primary criterion for each of the multiple candidate initial screening designs; or
    respectively comparing each respective computed score for the primary criterion for each of the multiple candidate initial screening designs to a threshold score for the primary criterion.

20. A computer-implemented method comprising:
obtaining a metric N indicating a quantity of a plurality of test cases for an output design of an experiment, wherein each element of a test case of the output design is a test condition for testing one of factors for the experiment, and wherein a test condition comprises one of different options for a given factor of the experiment;
obtaining input indicating a quantity p of an indicated plurality of factors for the output design;
determining whether there are stored instructions for generating an initial screening design for the experiment, the initial screening design for identifying one or more active factors of the experiment each of which independently affect an outcome of a given test case of the experiment;
responsive to determining that there are stored instructions for generating the initial screening design for the experiment, selecting, using the stored instructions, the initial screening design for the experiment;
obtaining a primary criterion and a secondary criterion for scoring the output design, the secondary criterion different from the primary criterion;
evaluating the initial screening design by determining an initial score for the primary criterion for the initial screening design, wherein the initial score indicates an efficiency of the initial screening design at identifying the one or more active factors;
determining whether to modify the initial screening design based on modification criteria comprising one or more of the secondary criterion, the metric N, and the quantity p;
responsive to determining, based on the modification criteria, to modify the initial screening design, generating an updated screening design for the initial screening design by:
  generating one or more modified screening designs that each has at least one option for a corresponding test case different from the initial screening design;
  evaluating the one or more modified screening designs by computing a respective score for the primary criterion for each of the one or more modified screening designs;
  determining that each of the one or more modified screening designs satisfies the primary criterion by respectively comparing the respective score for the primary criterion to the initial score for the primary criterion or a threshold score for the primary criterion;
  computing a score for the secondary criterion for a given design of the one or more modified screening designs; and
  selecting, based on the score for the secondary criterion, a given design of the one or more modified screening designs as the updated screening design; and
outputting an indication of the updated screening design for the output design of the experiment.

21. The computer-implemented method of claim 20,
further comprising selecting, using the stored instructions, as the initial screening design a given one of any preexisting designs that have N plurality of test cases for an experiment of p factors, responsive to the determining there are stored instructions for directly generating the initial screening design for the experiment that has N plurality of test cases for an experiment of p factors; and
wherein the modification criteria comprises only the secondary criterion.

22. The computer-implemented method of claim 20,
further comprising selecting, using the stored instructions, as the initial screening design a candidate screening design that does not have N plurality of test cases or does not have p factors, responsive to the determining there are not stored instructions for directly generating the initial screening design for the experiment that has N plurality of test cases for an experiment of p factors; and
wherein the modification criteria comprises the secondary criterion, the metric N, and the quantity p.

23. The computer-implemented method of claim 20, wherein the secondary criterion is a secondary criterion related to minimizing an aliasing or a correlation for an interaction between multiple factors of the experiment.

24. The computer-implemented method of claim 20,
wherein the determining whether there is a preexisting stored design for an initial screening design for the experiment further comprises determining that a given screening design that satisfies the metric N and the indicated plurality of factors cannot be directly generated from the stored instructions;
wherein the modification criteria comprises metric N and indicated plurality of factors; and
wherein the stored instructions comprises at least one set of instructions, correlated with both a given metric indicating an amount of a plurality of test cases and a given number of factors, to directly generate a screening design.

25. The computer-implemented method of claim 24, wherein the method further comprises:
selecting one or more candidate screening designs that can be directly generated from the stored instructions; and
adjusting a given candidate screening design to have an adjusted screening design with N test cases.

26. The computer-implemented method of claim 25, wherein the adjusting the given candidate screening design further comprises one or more of:
generating a test case and adding it to the given candidate screening design;
selecting a test case from the given candidate screening design and removing it from the given candidate screening design; and
combining multiple candidate screening designs.

27. The computer-implemented method of claim 20, wherein the stored instructions for generating the initial screening design are stored instructions derived from a construction method for a preexisting design that is one of multiple preexisting designs, wherein the multiple preexisting designs comprise one or more of:
a preexisting design constructed from a Hadamard matrix; and
a preexisting design constructed from a circulant block matrix.

28. The computer-implemented method of claim 20,
wherein the initial score indicates an Alias-efficiency, a D-efficiency, a G-efficiency, an A-efficiency, or an I-efficiency for the primary criterion compared to a respective efficiency of an orthogonal design; and
wherein the computer-implemented method further comprises:
displaying a graphical user interface indicating a plurality of options for selecting, from multiple primary criterion, the primary criterion, wherein each of the multiple primary criterion indicate one of different efficiency computations, the different efficiency computations comprising one or more of computations for computing the Alias-efficiency, the D-efficiency, the G-efficiency, the A-efficiency, and the I-efficiency; and receiving a user selection of the primary criterion of the multiple primary criterion.

29. The computer-implemented method of claim 20, wherein the selecting, using the preexisting stored design, the initial screening design for the experiment comprises:

identifying multiple candidate initial screening designs correlated with N respective test cases each with p factors; and selecting one of the multiple candidate initial screening designs by:

determining a maximum of respective computed scores for the primary criterion for each of the multiple candidate initial screening designs; or respectively comparing each respective computed score for the primary criterion for each of the multiple candidate initial screening designs to a threshold score for the primary criterion.

30. A computing device comprising processor and memory, the memory containing instructions executable by the processor wherein the computing device is configured to:

obtain a metric N indicating a quantity of a plurality of test cases for an output design of an experiment, wherein each element of a test case of the output design is a test condition for testing one of factors for the experiment, and wherein a test condition comprises one of different options for a given factor of the experiment;

obtain input indicating a quantity p of an indicated plurality of factors for the output design;

determine whether there are stored instructions for generating an initial screening design for the experiment, the initial screening design for identifying one or more active factors of the experiment each of which independently affect an outcome of a given test case of the experiment;

responsive to determining that there are stored instructions for generating the initial screening design for the experiment, select, using the stored instructions, the initial screening design for the experiment;

obtain a primary criterion and a secondary criterion for scoring the output design, the secondary criterion different from the primary criterion;

evaluate the initial screening design by determining an initial score for the primary criterion for the initial screening design, wherein the initial score indicates an efficiency of the initial screening design at identifying the one or more active factors;

determine whether to modify the initial screening design based on modification criteria comprising one or more of the secondary criterion, the metric N, and the quantity p;

responsive to determining, based on the modification criteria, to modify the initial screening design, generate an updated screening design for the initial screening design by:

generating one or more modified screening designs that each has at least one option for a corresponding test case different from the initial screening design;

evaluating the one or more modified screening designs by computing a respective score for the primary criterion for each of the one or more modified screening designs;

determining that each of the one or more modified screening designs satisfies the primary criterion by respectively comparing the respective score for the primary criterion to the initial score for the primary criterion or a threshold score for the primary criterion;

computing a score for the secondary criterion for a given design of the one or more modified screening designs; and selecting, based on the score for the secondary criterion, a given design of the one or more modified screening designs as the updated screening design; and output an indication of the updated screening design for the output design of the experiment.

* * * * *

UNITED STATES PATENT AND TRADEMARK OFFICE
CERTIFICATE OF CORRECTION

PATENT NO. : 10,535,422 B2
APPLICATION NO. : 16/507769
DATED : January 14, 2020
INVENTOR(S) : Ryan Adam Lekivetz et al.

Page 1 of 1

It is certified that error appears in the above-identified patent and that said Letters Patent is hereby corrected as shown below:

In the Specification

Column 67, Line 12, should read -- N or select a default value for metric N, which may be. --.

Column 70, Line 37, should read -- initial design may already satisfy N or P. In this case, the --.

Signed and Sealed this
Twentieth Day of October, 2020

Andrei Iancu
*Director of the United States Patent and Trademark Office*